United States Patent [19]

Casida et al.

[11] Patent Number: 5,502,073
[45] Date of Patent: Mar. 26, 1996

[54] HETEROCYCLIC PESTICIDAL COMPOUNDS

[75] Inventors: John E. Casida, Berkeley, Calif.; Michael Elliott, Hertfordshire, United Kingdom; David A. Pulman, Hertfordshire, England

[73] Assignees: The Wellcome Foundation, London, England; The Regents of the University of California, Oakland, Calif.

[21] Appl. No.: 200,364

[22] Filed: Feb. 23, 1994

Related U.S. Application Data

[63] Continuation of Ser. No. 74,157, Jun. 9, 1993, abandoned, which is a continuation of Ser. No. 807,631, Dec. 13, 1991, abandoned, which is a continuation of Ser. No. 641,635, Jan. 17, 1991, abandoned, which is a continuation of Ser. No. 201,796, Jun. 1, 1988, abandoned, which is a continuation-in-part of Ser. No. 171,357, Mar. 21, 1988, abandoned.

[30] Foreign Application Priority Data

Jun. 5, 1987 [GB] United Kingdom ............... 8713222
Sep. 5, 1987 [GB] United Kingdom ............... 8720928

[51] Int. Cl.$^6$ ........................... A01N 43/32; C07D 339/08
[52] U.S. Cl. ................................ 514/436; 549/4; 549/20; 549/22
[58] Field of Search .................... 514/436; 549/4, 549/20, 22

[56] References Cited

U.S. PATENT DOCUMENTS

| | | | |
|---|---|---|---|
| 3,878,216 | 4/1975 | Schneider | 549/21 |
| 4,640,929 | 2/1987 | Mitsudera et al. | 549/21 |

FOREIGN PATENT DOCUMENTS

| | | | |
|---|---|---|---|
| 0061794 | 10/1982 | European Pat. Off. . | |
| 0061789 | 10/1982 | European Pat. Off. . | |
| 0073378 | 3/1983 | European Pat. Off. | 549/20 |
| 0102062 | 3/1984 | European Pat. Off. . | |
| 876018 | 3/1953 | Germany . | |
| 0160061 | 4/1983 | Germany | 549/20 |
| 3437935 | 4/1986 | Germany . | |
| 60-45571 | 12/1985 | Japan . | |

OTHER PUBLICATIONS

Bailer, J. *Tetrahedron*, vol. 36 pp. 901–911 (1980).
Prill, E. A. et al, *Contributions from Boyce Thompson Institute* vol. 14, pp. 397–403, 1947.
*Chemical Abstracts* 88(11):74354g. Kubota et al. (1977).
Eliel, Ernest L. et al. *J. Am. Ch. Soc.* 98–12, Jun. 9, 1976 p. 3583.

*Primary Examiner*—Jacqueline Haley
*Attorney, Agent, or Firm*—Nixon & Vanderhye

[57] ABSTRACT

Compounds of the formula (I)

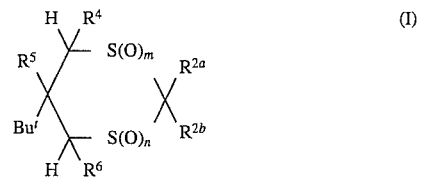

which contain between 10 and 27 carbon atoms, and wherein m and n are independently selected from 0, 1 and 2; $R^{2a}$ is hydrogen, methyl, or ethyl; $R^{2b}$ is acetylene or contains between 3 and 18 carbon atoms and is a group $R^7$, wherein $R^7$ is a $C_{1-13}$ non-aromatic hydrocarbyl group, optionally substituted by a cyano or $C_{1-4}$ carbalkoxy group and/or by one or two hydroxy groups and/or by one to five halo atoms which are the same or different and/or by one to three groups $R^8$ which are the same or different and each contain one to four hetero atoms, which are the same or different and are chosen from oxygen, sulphur, nitrogen and silicon, 1 to 10 carbon atoms and optionally 1 to 6 fluoro or chloro atoms or $R^{2b}$ is a 6-membered aromatic ring substituted by cyano and/or by one to three groups $R^8$ and/or by a group —C≡CH, —C≡C-$R^7$ or C≡C-halo and/or by one to five halo atoms and/or by one to three $C_{1-4}$ haloalkyl groups wherein $R^7$ and $R^8$ are as hereinbefore defined; $R^4$ and $R^6$ are the same or different and are chosen from hydrogen, methyl, trifluoromethyl or cyano; and $R^5$ is hydrogen or methyl provided that $R^{2b}$ is not propyl or butyl are described which have pesticidal activity, particularly against arthropod pests. Pesticidal formulations containing the compounds of the formula (I), their use in the control of pests and method for their preparation are also disclosed.

10 Claims, No Drawings

HETEROCYCLIC PESTICIDAL COMPOUNDS

This invention was made with United States Government support under Grant No. P01 ES 00049 from the National Institutes of Health to The University of California. The United States Government has certain rights in this invention.

This is a continuation of application Ser. No. 08/074,157, filed Jun. 9, 1993 abandoned which is a continuation of Ser. No. 07/807,631 filed Dec. 13, 1991 abandoned which is a continuation of Ser. No. 07/641,635 filed Jan. 17, 1991 abandoned which is a continuation of Ser. No. 07/201,796 filed Jun. 1, 1988 abandoned which is a continuation-in-part of Ser. No. 07/171,357 filed Mar. 21, 1988, now abandoned.

The present invention is concerned with a method of controlling pests such as arthropods, e.g. insects and acarine pests, and helminths, e.g. nematodes, by contacting the pests with novel pesticides. The invention is also concerned with the novel pesticides used for controlling the pests and processes for making such pesticides.

Current classes of pesticides effectively control some but not all pest species. It is also desirable to have new classes of pesticides since pests tend to develop resistance to any one pesticide, or sometimes to any one class of pesticide, after they have been selected with or exposed to such pesticides over a period of time.

Certain 2,5-dialkylsubstituted dithianes have been investigated as liquid crystal materials (see for example Mol. Cryst. Liq. Cryst., 131. 101) but no pesticidal activity has been reported for such compounds.

It has been discovered that a class of novel 2,5-disubstituted dithianes has pesticidal activity.

Accordingly, the present invention provides a compound of the formula (I):

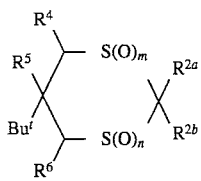
(I)

which contains between 10 and 27 carbon atoms, and wherein m and n are independently selected from 0, 1 and 2; $R^{2a}$ is hydrogen, methyl, or ethyl; $R^{2b}$ is acetylene or contains between 3 and 18 carbon atoms and is a group $R^7$, wherein $R^7$ is a $C_{1-13}$ non aromatic hydrocarbyl group, optionally substituted by a cyano or $C_{1-4}$ carbalkoxy group and/or by one or two hydroxy groups and/or by one to five halo atoms which are the same or different and/or by one to three groups $R^8$ which are the same or different and each contains one to four hetero atoms, which are the same or different and are chosen from oxygen, sulphur, nitrogen and silicon, 1 to 10 carbon atoms and optionally 1 to 6 fluoro or chloro atoms or $R^{2b}$ is a 6-membered aromatic ring substituted by cyano and/or by one to three groups $R^8$ and/or by a group —C≡CH or C≡C-halo and/or by one to five halo atoms and/or by one to three $C_{1-4}$ haloalkyl groups wherein $R^7$ and $R^8$ are as hereinbefore defined; $R^4$ and $R^6$ are the same or different and are chosen from hydrogen, methyl, trifluoromethyl or cyano; and $R^5$ is hydrogen or methyl provided that $R^{2b}$ is not propyl or butyl.

By the term "halo" is meant fluoro, chloro, bromo or iodo.

By the term "non-aromatic hydrocarbyl" group is meant an alkyl, alkenyl or alkynyl group (including a cyclic alkyl or alkenyl group optionally substituted by alkyl, alkenyl or alkynyl; and alkyl or alkenyl substituted by cyclic alkyl and alkenyl).

By the term "6-membered aromatic ring" is meant phenyl and heteroaromatic rings such as pyridyl.

$R^{2b}$ suitably contains between 3 and 12 carbon atoms. $R^{2b}$ is suitably a $C_{3-9}$ alkyl, alkenyl or alkynyl group, each of which may be optionally substituted by halo or a group $R^8$, or a substituted phenyl or cyclohexyl group. The group $R^8$ is linked to the hydrocarbyl group or the aromatic ring via a hetero atom of $R^8$. Suitable substituents $R^8$ for the group $R^7$ include alkoxy, alkenyloxy, alkynyloxy, alkoxyalkoxy, acyloxy, alkylthio, alkenylthio, alkynylthio, alkynylsulphonyl, alkynylsulphinyl, alkynyloximino, trialkylsilyl, haloalkylthio, haloalkoxy, haloalkenyloxy, haloalkynyloxy, sulphonyl, sulphinyl, alkyloximino, carbalkoxy and mono or di-substituted alkylamino groups. When a silyl group is present this is normally adjacent to an ethynyl group. Preferred substituents $R^8$ include alkoxy, alkoxyalkoxy, alkenyloxy, alkynyloxy, haloalkoxy, haloalkenyloxy and haloalkynyloxy. Suitably $R^7$ is substituted by up to two substituents $R^8$ and preferably $R^7$ is unsubstituted or contains one substituent $R^8$. Preferably there is only one silyl group present. The sulphur atoms present may be in an oxidised form if desired. Preferably there is a maximum of two sulphur atoms present in $R^{2b}$. Suitably there is a maximum of four and preferably a maximum of three oxygen atoms in $R^{2b}$. Preferably there is only one nitrogen atom present in $R^{2b}$.

In one suitable embodiment, $R^{2b}$ is a phenyl group substituted at the 3-,4- or 5-positions by one to three substituents each selected from halo, $C_{1-4}$ haloalkyl, C haloalkoxy C haloalkylthio, cyano, or a group $(C\!\!\equiv\!\!C)_pR^9$ wherein p is 1 or 2 and $R^9$ is hydrogen, bromo, chloro, iodo or a group $S(O)_qR^{10}$ wherein q is 0 1 or 2 and $R^{10}$ is trifluoromethyl methyl or ethyl; or $R^9$ is an aliphatic group containing up to five carbon atoms optionally substituted by $C_{1-4}$ alkoxy, $C_{1-6}$ alkoxyalkoxy, $C_{1-8}$ acyloxy, halo or hydroxy or $R^9$ is a group $COR^{11}$ wherein $R^{11}$ is hydrogen, $C_{1-4}$ alkoxy, $C_{1-4}$ alkyl or a group $NR^{12}R^{13}$ wherein $R^{12}$ and $R^{13}$ are independently selected from hydrogen, methyl or ethyl; or $R^9$ is $SiR^{14}, R^{15}, R^{16}$ wherein $R^{14}$ and $R^{15}$ are the same or different and are each $C_{1-4}$ aliphatic groups and $R^{16}$ is a $C_{1-4}$ aliphatic group or phenyl provided that $R^{14}, R^{15}$ and $R^{16}$ do not contain more than 10 carbon atoms in total. The phenyl group is additionally optionally substituted at the 2- and/or 6-positions by fluoro or chloro. Suitably when the substituent is a group $(C\!\!\equiv\!\!C)_pR^9$, there is only one such substituent on the phenyl ring.

In one preferred embodiment $R^{2b}$ is phenyl substituted at the 3-, 4- or 5-positions by one to three substituents each selected from halo, cyano, $C_{1-4}$ haloalkyl or a group C≡C—$R^{17}$ where $R^{17}$ is hydrogen, methyl, or ethyl each optionally substituted by hydroxy methoxy ethoxy acetoxy; or $R^{17}$ is $C_{1-4}$ carbalkoxy, or a silyl group substituted by three $C_{1-4}$ alkyl groups $R^{2b}$ is additionally optionally substituted at the 2- and/or 6- positions by fluoro or chloro.

In a second preferred embodiment $R^{2b}$ is a group —A(C≡C)Z, wherein A is a $C_{3-5}$ aliphatic chain optionally containing a double bond and/or an oxygen atom and/or a group S(O)q wherein q is 0, 1 or 2 optionally substituted by halo, $C_{1-4}$ alkyl, $C_{1-4}$ haloalkyl, $C_{1-4}$ carbalkoxy or cyano and Z is hydrogen, $C_{1-5}$ alkyl, $C_{1-3}$ alkoxymethyl or a group $SiR^{14}, R^{15}, R^{16}$ wherein $R^{14}, R^{15}$ and $R^{16}$ are as hereinbefore defined.

In a third preferred embodiment $R^{2b}$ is a group —$BZ^1$, wherein B is a group —$CH_2O$— or $CH_2S(O)q$ wherein $_q$ is 0 1 or 2 or a $C_{2-6}$ aliphatic group each of which may be optionally substituted by one to three halo atoms and $Z^1$ is silyl substituted by three $C_{1-4}$ alkyl groups or $Z^1$ is a group

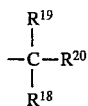

wherein $R^{18}$, $R^{19}$ and $R^{20}$ are the same or different and are each independently selected from halo, cyano, $C_{1-5}$ carbalkoxy, or a $C_{1-4}$ aliphatic group optionally substituted by halo, cyano, $C_{1-5}$ carbalkoxy, $C_{1-4}$ alkoxy or a group $S(O)_q R^{21}$ wherein q is 0, 1 or 2 and $R^{21}$ is $C_{1-4}$ alkyl, or $R^{18}$, $R^{19}$ and $R^{20}$ are selected from $C_{1-4}$ alkoxy or a group $S(O)_w R^{22}$ wherein w is 0 1 or 2 and $R^{22}$ is $C_{1-4}$ alkyl optionally substituted by fluoro or $R^{18}$ and $R^{19}$ are linked to form a $C_{3-6}$ cycloalkyl ring, or one of $R^{18}$, $R^{19}$ and $R^{20}$ may be hydrogen.

By the term "aliphatic group" is meant an alkyl, alkenyl or alkynyl group.

Most suitably B is a group —C≡C— —CH=CH— or —CH$_2$CH$_2$—.

Preferably $Z^1$ is tertiary butyl, trichloromethyl or 2-methoxyprop-2-yl.

Preferably $R^{2a}$ is hydrogen or methyl.

Preferably $R^4$ and $R^6$ are hydrogen.

In a fourth preferred embodiment $R^{2b}$ is a group

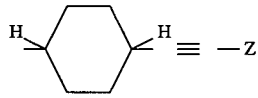

wherein Z is as hereinbefore defined:

A preferred group of compounds of the formula (I) is that in which $R^{2b}$ contains a —(C≡C) fragment or terminates in a group $Z^1$ as hereinbefore defined.

In accordance with another embodiment of the present invention, there is provided a compound of formula (I) wherein $R^{2a}$, $R^4$, $R^5$, $R^6$, m and n are as hereinbefore defined and $R^{2b}$ is substituted phenyl or optionally substituted $C_{4-8}$ alkyl or cycloalkyl or $C_{4-5}$ N-containing heterocycle, the substituents being selected from halo, $C_{1-4}$ haloalkyl, cyano or a group (C≡C)$_p R^{9a}$ wherein p is 1 or 2 and $R^{9a}$ is hydrogen bromo, chloro, iodo or a group $S(O)_q R^8$ as hereinbefore defined, or $R^{9a}$ is an aliphatic group containing up to five carbon atoms optionally substituted by $C_{1-4}$ alkoxy, halo or hydroxy or $R^{9a}$ is a group $COR^{11}$ or $SiR^{14}$, $R^{15}$, $R^{16}$ wherein $R^{11}$, $R^{14}$, $R^{15}$, $R^{16}$, are as hereinbefore defined.

In accordance with a further embodiment of the present invention, there is provided a compound of formula (Ia):

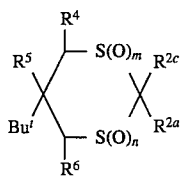

wherein m n, $R^{2a}$, $R^4$, $R^5$ and $R^6$ are as hereinbefore defined and $R^{2c}$ is a group (C≡C)$_r$ Y(C≡C)$_t$ $Z^2$ wherein r is 0 or 1 and t is 1 or 2 and the sum of r and t is not greater than 2, Y is a single bond, a group
wherein v is 1 2 or 3 and the (C≡C)$_v Z^2$ fragment is attached to the a or b position of the ring, or Y is a polymethylene chain containing between 1 and 8 carbon atoms in which one or two heteroatoms and/or double or triple bonds may be interspersed, the chain being optionally substituted by one to four substituents which may be the same or different and are each independently selected from hydroxy, oxo, halo, $C_{1-4}$ alkyl, $C_{1-4}$ alkoxy, $C_{1-4}$ acyloxy, epoxy, a $C_{1-4}$ alkylidene group, a $C_{1-6}$ carbalkoxy group, $C_{1-4}$ haloalkyl or cyano, $Z^2$ is selected from hydrogen, $C_{1-10}$ hydrocarbyl optionally substituted by halo, $C_{1-4}$ alkoxy, hydroxy, oxo, a group $S(O)_q R^{10}$ as hereinbefore defined, cyano, $C_{1-4}$ acyloxy or carbalkoxy, or $Z^2$ is halo or a group $SiR^{14}$, $R^{15}$, $R^{16}$ wherein $R^{14}$, $R^{15}$ and $R^{16}$ are as hereinbefore defined or $Z^2$ is a group $R^{23}OCO$ wherein $R^{23}$ is $C_{1-4}$ alkyl; provided that (C≡C)$_r$ Y(C≡C)$_t Z^2$ contains up to a maximum of 18 carbon atoms.

Suitably r is 0, t is 1 and Y is a single bond or a $C_{3-5}$ polymethylene chain optionally containing a double bond and $Z^2$ is hydrogen $C_{1-5}$ alkyl, $C_{1-3}$ alkoxymethyl or a group $SiR^{24}$, $R^{25}$, $R^{26}$ wherein $R^{24}$, $R^{25}$ and $R^{26}$ are the same or different and each is selected from $C_{1-4}$ alkyl.

Preferably Y is a single bond and $Z^2$ is $C_{1-4}$ alkyl and preferably $R^{2c}$ is a group (C≡C)Bu$^t$.

The compounds of the formula (I) may exist in a number of stereoisomeric forms. The present invention encompasses both individual conformational and stereoisomers and mixtures thereof. The present invention also encompasses radiolabelled compounds of the formula (I), particularly those in which one carbon atom is $C^{14}$ or one or more hydrogen atoms are replaced by tritium.

Preferred compounds of the invention include:

2(e)-(4-Bromophenyl)-5(e)-tert-butyl-1,3-dithiane
5(e)-tert-Butyl-2(e)-(4-chlorophenyl)-1,3-dithiane
5(e)-tert-Butyl-2(e)-(4-iodophenyl)-1,3-dithiane
5(e)-tert-Butyl-2(e)-(4-ethynylphenyl)-1,3-dithiane
2(e)-(4-Bromophenyl)-5(e)-tert-butyl-2(a)-methyl-1,3-dithiane
5(e)-tert-Butyl-2(e)-[4-(2-trimethylsilylethynyl)phenyl]-1,3-dithiane
5(e)-tert-Butyl-2(e)-(4-ethynylphenyl)-2(a)-methyl-1,3-dithiane
2(e)-(4-Bromophenyl)-5(e)-tert-butyl-2(a)-ethyl-1,3-dithiane
5(e)-tert-Butyl-2(e)-(3,4-dichlorophenyl)-1,3-dithiane
5(e)-tert-Butyl-2(a)-(3,4-dichlorophenyl)-1,3-dithiane
5(e)-tert-Butyl-2(e)-(4-cyanophenyl)-1,3-dithiane
5(e)-tert-Butyl-2(e)-(4-cyanophenyl)-2(a)-methyl-1,3-dithiane
5(e)-tert-Butyl-2(e)-[4-(prop-1-ynyl)phenyl]-1,3-dithiane
5(e)-tert-Butyl-2(a)-(4-cyanophenyl)-2(e)-methyl-1,3-dithiane
5(e)-tert-Butyl-2(e)-(3,4-dichlorophenyl)-2(a)-methyl-1,3-dithiane
5(e)-tert-Butyl-2(e)-(3-trifluoromethylphenyl)-1,3-dithiane
5(e)-tert-Butyl-2(e)-(3,3-dimethylbut-1-ynyl)-1,3-dithiane
5(e)-tert-Butyl-2(e)-(trimethylsilylethynyl)-1,3-dithiane
5(e)-tert-Butyl-2(e)-(3,3-dimethylbut-1-ynyl)-2(a)-methyl-1,3-dithiane
cis-5(e)-tert-Butyl-2 (a)-(3,4-dichlorophenyl)-2(e)-methyl-1,3-dithiane
trans-5(e)-tert-Butyl-2(a)-methyl-2(e)-(3-trifluoromethylphenyl)-1,3-dithiane
cis-5(e)-tert-Butyl-2(e)-methyl-2(a)-(3-trifluoromethylphenyl)-1,3-dithiane
cis-2(a)-(4-Bromophenyl)-5(e)-tert-butyl-2(e)-methyl-1,3-dithiane
cis-5(e)-tert-Butyl-2(a)-(4-bromophenyl)-1,3-dithiane
trans-5(e)-tert-Butyl-2(e)-(3,5-dichlorophenyl)-2(a)-methyl-1,3-dithiane
cis-5(e)-tert-Butyl-2(a)-(2,4-dichlorophenyl)-2(e)-methyl-1,3-dithiane
cis-5(e)-tert-Butyl-2(e)-methyl-2(a)-(4-trifluoromethylphenyl)-1,3-dithiane
trans-5(e)-tert-Butyl-2(a)-methyl-2(e)-(4-trifluoromethylphenyl)-1,3-dithiane trans-2(e)-(4-Bromo-2-fluorophenyl)-5(e)-tert-butyl-1,3-dithiane
trans-5(e)-tert-Butyl-2(e)-(4-trifluoromethylphenyl)-1,3-dithiane
trans-2(e)-[3,5-Bis(trifluoromethyl)phenyl]-5(e)-tert-butyl-2(a)-methyl-1,3-dithiane
trans-2(e)-[3,5-Bis(trifluoromethyl)phenyl]-5(e)-tert-butyl-1,3-dithiane
trans-5(e)-tert-Butyl-2(e)-(3,4,5-trichlorophenyl)-1,3-dithiane
cis-2(a)-(4-Bromo-3-trifluoromethylphenyl)-5(e)-tert-butyl-2(e)-methyl-1,3-dithiane
trans-2(e)-(4-Bromo-3-trifluoromethylphenyl)-5(e)-tert-butyl-2(a)-methyl-1,3-dithiane
trans-3-{4-[5(e)-tert-Butyl-2(a)-methyl-1,3-dithian-2-yl]phenyl}prop-2-ynol
trans-2(e)-(4-Bromo-3 -chlorophenyl)-5(e)-tert-butyl-1,3-dithiane
trans-5(e)-tert-Butyl-2(e)-(2,4-dichlorophenyl)-1,3-dithiane
5(e)-tert-Butyl-2(e)-(3,5-dichlorophenyl)-1,3-dithiane
5(e)-tert-Butyl-2(e)-(2,3,4,5,6-pentafluorophenyl)-1,3-dithiane
5(e)-tert-Butyl-2(e)-[2-fluoro-4-(trimethylsilylethynyl)phenyl]-1,3-dithiane
5(e)-tert-Butyl-2(e)-(4-ethynyl-2-fluorophenyl)-1,3-dithiane
2-(4-Bromo-3,5-dichlorophenyl)-5(e)-tert-butyl-1,3-dithiane
trans-5(e)-tert-Butyl-2(e)-(4-ethynyl-3-fluorophenyl)-1,3-dithiane
5(e)-tert-Butyl-2(a)-methyl-2(e)-(2,3,4,5,6-pentafluorophenyl)-1,3-dithiane
trans-5(e)-tert-Butyl-2(e)-(2-fluoro-4-trifluoromethylphenyl)-1,3-dithiane
3-{4-trans-5(e)-tert-Butyl-1,3-dithian-2(e)-yl)phenyl}prop-2-ynol
3-[4-(5(e)-tert-Butyl-1,3-dithian-2(e)-yl]phenyl]prop-2-ynyl acetate
Methyl 3-[4-(5(e)-tert-butyl-1,3-dithian-2(e)-ylphenyl]prop-2-ynoate
5(e)-tert-Butyl-2(a)-methyl-2(e)-(3,4,5-trichlorophenyl)-1,3-dithiane
5-(e)-tert-Butyl-2(e)-methyl-2(a)-(3,4,5-trichlorophenyl)-1,3-dithiane
trans-5(e)-tert-Butyl-2(e)-{4-[3-(2-methoxyethoxy)prop-1-ynyl]phenyl}-1,3-dithiane
5(e)-tert-Butyl-2(e)-[4-(methoxyprop-1-ynyl)phenyl]-1,3-dithiane
cis-5(e)-tert-Butyl-2(a)-(4-ethynylphenyl)-2(e)-methyl-1,3-dithiane
cis-5(e)-tert-Butyl-2(e)-methyl-2(a)-(4-trimethylsilylethynylphenyl)-1,3-dithiane
2(e)-(4-Bromophenyl)-5(e)-tert-butyl-5(a)-methyl-1,3-dithiane
2(a)-(4-Bromophenyl)-5(e)-tert-butyl-5(a)-methyl-1,3-dithiane
2(a)-(4-Bromophenyl)-5(e)-tert-butyl-2(e),5(a)-dimethyl-1,3-dithiane
2(e)-(4-Bromophenyl)-5(e)-tert-butyl-2(a),5(a)-dimethyl-1,3-dithiane
trans-5(e)-tert-Butyl-2(e)-(pent-1-ynyl)-1,3-dithiane
cis-5(e)-tert-Butyl-2(a)-(prop-1-ynyl)-1,3-dithiane
trans-5(e)-tert-Butyl-2(e)-(prop-1-ynyl)-1,3-dithiane
cis-5(e)-tert-Butyl-2(a)-(hex-1-en-5-ynyl)-1,3-dithiane
trans-5(e)-tert-Butyl-2(e)-(hex-1-en-5-ynyl-1,3-dithiane
cis-5(e)-tert-Butyl-2(e)-(pent-4-ynyl)-1,3-dithiane
trans-5(e)-tert-Butyl-2(e)-(hex-5-ynyl)-1,3-dithiane
5(e)-tert-Butyl-2(e)-methyl-2(a)-(prop-1-ynyl)-1,3-dithiane
5(e)-tert-Butyl-2(e)-methyl-2(a)-(trimethylsilylethynyl)-1,3-dithiane
trans-5(e)-tert-Butyl-2(e)-[(E)-3,3,3-trichloroprop-1-enyl]-1,3-dithiane
trans-5(e)-tert-Butyl-2(e)-(3,3,3-trichloropropyl)-1,3-dithiane
trans-2(e)-(1-Bromo-3,3,3-trichloroprop-1-enyl)-5(e)-tert-butyl-1,3-dithiane
5-(e)-tert-Butyl-2(a)-methyl-2(e)-(3,3,3-trichloropropyl)-1,3-dithiane
trans-5(e)-tert-Butyl-2(e)-(3-methoxy-3-methylbut-1-ynyl)-1,3-dithiane
5(e)-tert-Butyl-2-(cyclohexylethynyl)-1,3-dithiane
trans-5(e)-tert-Butyl-2(e)-(trans-4(e)-ethynylcyclohexyl)-1,3-dithiane
cis-5(e)-tert-Butyl-2(a)-(trans-4(e)-ethynylcyclohexyl)-1,3-dithiane
cis-5(e)-tert-Butyl-2(a)-(6-chloro-3-pyridyl)-1,3-dithiane
trans-5(e)-tert-Butyl-2(e)-(2,2-dichloro-3,3-dimethylcyclopropyl)-1,3-dithiane
5(e)-tert-Butyl-2(e)-(3,3-dimethylbutyl)-1,3-dithiane
trans-5(e)-tert-Butyl -2(e)-(3,3-dimethylbutyl)-1,3-dithiane
cis-5(e)-tert-Butyl-2(a)-(3,3-dimethylbutyl)-1,3-dithiane
5(e)-tert-Butyl-2(e)-(3,3-dimethylbut-1-enyl)-1,3-dithiane
5(e)-tert-Butyl-2(e)-(2,2-dimethylpropyl)-2(a)-methyl-1,3-dithiane
trans-5(e)-tert-Butyl-2(e)-[(E)-1-methylhex-1-en-5-ynyl]-1,3-dithiane
5(e)-tert-Butyl-2(e)-(3,3-dimethylbutyl)-5(a)-methyl-1,3-dithiane
5(e)-tert-Butyl-2(a)-[2-( 1-methylcyclopropyl)ethyl]-1,3-dithiane
5(e)-tert-Butyl-2(e)-[2-(1-methylcyclopropyl)ethyl]-1,3-dithiane
cis-5(e)-tert-Butyl-2(a)-(3,3-dimethylpentyl)-1,3-dithiane
trans-5(e)-tert-Butyl-2(e)-(3,3-dimethylpentyl)-1,3-dithiane
5(e)-tert-Butyl-2(e)-(4-ethynylphenyl)-1,3-dithiane 1(e)-oxide
cis-5(e)-tert-Butyl-2(a)-(2,2-dimethylpropyl)-1,3-dithiane 1-oxide
2(e)-(4-Bromophenyl)-5(e)-tert-butyl-1,3-dithiane 1(e)-oxide
5(e)-tert-Butyl-2(a)-ethynyl-2(e)-methyl-1,3-dithiane The present invention also provides for the preparation of the compounds of the formula (I) by methods derived from those known in the art for the preparation of analogous compounds. Thus, the compounds may be prepared by (i) the reaction of a compound of the formula (II):

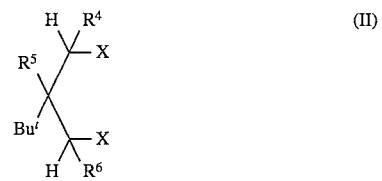

wherein X is SH with a suitable aldehyde or ketone of the formula

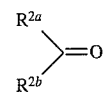

or a reactive derivative thereof, wherein $R^{2a}$, $R^{2b}$, $R^4$, $R^5$ and $R^6$ are as hereinbefore defined and, if required, thereafter oxidising one or both of the ring sulphur atoms.

The reaction is suitably carried out in the presence of a catalyst or of a dehydrating agent in a non-polar solvent at a non-extreme temperature. Suitable catalysts include a dimethyl formamide/dimethyl sulphate catalyst and catalysts such as sulphonic acids or perfluorinated resins thereof or Lewis acids such as boron trifluoride etherate, or stannic chloride or concentrated formic acid which also serves as the reaction medium. Suitable solvents include hydrocarbons such as benzene, toluene or xylene or chlorinated hydrocarbons such as dichloromethane. The reaction is normally performed between 0° and 200° and conveniently between 20° and 120°.

Suitable reactive derivatives of aldehydes and ketones include acetals and ketals.

The compounds of the formula (II) may be prepared from the corresponding diols wherein X is hydroxy via the sulphonate derivatives (i.e., compounds of the formula (II) wherein X is a group $OSO_2R^{27}$ wherein $R^{27}$ is $C_{1-4}$ alkyl or para-tolyl) as outlined in Appendix 1. The preparation of the diols and their conversion to the corresponding dithiols can be carried out by methods known in the art for example as outlined in Appendices 1 and 2.

The aldehydes and ketones reacted with the dithiols of the formular (II) are either known in the literature or are prepared by literature methods, for example, the ethynylcyclohexylcarboxaldehydes are prepared as outlined in Appendix 3.

(ii) When $R^{2a}$ is hydrogen, the reaction of a dithiaborinane-dimethylsulphide complex of a compound of the formula (II) with a carboxylic acid

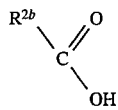

This reaction is carried out in the presence of a reducing agent such as stannous chloride in an inert solvent such as an ether, conveniently tetrahydrofuran, at a non-extreme temperature, for example between −20° and 100° and conveniently between 10° and 30°.

The dithiaborinane-dimethylsulphide complex is prepared from the corresponding dithiol by methods well known to those skilled in the art.

It is often convenient to prepare compounds of the formula (I) by interconversion from other compounds of the formula (I), for example:

(a) when it is required to prepare a compound of the formula (I) which contains an ethynyl group.
  (i) by the reaction of the corresponding compound in which $R^{2b}$ is a 6-membered aromatic ring which contains iodo in place of —C≡C—$R^{28}$ with a compound HC≡C$R^{28}$ wherein $R^{28}$ is a group $R^7$ or $R^9$ or as hereinbefore defined. This reaction is carried out in the presence of a suitable palladium catalyst well known to those skilled in the art for this type of reaction, for example bistriphenylphosphine palladium dichloride, and a catalytic amount of a cuprous halide, such as cuprous iodide. The reaction will normally be carried out in the presence of basic solvent such as diethylamine or triethylamine at a non-extreme temperature, for example between −50° and 100° and conveniently at room temperature. The starting material, i.e. the iodophenyl dithiane may be prepared as described above.

By the conversion of a group, for example a group CH=C(hal)$_2$ or (hal)CH=CH$_2$ wherein hal is chloro or bromo, into an ethynyl group.

The reaction is conveniently carried out by methods well known to those skilled in the art, for example when the group —CH=C(hal)$_2$ at about or below room temperature, for example between −70° C. and 25° C., in an inert solvent, conveniently an ether such as tetrahydrofuran.

(b) when it is desired to prepare a compound of the formula (I) from a compound of formula I which contains a group —C≡C—H, by reaction of the anion from such a compound with an alkylating or acylating agent hal $R^7$, hal $R^9$, hal $R^{17}$ or halZ respectively, wherein hal is halogen and $R^7$, $R^9$, $R^{17}$ or Z is other than hydrogen. This reaction is particularly suitable for the preparation of those compounds wherein $R^7$, $R^9$, $R^{17}$ or Z is a $C_{1-4}$ alkyl group or a group $COR^{29}$ wherein $R^{29}$ is a $C_{1-4}$ alkoxy group. The reaction is normally carried out in the presence of a strong base, such as an alkyllithium conveniently butyllithium in an inert solvent, such as an ether, for example tetrahydrofuran, at a non-extreme temperature, for example between −50° and 50° C. and conveniently between −10° and 30°. The starting material, i.e. the unsubstituted alkynylphenyl dithiane may be prepared as described above.

(c) when it is desired to prepare a compound of the formula (I) wherein $R^9$, $R^{17}$ or Z is hydrogen by the desilylation of a compound of the formula (I) wherein $R^9$, $R^{17}$ or Z is a tri-$C_{1-4}$ alkylsilyl group. This reaction may be carried out by methods well known to those skilled in the art, for example by reaction with tetrabutylammonium fluoride in an ether, such as tetrahydrofuran, at a non-extreme temperature, for example between 0° and 70° C. and conveniently at room temperature.

(d) when it is required to prepare a compound of the formula (I) wherein $R^{2b}$ is an alkylthiophenyl group by the reaction of the corresponding compound wherein $R^{2b}$ is a halophenyl group with a dialkyldisulphide in the presence of an alkyllithium compound, for example butyllithium. The alkyllithium is added to the compound of the formula (I) before the addition of the dialkyldisulphide. The reaction is carried out in the presence of an ether, such as tetrahydrofuran, at a low temperature for example between −50° and 20° C., such as −20° C.

(e) when it is required to convert a compound of the formula (I) wherein $R^{2a}$ is an axial hydrogen atom to the corresponding compound wherein $R^{2a}$ is an equatorial hydrogen atom by the addition of a strong base to the compound of the formula (I). The reaction is conveniently carried out in an inert solvent, conveniently an ether such as tetrahydrofuran, at a non-extreme temperature, conveniently −50° to 50° C. and conveniently at 0° C. followed by quenching with water. If the reaction is carried out in the presence of an alkylating agent, such as methyl iodide, the corresponding equatorial alkylated compound is formed.

(f) when it is required to prepare a compound of the formula (I) wherein $R^{2b}$ contains a hydroxyalkyl group by the reduction of the corresponding compound containing an ester group. This reduction is conveniently carried out by a complex metal hydride such as lithium aluminium hydride in an inert solvent such as an ether, for example diethyl ether, at a non-extreme temperature, for example between 0° C. and 70° C. and conveniently at room temperature.

(g) The compounds of the formula (I) may contain two or more sulphur atoms which may be oxidised if required.

Oxidations can be carried out by methods well known to those skilled in the art, for example using peracids such as peracetic acid from hydrogen peroxide and acetic acid, or 3-chloroperbenzoic acid in chloroform or dichloromethane, or using periodate such as tetrabutylammonium periodate in a halogenated hydrocarbon, for example chloroform at a non-extreme temperature, for example between 0° and 100° C. and conveniently between 10° and 30° C.

The compounds of formula (I) may be used to control pests such as arthropods, e.g. insect and acarine pests, and helminths, e.g. nematodes. Thus, the present invention provides a method for the control of arthropods and/or helminths which comprises administering to the arthropod and/or helminth or to their environment an effective amount of a compound of the formula (I). The present invention also provides a method for the control of arthropod and/or helminth infestations of animals (including humans) and/or of plants (including trees) and/or stored products which comprises administering an effective amount of a compound of the formula (I). The present invention further provides for the compounds of the formula (I) for use in human and veterinary medicine, in public health control and in agriculture for the control of arthropod and/or helminth pests.

By the term "control" is meant the amelioration in air, water, soil or foliage of present or future deleterious effects of pests and includes killing adults, larvae and eggs, the inhibition of reproduction, the repellency and/or knockdown of pests, and any other influence on behaviour.

Compounds of formula (I) are of particular value in the protection of field, forage, plantation, glasshouse, orchard and vineyard crops, of ornamentals and of plantation and forest trees, for example, cereals (such as maize, wheat, rice, millet, oats, barley, sorghum), cotton, tobacco, vegetables and salads (such as beans, cole crops, cucurbits, lettuce, onions, tomatoes and peppers), field crops (such as potato, sugar beet, ground nuts, soyabean, oil seed rape), sugar cane, grassland and forage crops (such as lucerne), plantations (such as of tea, coffee, cocoa, banana, oil palm, coconut, rubber, spices), orchards and groves (such as of stone and pip fruit, citrus fruits, kiwifruit, avocado, mango, olives and walnuts), vineyards, ornamental plants, flowers and shrubs under glass and in gardens and parks, forest trees (both deciduous and evergreen) in forests, plantations and nurseries and plants grown for industrial or pharmaceutical purposes (such as the evening primrose).

They are also valuable in the protection of timber (standing, felled, converted, stored or structural) from attack by sawflies (e.g. Urocerus) or beetles (e.g. scolytids, platypodids, lyctids, bostrychids, cerambycids, anobiids) termites (e.g. Isoptera) or other damaging pests.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

Compounds of formula (I) are of value in the control of public health pests, for example cockroaches and ants.

Compounds of formula I are also of value in the control of arthropods or helminths which are injurious to, or spread or act as vectors of diseases in man and domestic animals, for example those hereinbefore mentioned, and more especially in the control of ticks, mites, lice, fleas, midges biting, nuisance and myiasis flies, mosquitos and hemiptrean bugs.

The compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustible solid, vapourising mat, combustible coil, bait, dietary supplement, wettable powder, granule, aerosol, emulsifiable concentrate, oil suspension, oil solution, pressure-pack, impregnated article, microcapsule, pour on formulation or other standard formulations well known to those skilled in the art. Sprays may be applied by hand or by means of a spray race or arch or by vehicle or aircraft mounted apparatus. The animal, soil, plant or other surface being treated may be saturated with the spray by means of high volume application or superficially coated with the spray by means of light or ultra low volume application. Dip concentrates are not applied per se, but diluted with water and the animals immersed in a dipping bath containing the dip wash. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

Compounds of Formula (I) may be prepared either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of formula (I) in intimate admixture with a powdered solid inert carrier for example suitable clays, kaolin, bentonite, attapulgite, adsorbent carbon black, talc, mica, silica, chalk, gypsum, tricalcium phosphate, powdered cork, magnesium silicate, vegetable carriers, starch or a diatomaceous earth. Such solid formulations are generally prepared by impregnating the solid diluents with solutions of the compound of formula (I) in volatile solvents, evaporating the solvents and, if desired, grinding the products so as to obtain powders and, if desired, granulating, compacting or encapsulating the products.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 99.5% w/v of the composition and may be selected from kerosene, ketones, alcohols, xylene, aromatic naphtha, water, mineral oil, aromatic and aliphatic esters, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates, soaps, lecithins, hydrolysed glues, etc.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, or other solvents known in the art.

Wettable powders and emulsifiable concentrates will normally contain from 0.5 to 99.5% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution, they should contain the appropriate percentage of the compound of Formula (I) required for treatment.

Aerosol sprays may be prepared as a simple solution of the active ingredient in the aerosol propellant and co-solvent such as halogenated alkanes, propane, butane, dimethyl ether and the solvents referred to above, respectively. Pour-on formulations may be made as a solution or suspension of a compound of Formula (I) in a liquid medium. An arian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is polyvinyl chloride (PVC).

The concentration of the compound of formula (I) to be applied to an animal, premises, other substrates or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited will vary according to the compound chosen, the method of application, area of application, concentration of the compound in the applied formulation, factor by which the formulation is diluted and the nature of the formulation.

Undiluted formulations such as pour-on formulations in general will be applied at a concentration in the range from 0.1 to 20.0% w/w and preferably 0.1 to 10%. The amount of compound to be applied to stored products in general will lie in the range of from 0.1 to 20 ppm. Space sprays may be applied to give an average initial concentration of 0.001 to 1 mg of compound of formula (I) per cubic meter of treated space.

Compounds of formula (I) are of use in the protection and treatment of plant species, in which case an effective insecticidal, acaricidal or nematocidal amount of the active ingredient is applied to the plant or the medium in which the plant is grown. The application rate will vary according to the compound chosen, the nature of the formulation, the mode of application, the plant species, the planting density and likely infestation and other like factors but in general, a suitable use rate for agricultural crops is in the range 0.001 to 3 kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, certain compounds of formula (I) have activity against other arthropod pests including *Myzus persicae, Tetranychus urticae, Plutella xylostella, Culex* spp. *Tribolium castaneum, Sitophilus granarius, Periplaneta americana* and *Blattella germanica*. The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Ceutorhynchus, Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.), Lepidoptera (e.g. Ephestia, Mamestra, Earias, Pectinophora, Ostrinia, Trichoplusia, Pieris, Laphygma, Agrotis, Amathes, Wiseana, Tryporyza, Diatraea, Sporganothis, Cydia, Archips, Plutella, Chilo, Heliothis, Spodoptera or Tineola spp.), Diptera (e.g. Musca, Aedes, Anopheles, Culex, Glossina, Simulium, Stomoxys, Haematobia, Tabanus, Hydrotaea, Lucilia, Chrysomia, Callitroga, Dermatobia, Gasterophilus, Hypoderma, Hylemyia, Atherigona, Chlorops, Phytomyza, Ceratitis, Liriomyza and Melophagus spp.), Phthiraptera (Malophaga e.g. Damalina spp. and Anoplura e.g. Linognathus and Haematopinus spp.), Hemiptera (e.g. Aphis, Bemisia, Phorodon, Aeneolamia, Empoasca, Parkinsiella, Pyrilla, Aonidiella, Coccus, Pseudococcus, Helopeltis, Lygus, Dysdercus, Oxycarenus, Nezara, Aleurodes, Triatoma, Rhodnius, Psylla, Myzus, Megoura, Phylloxera, Adelyes, Nilaparvata, Nephrotettix or Cimex spp.), Orthoptera (e.g. Locusta, Gryllus, Schistocera or Acheta spp.), Dictyoptera (e.g. Blattella, Periplaneta or Blatta spp.), Hymenoptera (e.g. Athalia, Cephus, Atta Lasius, Solenopsis or Monomorium spp.), Isoptera (e.g. Odontotermes and Reticulitermes spp.), Siphonaptera (e.g. Ctenocephalides or Pulex spp.), Thysanura (e.g. Lepisma spp.), Dermaptera (e.g. Forficula spp.), Psocoptera (e.g. Peripsocus spp.) and Thysanoptera (e.g. *Thrips tabaci*),.

Acarine pests include ticks, e.g. members of the genera Boophilus, Ornithodorus, Rhipicephalus, Amblyomma, Hyalomma, Ixodes, Haemaphysalis, Dermacentor and Anocentor, and mites and manges such as Acarus, Tetranychus, Psoroptes, Notoednes, Sarcoptes, Psorergates, Chorioptes, Eutrombicula, Demodex, Panonychus, Bryobia and Eriophyes spp. Nematodes which attack plants and trees of importance to agriculture, forestry, horticulture, either directly or by spreading bacterial, viral, mycoplasma or fungal diseases of the plants, include root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

Compounds of the invention may be combined with one or more other pesticidally active ingredients (for example pyrethroids, carbamates, lipid amides and organophosphates) and/or with attractants, repellents, bacteriocides, fungicides, anthelmintics and the like. Furthermore, the activity of compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formulation of the invention, the ratio of synergist to compound of Formula (I) will be in the range 500:1–1:25 eg about 100:1 to 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilisers and as scavengers.

The following Examples illustrate, in a non-limiting manner, preferred aspects of the invention. All temperatures are in degrees Celsius.

EXPERIMENTAL

General Synthetic Methods and Procedures

Various compounds were synthesised and characterised in accordance with the following experimental procedures.

$^1$H N.M.R. spectra were obtained on a Bruker AM-250 or WM-300 spectrometer in deuteriochloroform solutions with tetramethylsilane (TMS) as internal standard and are expressed as ppm from TMS, number of protons, number of peaks, coupling constant $J_{Hz}$.

Mass spectra were obtained on Finnigan 4500 or Hewlett Packard 5985B instruments. Gas-liquid chromatography (g.l.c.) was performed using a Pye Unicam GCD chromatograph fitted with a 3% OV210 column on Gas-Chrom Q and a flame-ionisation detector. Progress of reactions could also be conveniently monitored on plastic sheets (40×80 mm) precoated with 0.25 mm layers of silica gel with fluorescent indicator and developed in benzene. Temperatures are in degrees Celsius throughout.

SECTION 1

Dithianes from 1,3-Dithiols

Preparation of Intermediates in Dithiane Syntheses

1. Dithiols
   (a) 2-t-Butylpropane-1,3-dithol: 2-t-Butyl-propane-1,3-diol (E. L. Eliel and Sr. M. C. Knoeber, *J. Amer. Chem. Soc.* 1968, 90, 3444) gave 2-t-butyl-1,3-propanedithiol (E. L. Eliel and R. O. Hutchins, *J. Amer. Chem. Soc.* 1969, 91, 2703)
   (b) 2-t-Butylbutane-1,3-dithiol :(c.f. E. L. Eliel et al *J. Org. Chem.*, 1975, 40, 524).
      (i) A mixture of 2-t-butylbutane-1,3-diol dimethanesulphonate (2.0g.), sulphur (0.42 g.) and hydrated sodium sulphide (3.2 g.) in dimethylformamide (50 ml.) was stirred at 20° C. for 6 days and then refluxed with stirring for 24 hours. The mixture was cooled and poured into water. The aqueous mixture was extracted with diethyl ether. The aqueous layer was acidified with hydrochloric acid and re-extracted with diethyl ether. The combined ethereal extracts were washed with water and dried over anhydrous magnesium sulfate. The solvent was removed in vacuo. 4-t-Butyl-3-methyl-1,2-dithiolane (1.2 g.) was obtained as a dark reddish oil and was used without further purification. Nuclear magnetic resonance spectrum (NMR) was as follows:
      0.90,9H,s; 1.40,3H,d,6; 1.80,1H,m; 2.80–3.40,3H,m.
      (ii) 4-t-Butyl-3-methyl-1,2-dithiolane (1.2 g.) in dry diethyl ether was added to a stirred suspension of lithium aluminium hydride (0.18 g.) in dry diethyl ether (20 ml.), under nitrogen. The mixture was refluxed, with stirring for 1 hour. The mixture was cooled and water (5 ml.) was added carefully. The mixture was acidified with 2N sulfuric acid and was then extracted with diethyl ether. The ether extracts were dried over anhydrous magnesium sulfate and the solvent was removed in vacuo.
      2-t-Butylbutane-1,3-dithiol (0.73 g.) was obtained as an amber oil and was used without further purification.
      Nuclear magnetic resonance spectrum (NMR) was as follows:
      1.00,9H,s; 1.40–1.70,5H,m; 2.80,2H,m; 3.50,1H,m.
   (c) 2-t-Butyl-2-methylpropane-1,3-dithiol: 2-t-Butyl-2-methylpropane-1,3-dithiol was prepared from 2-t-butyl-2-methylpropane-1,3-diol(ref G. Hellier et al, *J. C. S, Perk II* 1977, 612) as described in (a) above.
2. Aldehydes and Ketones Used in Dithiane Syntheses

Process A

3',5'-Dichloroacetophenone

To a suspension of magnesium turnings (2 g.) in dry ether (20 ml.), under nitrogen was added iodomethane (12 g.), in dry ether (50 ml.), at such a rate that the reaction refluxed. The addition took 1 hour. Dry benzene (150 ml.) was added and the ether blown off under a strong stream of nitrogen. 3,5-Dichlorobenzonitrile (5 g.) was dissolved in dry benzene (60 ml.) and then added dropwise over 10 minutes and the resulting mixture refluxed for 3 hrs. After cooling to 0° 6N hydrochloric acid (100 ml.), was added slowly over 10 minutes. The resulting mixture was refluxed for 6 hours.

After cooling water (50 ml.) and ether (50 ml.) were added and the mixture filtered. The aqueous phase was washed with ether (2×50 ml.), and the combined organic layers washed with sodium hydrogen carbonate solution (50 ml.), brine (50 ml.) and dried over magnesium sulphate. Evaporation yielded the title compound. Nuclear Magnetic Resonance spectrum (NMR) was as follows: 2.6, 3H, s; 7.4, 1H, m; 7.6, 2H, d.

Process B

4-Bromo-3-chlorobenzaldehyde (i) Ethyl 3-chloro-4-aminobenzoate

To a solution of ethyl 4-aminobenzoate (16 g.) in dry acetonitrile (200 ml.) at 60° was added N-chlorosuccinimide (13.35 g.) over 30 minutes. When the exothermic reaction had subsided the mixture was heated to reflux for 4 hours. After cooling the acetonitrile was removed under vacuum and the residue dissolved in dichloromethane. This was washed with 5% sodium hydroxide solution (2×100 ml.), brine and the organic layer dried over anhydrous magnesium sulphate. Evaporation yielded a solid that was purified by column chromatography on silica eluting with 10% ether/hexane.

(ii) Ethyl 4-bromo-3-chlorobenzoate

To a suspension of ethyl 3-chloro-4-aminobenzoate (9.9 g.) in hydrobromic acid (48%, 30 ml.) at 0° was added a freshly prepared solution of sodium nitrite (4.6 g.) in water (12 ml.) over 20 minutes (keeping the temperature at 0°) to form a diazonium salt.

A solution of cuprous bromide (14 g.) in hydrobromic acid (48%, 40 ml.) was heated to 50° and the diazonium salt was added as a slurry and the resulting mixture refluxed for 30 minutes. After cooling the mixture was poured onto ice/water (300 ml.) and the product extracted into ethyl acetate. The organic layer was dried over anhydrous magnesium sulphate and evaporated to give a solid.

(iii) 4-Bromo-3-chlorobenzyl alcohol

To a solution of ethyl 4-bromo-3-chlorobenzoate (1.0 g.), in dry dichloromethane at 0° was added diisobutyl aluminium hydride (7.8 g. IM solution in toluene) over 20 minutes. The mixture was stirred at 20° overnight. Saturated ammonium chloride was added until solid formed. After leaving for 30 minutes 2N hydrochloric acid was added until a solution was obtained. The mixture was extracted with ether (3×60 ml.) and the ethereal solution dried and evaporated to an oil. Nuclear Magnetic Resonance (NMR) was as follows: 2.4, 1H, t; 4.5, 2H, d; 7.0, 3H, m.

(iv) 4-Bromo-3-chlorobenzaldehyde

To a stirred solution of oxalyl chloride (4 g.) in dichloromethane (20 ml.) at −60° was added, a solution of dimethyl sulphoxide (4.6 g.), in dichloromethane (10 ml.) over 10 minutes. This was stirred for 5 minutes. A solution of 4-bromo-3-chlorobenzyl alcohol (6.5 g.) in dichloromethane (12 ml.) was then added over 10 minutes. The mixture was stirred at −60° for 30 minutes. Triethylamine (15 g.) was added and the mixture stirred and allowed to warm to 20°. Water (100 ml.) and dichloromethane (100 ml.) were added and the organic layer separated. The organic layer was washed with hydrochloric acid (2N, 2×50 ml.), saturated sodium hydrogen carbonate solution (satd) (2×50 ml.), brine (100 ml.) and dried and evaporated to give an oil. Nuclear Magnetic Resonance (NMR) was as follows. 7.6, 3H, m; 10.0, 1H, s.

By analogous methodology 3,4,5-trichlorobenzaldehyde and 2,4-bistrifluoromethylbenzaldehyde were prepared from ethyl 3,4,5-trichlorobenzoate (Reference: S. Chiavarelli *Gazz. chim. ital.*, 1955, 85, 1405) and 2,4-bistrifluoromethylbenzoic acid (supplied by Yarsley Chemical Company).

Process C

Using methodology described in stage (iv) of Process B, pent-4-ynal, hex-5-ynal, hept-6-ynal, 4-methylpentanal were prepared from pent-4-yn-1-ol (supplied by Lancaster Synthesis), hex-5-yn-1-ol (supplied by Lancaster Synthesis), hept-6-yn-1-ol (C. Crisan *Chem. Abs.* 51:5061b) and 4-methylpentan-1-ol (supplied by Aldrich) respectively.

Process D

4-Bromo-2-fluorobenzaldehyde

To a stirred mixture of glacial acetic acid (88 ml.), acetic anhydride (90 g.) and 4-bromo-2-fluorotoluene (10 g.) at −10° was added concentrated sulphuric acid (12 ml.) over 20 minutes, keeping the temperature around 0°. Solid chromium trioxide (14.7 g.) was added over 40 minutes keeping the temperature below 5°. The mixture was stirred for 15 minutes. The mixture was poured onto ice (300 g.) and stirred. The mixture was extracted with ether (2×300 ml.). The organic extracts were washed with 2% sodium carbonate solution (2×100 ml.). After evaporation the crude diacetate was treated with a mixture of water (30 ml.), ethanol (30 ml.) and conc sulphuric acid (3 ml.) and the mixture refluxed for 1 hour. After cooling the product was extracted into ether, dried and evaporated. Recrystallisation from hexane yielded the title product. Nuclear magnetic resonance (NMR) was as follows. 7.6, 3H, M; 10.0, 1H, s.

4-chloro-2-fluorobenzaldehyde and 5-chloro-2-fluorobenzaldehyde were prepared in an analogous manner from 4-chloro-2-fluorotoluene and 5-chloro-2-fluorotoluene respectively (both supplied by Lancaster Synthesis).

Process E

4-Bromo-3-trifluoromethyl acetophenone

To 4-bromo-3-trifluoromethyl aniline (8 g.) (supplied by Aldrich) in concentrated hydrochloric acid (8 ml.), water (7 ml.) and cracked ice (8 g.), was added a solution of sodium nitrite (3.4 g.) in water (5 ml.) over 30 minutes keeping the temperature below 5°. After the addition was complete, sodium acetate (2.98 g.) in water (5 ml.) was added. A mixture of acetaldoxime (2.9 g.), sodium acetate (21.7 g.), copper sulphate (1.63 g.), sodium thiosulphate (131 mg.) was prepared and cooled to 15°. The diazonium salt was added below the surface of the above mixture and the resulting mixture stirred for 1 hour and heated to reflux for 4 hours. The product was isolated by steam distillation (400 ml.) and ether extraction of the distillate. The ethereal extracts were dried over anhydrous magnesium sulphate and evaporated in vacuo. Nuclear Magnetic Resonance (NMR) spectrum was as follows: 2.6, 3H, s; 7.8, 2H, s; 8.2, 1H, s.

Process F 4-(3-Hydroxyprop-1-ynyl)acetophenone

To 4-bromoacetophenone (3 g.) in triethylamine (60 ml.) was added propargyl alcohol (1 ml.), bis-triphenylphosphinepalladium dichloride (165.6 mg.) and copper (I) iodide (66 mg.). The mixture was stirred under nitrogen overnight.

Ether was added and the mixture filtered. The filtrate was washed with water, dried over anhydrous magnesium sulphate and evaporated. The crude material was purified by column chromatography on silica eluting with ether:hexane,; 1:3. Nuclear Magnetic Resonance spectrum (NMR) was as follows: 2.6, 3H, s; 4.4, 1H, s; 7.4, 4H, dd.

4-(3-Hydroxyprop-1-ynyl)benzaldehyde, 4-(3-methoxyprop-1-ynyl)benzaldehyde and 4[3-(2-methoxyethoxy)prop-1-ynyl]benzaldehyde were prepared in an analogous manner.

Process G

4-(3-Acetoxyprop-1-ynyl)benzaldehyde

To 4-(3-hydroxyprop-1-ynyl)benzaldehyde (500 mg.) in dry benzene (20 ml.) was added acetic anhydride (326 mg.) and anhydrous sodium acetate (112 mg.). The mixture was heated at reflux for 4 hours. After cooling, water (50 ml.) was added followed by ether (50 ml.). The organic layer was separated and washed with sodium carbonate solution (2×50 ml.), washed with water, dried over anhydrous magnesium sulphate and evaporated in vacuo. The product was isolated by column chromatography on silica eluting with ether:hexane; 1:1. Nuclear Magnetic Resonance (NMR) was as follows; 2.2, 3H, s; 5.0, 2H, s; 7.5, 4H, dd; 10.0, 1H, s.

Process H

3,4,5-Trichloroacetophenone i) To a suspension of magnesium turnings (0.55 g.) in dry ether (20 ml.) was added dropwise a solution of methyl iodide (3 g.) in dry ether (10 ml.) at such a rate that the reaction refluxed. After the addition was complete, 3,4,5-trichlorobenzaldehyde (see Process B) (4 g.) was added in dry ether (10 ml.) at a rate that maintained reflux. The reaction was stirred overnight. Saturated ammonium chloride solution was added, followed by dilute hydrochloric acid. The organic layer was separated, dried over anhydrous magnesium sulphate and evaporated to give 1-(3,4,5-trichlorophenyl)ethanol. Nuclear Magnetic Resonance Spectrum (NMR) was as follows; 1.2, 3H, d; 4.2, 1H, s; 4.8, 1H, m; 7.3, 2H, s.

ii) 3,4,5-Trichloroacetophenone was prepared from 1-(3,4,5-trichlorophenyl)ethanol using methodology described in stage (iv) of Process B.

Process I

Ethyl (E)-2-methylhept-2-en-6-ynoate

Pent-4-ynal (see Process C) (1.8 g.) was added to a solution of carbethoxymethylenetriphenylphosphorane (8.6 g.) in dry chloroform (60 ml.) and the solution stirred overnight. The solvent was removed and ether added, the mixture filtered and the filtrate evaporated. Chromatography on silica eluting with ether:hexane; 1:9 yielded the product. Nuclear Magnetic Resonance spectrum (NMR) was as follows; 1.2, 3H, t; 1.8, 2H, m; 2.0, 1H, t; 2.2, 2H, m; 4.2, 2H, q.

Methyl(E)-hept-2-en-6-ynoate was prepared in an analogous manner.

Using methodology described in stages (iii) and (iv) of Process B, hept-2-en-6-ynal was prepared.

In an analogous manner 2-methylhept-2-en-6-ynal was prepared.

Process J

2-(But-3-ynylthio)acetaldehyde i) To a suspension of sodium hydride (1 g.) in dry dimethylformamide (20 ml.) at 20° was added 2-mercaptoethanol (3 g.) in dry dimethylformamide (6 ml.) over 15 minutes. The mixture was stirred for 1 hour at 80°. After cooling, but-3-yn-1-yl methanesulphonate (5.7 g.) in dry dimethylformamide (15 ml.) was added over 20 minutes. The reaction mixture was warmed at 80° for 3 hours. After cooling, the mixture was poured into water and the mixture extracted with ether (3×100 ml.). The organic layer was washed with 2N sodium hydroxide (3×50 ml.), dried over anhydrous magnesium sulphate and evaporated to give an oil. Nuclear Magnetic Resonance Spectrum (NMR) was as follows: 2.0, 1H, t; 2.0–3.0, 6H, m; 3.5, 2H, t.

ii) 2-(But-3-ynylthio)acetaldehyde was prepared from 2-(but-3-ynylthio)ethanol using methodology described in stage (iv) of Process B.

Process K

4-Ethynylcyclohexanecarboxaldehyde i) Di-isopropylamine (44.7 ml.) was dissolved in dry tetrahydrofuran (400 ml.) and cooled to −78° under nitrogen with mechanical stirring. A solution of n-butyllithium in hexane (1.6M, 197 ml.) was added. After stirring at −78° for 10 minutes a solution of dimethyl cyclohexane-1,4-dicarboxylate ((52.6 g.) Lancaster) in tetrahydrofuran (200 ml.) was added. After stirring for a further 30 minutes at −78° a solution of acetyl chloride (22.5 ml.) in tetrahydrofuran (200 ml.) was added. The reaction mixture was allowed to warm up to room temperature over a period of 3 hours. Water was then added and the mixture extracted with ether. The ethereal extracts were washed with water, saturated sodium bicarbonate solution, dilute hydrochloric acid and brine, and were then dried over anhydrous magnesium sulphate. Evaporation under reduced pressure gave a colourless oil which was slowly distilled to yield dimethyl 1-acetylcyclohexane-1,4-dicarboxylate (23.3 g, b.p. 114°–120°/0.4 mmHg). Nuclear Magnetic Resonance spectrum (NMR) was as follows: 3.89, 3H, s; 3.75, 3H, s; 2.6–1.4, 13H, m.

Infra-red spectrum (IR) (liquid film) 1740, 1710 cm$^{-1}$.

ii) Dimethyl 1-acetylcyclohexane-1,4-dicarboxylate (23.3 g.) was added to a solution of concentrated hydrochloric acid (253 ml.) in methanol (126 ml.). After refluxing for 10 hours the reaction mixture was poured into water and then extracted with dichloromethane. The organic phase was then washed with saturated sodium bicarbonate solution and brine. After drying over anhydrous magnesium sulphate the solvent was removed under reduced pressure to give methyl 4-acetylcyclohexanecarboxylate as a colourless oil. This was purified by distillation (b.p. 138°–145°/14 mmHg). Nuclear Magnetic Resonance spectrum (NMR) was as follows: 3.60, 3H, s; 2.6–1.2, 13H, m.

Infra-red spectrum (IR) (liquid film) 1730–1710 cm$^{-1}$.

iii) Methyl 4-acetylcyclohexanecarboxylate (1.0 g.) in dry pyridine (0.7 ml.) was added to a stirred mixture of phosphorus pentachloride (2.45 g.) in dry pyridine (1.4ml.). After stirring under reflux for 8 hours the reaction mixture was quenched by pouring into water. The mixture was then extracted with ether and the organic extracts washed with dilute hydrochloric acid, saturated sodium bicarbonate solution and brine. After drying over anhydrous magnesium sulphate, the solvent was removed under reduced pressure to give methyl 4-(1-chloroethenyl) cyclohexanecarboxylate as a pale yellow oil.

Nuclear Magnetic Resonance spectrum (NMR) was as follows: 5.03, 2H, s; 3.62, 3H, s; 2.80–1.09, 10H, m.

Infra-red spectrum (IR) (liquid film), 1730 cm$^{-1}$.

Mass spectrum (MS), electron impact, M+1, 203.

iv) Lithium aluminium hydride (283 mg.) was added to dry ether at 0° under a stream of nitrogen. After addition of methyl 4-(1-chloroethenyl) cyclohexanecarboxylate (1.0 g.), the reaction mixture was allowed to warm to 25° over a period of 2 hours. Sodium hydroxide solution (2.5 ml., 10%) was added cautiously. The ethereal solution was then decanted from the mixture, dried and evaporated to give 4-(1-chloroethenyl)cyclohexylmethanol.

Nuclear magnetic resonance spectrum (NMR) was as follows: 4.97, 2H, s; 3.6–3.25, 2H, m; 2.2–0.8, 10H, m.

Infra-red spectrum (IR) (liquid film), 3400 cm$^{1}$.

v) n-Butyllithium (12 ml., 1.6M) was added at 0° under nitrogen to a stirred solution of 4-(1-chloroethenyl)cyclohexylmethanol (0.84 g.) in dry tetrahydrofuran (15 ml.). The reaction mixture was allowed to warm to room temperature and was stirred at 25° for 4 hours. Ice/water (~100ml.) was then added and the reaction mixture extracted with diethyl ether. After washing the organic extracts with brine and drying over anhydrous magnesium sulphate, the solvent was removed under reduced pressure. 4-Ethynylcyclohexylmethanol was purified by column chromatography on silica (eluted with ether:hexane; 2:3).

Nuclear Magnetic Resonance spectrum (NMR) was as follows: 3.32, 2H, d; 2.80, 1H, s; 2.29–0.80, 11H, m.

Infra-red spectrum (IR) (liquid film) 3420, 3290 cm$^{-1}$.

Mass spectrum (MS), (electron impact), M+1, 139.

vi) Oxalyl chloride (354 μl.) was dissolved in dry dichloromethane (3 ml.) at −70° under nitrogen. Dimethyl sulphoxide (650 μl) in dichloromethane (3 ml.) was then added. After stirring for 5 minutes a solution of 4-ethynylcyclohexylmethanol (0.5 g.) in dichloromethane (5 ml.) was added dropwise over 5 minutes. The reaction mixture was stirred for 30 minutes at −70° before triethylamine (2.5 ml.) was added. After warming to 25° over 3 hours, water was added and the organic phase separated, washed with dilute hydrochloric acid, saturated sodium bicarbonate solution and brine, and dried. Evaporation gave 4-ethynylcyclohexanecarboxaldehyde as a colourless oil.

Nuclear magnetic resonance spectrum (NMR) was as follows: 9.61, 1H, m; 3.0–1.0, 9H, m.

Infra-red spectrum (IR) (liquid film) 3300, 2140, 1710 cm$^{-1}$.

Process L

Hex-2-ynal i) A solution of propargyl alcohol (5.6 g.) and dihydropyran (8.4 g.) in chloroform (16 ml.) was stirred in an ice-bath while a solution of phosphorus oxychloride (0.05 ml.) in chloroform (1 ml.) was added. After stirring for 2 hours at 10°–20° diethyl ether and water were added. The ethereal solution was separated and washed with water, saturated sodium carbonate solution and brine, dried over anhydrous magnesium sulphate and evaporated. Distillation yielded prop-2-ynyl tetrahydropyranyl ether (7.0 g., b.p. 68°–71°/25 mm).

ii) The above ether (2.0 g.) in dry tetrahydrofuran (15 ml.) was cooled to −78° and a 1M solution of n-butyllithium in hexane (10 ml.) was added over 10 minutes. The mixture was allowed to warm to room temperature over 3 hours and cooled to −40°. A solution of n-propyl bromide (1.3 ml.) in dry tetrahydrofuran (5 ml.) and hexamethylphosphoramide (5 ml.) was added over 5 minutes and the mixture stirred at 20° overnight. Water and ether were added and the ethereal solution separated and washed succesively with 2N hydrochloric acid, saturated sodium bicarbonate and brine, dried over anhydrous magnesium sulphate and evaporated to give an oil (1.94 g.). Treatment with methanol (10 ml.), Amberlyst '15' (270 mg,) and p-toluenesulphonic acid (10 mg.) over 2 hours at 20° followed by filtration and evaporation of the filtrate gave hex-2-yn-1-ol (1.3 g.). Nuclear Magnetic Resonance Spectrum (NMR) was as follows: 1.0, 3H,t; 1.6,4H,m; 3.6,1H,OH; 4.2,2H,m.

Hex-2-ynal was prepared from hex-2-yn-1-ol using stage (iv) of Process B. Pent-2-ynal was prepared in an analagous manner.

Process M 1,1-Diethoxy-4-methoxy-4-methylpent-2-yne

3-Methoxy-3-methylbut-1-yne (5 g.) (E. J. Corey et al *J. Org. Chem*, 1978, 43(17), 3418) was added to the Grignard reagent produced from magnesium (1.4 g.) and ethylbromide (6.5 g.) in diethyl ether (50 ml.). The solution was heated at reflux for 6 hours, cooled, and triethylorthoformate (8.49 g.) in diethyl ether (20 ml.) was added dropwise. The mixture was refluxed for 2 hours, cooled, and saturated ammonium chloride solution added. The ethereal solution was separated, washed with brine, dried over anhydrous magnesium sulphate and evaporated give an oil (3.6 g.). 1,1-Diethoxy-4-methoxy-4-methylpent-2-yne had Nuclear Magnetic Resonance (NMR) as follows: $^1$H:1.2,6H,t; 1.4,6H,s; 3.3,3H,s; 3.5,4H,q; 5.25,1H,s.

Process N 4,4-Dimethylhexanal i) Tri n-butyl tin hydride (19.6 ml.) and α-azo-iso-butyronitrile (0.5 g.) were added succesively to a stirred solution of 2-bromo-2-methylbutane (10 g.) and acrylonitrile (43.5 ml.) in dry benzene (200 ml.). The mixture was heated at reflux for 6 hours, cooled and filtered. The residue was washed with diethyl ether (50 ml.) and the combined filtrates evaporated under reduced pressure. 4,4-Dimethylhexanenitrile was obtained as a colourless liquid (2.1 g.), b.p. 85°–94°/20 mm.

ii) 4,4-Dimethylhexanal

Diisobutylaluminium hydride (1M solution in toluene, 18.5 ml.) was added to a solution of 4,4-dimethylhexanenitrile (2.0 g.) in dry diethyl ether (100 ml.) stirred under nitrogen. The mixture was refluxed for 3 hours and cooled. A solution of water (2 ml.) and dioxane (10 ml.) was added dropwise followed by dilute hydrochloric acid (80 ml.) and the solution stirred for 1 hour. Diethyl ether was added and the ethereal extracts separated. The ethereal extracts were dried (anhydrous magnesium sulphate) and evaporated to give 4,4-dimethylhexanal (1.3 g.). Nuclear Magnetic Resonance Spectrum (NMR) was as follows: 0.9,6H,s; 1.4,7H,m; 2.4,2H,m; 9.7,1H,t.

Process O

4-Bromo-3,5-dichlorobenzaldehyde i) Methyl 4-aminobenzoate (25 g.) in dry chloroform (250 ml.) was treated dropwise with sulphuryl chloride (10 ml.) and the mixture heated at reflux for 4 hours. A further supply of sulphuryl chloride (10 ml.) was added and heating continued for a further 2 hours. The reaction mixture was poured onto ice and 2N sodium hydroxide solution was added. The organic solution was separated and the aqueous phase extracted with ethyl acetate. The combined organic solution was dried (anhydrous magnesium sulphate) and evaporated to give methyl 4-amino-3,5-dichlorobenzoate as a solid.

ii) Methyl 4-amino-3,5-dichlorobenzoate (32 g.) dissolved in 48% hydrobromic acid (100 ml.) was cooled to 0° and sodium nitrite (10.5 g.) was added. The solution was added slowly to a mixture of 48% hydrobromic acid (80 ml.) and cuprous bromide (35 g.) and the mixture heated at reflux for 2 hours. After cooling, the mixture was extracted with ethyl acetate and the organic extracts washed with brine, dried (anhydrous magnesium sulphate) and evaporated to give a dark solid. Crystallisation from ethyl acetate gave methyl 4-bromo-3,5-dichlorobenzoate (20 g.). Nuclear Magnetic Resonance Spectrum (NMR) was as follows: $^1$H: 4.0,3H,s; 7.9,2H,s.

4-Bromo-3,5-dichlorobenzyl alcohol was prepared from methyl 4-bromo-3,5-dichlorobenzoate using stage (iii) of Process B and 4-bromo-3,5-dichlorobenzaldehyde using stage (iv) of Process B.

Process P

3-(1-Methylcyclopropyl)propanal i) Sodium (5.08 g.) was dissolved in dry ethanol (300 ml.). Diethyl malonate (35 g.) was added and the mixture was stirred for 2 hours. Methallyl chloride (20 g.) was added and the mixture was refluxed with stirring for 4 hours. The mixture was cooled, the solid filtered off and the solvent was removed in vacuo. 2N Hydrochloric acid solution was added and the mixture was extracted with diethyl ether. The ethereal extracts were washed with sodium hydrogen carbonate solution, water and then dried over anhydrous magnesium sulphate. The solvent was removed in vacuo. Distillation gave diethyl 2-methyl-prop-2-enylmalonate as a colourless liquid (28.2 g. b.p. 120°–126° 20 mm.).

ii) A mixture of diethyl 2-methylprop-2-enylmalonate (15 g.) and lithium chloride (6.0 g.) in dimethyl sulphoxide (100 ml.) was refluxed with stirring for 4 hours. The mixture was distilled and the distillate (185°, 760 mm) was treated with water The aqueous mixture was extracted with diethyl ether. The ethereal extracts were dried over anhydrous magnesium sulphate. The solvent was removed in vacuo and ethyl 4-methylpent-4-enoate obtained as a colourless liquid (5.34 g.)

iii) Diethylzinc (40 ml. 1.1M solution in toluene) was added dropwise to a solution of ethyl 4-methylpent-4-enoate (1.25 g.) in dry hexane (100 ml.) at −20° under nitrogen After stirring for 10 minutes diiodomethane (23.6 g.) was added dropwise and the mixture maintained at −20° for 6 hours. The mixture was allowed to warm to room temperature, aqueous ammonium chloride solution (60 ml.) added and the two layers separated. The aqueous layer was extracted with diethyl ether (3×50 ml.) and the combined organic extracts washed with sodium thiosulphate solution (50 ml.) and water (50 ml.). The extracts were dried over anhydrous magnesium sulphate and evaporated in vacuo. Chromatography on silica, eluting with diethyl ether/hexane mixtures, gave ethyl 3-(1-methylcyclopropyl)propanoate as a colourless oil (1.21 g.).

iv) Ethyl 3-(1-methylcyclopropyl)propanoate (1.2 g.) was added dropwise to a stirred suspension of lithium aluminium hydride (0.3 g.) in dry diethyl ether (80 ml.) under nitrogen. The mixture was refluxed with stirring for 1.5 hours and the mixture was cooled. Water (1.0 ml.) was added slowly and was followed by 5% sulphuric acid solution (1.0 ml.). The mixture was filtered and the filtrates dried over anhydrous magnesium sulphate. The solvent was removed in vacuo. 3-(1-Methylcyclopropyl)propan-1-ol was obtained as a colourless oil (0.73 g.).

v) 3-(1-Methylcyclopropyl)propanal was prepared from 3-(1-methylcyclopropyl)propan-1-ol using stage (iv) of Process B.

Process Q

4,4-Dimethyl-5-methoxypentanal i) 2,2-Dimethylpent-4-en-1-ol was prepared from 2,2-dimethylpent-4-enal (supplied by Aldrich) using methodology described in stage (iv) of Process P.

ii) 2,2-Dimethylpent-4-en-1-ol (4.0 g.) was added dropwise to a suspension of sodium hydride (1.13 g. 80% dispersion in oil, washed with hexane) in dry dimethylformamide (80 ml.) under nitrogen. After stirring for 1 hour, iodomethane (5.3 g.) was added dropwise and the mixture stirred for a further hour. Diethyl ether (100 ml.) was added and was followed by slow addition of water (100 ml.). The ethereal extracts were evaporated in vacuo and the residue was dissolved in hexane (50 ml.). The hexane solution was washed with water and dried over anhydrous magnesium sulphate. The solvent was removed in vacuo and 4,4-dimethyl-5-methoxypent-1-ene was obtained as a colourless oil (1.9 g.).

iii) Borane-methyl sulphide complex (2.76 ml., 2M solution in tetrahydrofuran, Aldrich) was added to 4,4-dimethyl-5-methoxypent-1-ene (1.9 g.) in dry hexane (50 ml.) under nitrogen at 0°. The mixture was stirred at 20° for 2 hours and ethanol (15 ml.) was added. 2N Aqueous sodium hydroxide solution (6.0 ml.) was then added. The mixture was cooled to 0° and hydrogen peroxide (5.3 ml., 30% aqueous solution) was added dropwise. The mixture was refluxed for 1 hour, cooled and poured into iced water (100 ml.). The aqueous mixture was extracted with diethyl ether. The ethereal extracts were washed with water and dried over anhydrous magnesium sulphate. The solvent was removed in vacuo and 4,4-dimethyl-5-methoxypentan-1-ol was obtained as a colourless oil (1.12 g).

iv) 4,4-Dimethyl-5-methoxypentanal was prepared from 4,4-dimethyl-5-methoxypentan-1-ol using methodology described in stage (iv) of Process B.

Process R

Ethyl 4-acetylcyclohexanecarboxylate

Dimethyl 1-acetylcyclohexane-1,4-dicarboxylate (see Process K) (26.5 g.) was added to a solution of concentrated hydrochloric acid (290 ml.) in ethanol (140 ml.). After refluxing for 7.5 hours, the reaction mixture was poured into water and then extracted with dichloromethane. The organic phase was then washed with saturated sodium bicarbonate solution and brine. After drying over anhydrous magnesium sulphate the solvent was removed under reduced pressure to give ethyl 4-acetylcyclohexanecarboxylate as a colourless oil. This was purified by distillation (b.p 144°–148° C./14 mm Hg.).

Process S

1-Cyclohexyl-3,3-diethoxyprop-1-yne i) Cyclohexyl methyl ketone (5.0 g.) (Lancaster Synthesis) in dry pyridine (5 ml.) was added to a mixture of phosphorus pentachloride (18.0 g.) and dry pyridine (10 ml.) in dry benzene (50 ml.) and the solution was heated at reflux for 3 hours. After cooling, the mixture was poured into iced water (100 ml.) and the resulting mixture was extracted into diethyl ether. The ethereal extracts were washed with water, dried over anhydrous magnesium sulphate and evaporated in vacuo, to give a dark oil (3.3 g.).

A solution of the crude oil in dry tetrahydrofuran (100 ml.) was stirred at 20° under a current of nitrogen. n-Butyllithium (27 ml 1.6M solution in hexane) was added and the mixture was stirred for 2 hours. Water was added and the aqueous mixture was extracted with diethyl ether. The ethereal extracts were dried over anhydrous magnesium sulphate and distilled.

Cyclohexylacetylene was obtained as a colourless liquid (1.95 g., b.p. 125°–135°, 760 mm.).

ii) Using methodology described in Process M, 1-cyclohexyl-3,3-diethoxy-prop-1-yne was prepared from cyclohexylacetylene.

Process T

4-Trifluoromethoxybenzaldehyde

Diisobutylaluminium hydride (11.8 ml. 1M solution in toluene) was added to a stirred solution of 4-cyanophenyl trifluoromethyl ether (2.0 g., Fairfield) in dry diethyl ether (100 ml.). The mixture was refluxed with stirring for 3 hours. The mixture was cooled and dioxane (5 ml.) containing water 1.0 ml.) was added. Dilute hydrochloric acid was added (60 ml. of 10% solution). The mixture was stirred for 30 minutes and extracted with diethyl ether. The ethereal extracts were washed with water and dried over anhydrous magnesium sulphate. The solvent was removed in vacuo and the residue was purified by chromatography on silica, eluting with 9:1 hexane:diethyl ether. 4-Trifluoromethoxybenzaldehyde was obtained as a colourless liquid (1.65 g.).

Process U

4-Trifluoromethylthiobenzaldehyde i) p-Toluenethiol (8 g.) was added to liquid ammonia (60 ml.) at −30°. Trifluoromethyl iodide (18 g.) was added and the mixture was irradiated with uv light (297nm.) for 30 minutes. Dry diethyl ether (35 ml.) was added and irradiation was continued for 1 hour. The mixture was allowed to warm to 20° C. and water was added. The mixture was extracted with diethyl ether and the ethereal extracts were washed with sodium thiosulphate solution and then water. The ethereal extracts were dried over anhydrous magnesium sulphate and evaporated in vacuo. Distillation gave 4-trifluoromethylthiotoluene as a mobile yellow-brown liquid (b.p. 78°–80° C., 16 mm.).

ii) A mixture of 4-trifluoromethylthiotoluene (1.5 g.), N-bromosuccinimide (1.53 g.) and benzoyl peroxide (0.05 g.) in dry carbon tetrachloride (30 ml.) was refluxed, with stirring for 4 hours. The mixture was cooled and filtered. The filtrates were evaporated in vacuo and 4-trifluoromethylthiobenzyl bromide was obtained as a crystalline solid (2.5 g.).

iii) Sodium (0.2 g.) was dissolved in dry ethanol (50 ml.). 2-Nitropropane (1.025 g.) was added and the mixture was stirred at 20° C. for 1 hour. 4-Trifluoromethylthiobenzyl bromide was added and the mixture was stirred for 24 hours. The ethanol was removed in vacuo, water was added and the mixture extracted with diethyl ether. The ethereal extracts were washed with sodium hydroxide solution (2N), water and then dried over anhydrous magnesium sulphate. The ethereal extracts were evaporated in vacuo. 4-Trifluoromethythiobenzaldehyde was obtained as a pale yellow oil (1.8 g.).

3. Methods of Preparation of Dithianes from 1,3-Dithiols

Introduction 1,3-Dithianes were prepared either by established procedures in a Dean Stark apparatus (Method I) (cf. Eliel and Knoeber; Eliel and Hutchins, loc-cit) or by forming the derivatives of the carbonyl compounds in the presence of the adduct of N,N-dimethylformamide with dimethyl sulphate (method of W. Kantlehner and H-D. Gutbrod, *Liebigs Ann, Chem.* 1979, 1362), a method established for aldehydes and some ketones with 1,3-diols, (Method II) but here shown suitable also for 1,3-dithiols. With some combinations of reagents (e.g.3',4'-dichloroacetophenone and 2-t-butylpropane-1,3- dithiol in the presence of toluene-4-sulphonic acid) reaction (Dean and Stark procedure) was shown to be complete after 4 hours and the product was isolated simply by evaporating the solvent in vacuo and eliminating the acid catalyst at the first recrystallization (e.g., from hexane). However, reaction between 4-acetylbenzonitrile and the same dithiol was incomplete after 10.5 hours with toluene-4-sulphonic acid, but nearly all the ketone had been consumed after a further 6 hour reaction following addition of Nafion-H, (Method VI) a solid perfluorinated resin sulphonic acid catalyst (see G. A. Salem, *Synthesis* 1981, 282) which then was removed for re-use by filtration. Nafion-H can be used as catalyst with other less reactive carbonyl compounds.

The procedure of Kantlehner and Gutbrod (loc. cit.) was particularly suitable for smaller scale preparations (50–200 mg.) and with potentially less stable compounds. Most such reactions required 48 hours at room temperature and if phases separated initially or during reaction, sufficient dichloromethane was added, at intervals if necessary, to maintain a homogenous reaction medium.

Carboxylic acids are also a useful source of dithianes (see Method IV).

Method I

5

(e)-t-Butyl-2(e)-(3-trifluoromethylphenyl)-1,3-dithiane

A mixture of 3-trifluoromethylbenzaldehyde (2.24 g., 13 mmol), 2-t-butyl- propane-1,3-dithiol (1.75 g. 10 mmole) and p-toluenesulphonic acid (50 mg.) in benzene (100 ml.) was refluxed in a Dean and Stark apparatus for 6 hours. After cooling the mixture was poured into water and the aqueous mixture was extracted with diethyl ether. The organic extracts were washed with water, dried over anhydrous magnesium sulphate and evaporated in vacuo. The residue was recrystallised from hexane and 5(e)-t-butyl-2(e)-(3-trifluoromethylphenyl)-1,3-dithiane was obtained as a colourless crystalline solid (1.4 g.).

25

Further compounds were prepared using analogous methodology commencing from appropriate starting materials; these compounds and their physical and chemical characteristics are listed in Tables 1A, 1B, 2 and 3.

Method II

2-(4-Ethynylphenyl)-5-t-butyl-1,3-dithiane

A mixture of 4-ethynylbenzaldehyde (131 mg., 1.00 mmol.), 2-t-butylpropane-1,3-dithiol (206 mg., 1.25 mmole) (E. L. Eliel and R. O. Hutchins (*J. Amer. Chem. Soc.* 1969, 91, 2703)) and the adduct of N,N-dimethylformamide and dimethyl sulphate (300 mg., 1.50 mmole) diluted with methylene chloride (2.0 ml.) was maintained at 23° for 48 hours. After cooling to 0°, triethylamine (0.2 ml) was added, and the solution was washed with water (3×2 ml.) which was again extracted with methylene chloride. The combined organic layers were dried (anhydrous magnesium sulphate) and evaporated to give a residue (320 mg.) which was recrystallized from hexane (2.5 ml.) to give 2-(4-ethynylphenyl)-5-t-butyl-1,3-dithiane, m.p. 149°, (120 mg, 43%)

Further compounds were prepared using analogous methods commencing from appropriate starting materials; these compounds and their physical and chemical characteristics are listed in Tables 1A, 2 and 3.

Method III

5(e)-t-Butyl-2(e)-(3,3-dimethylbut-1-ynyl)-1,3-dithiane

Boron trifluoride etherate (1.73 ml.) was added to a solution of acetic acid (4 ml.) in chloroform (8 ml.) stirred under nitrogen and heated to reflux. A solution of 2-t-butylpropane-1,3-dithiol (2.46 ml.) and 4,4-dimethylpent-2-ynal diethylacetal (2.6 g.) in chloroform (20 ml.) was added dropwise over 30 minutes and heating continued for a further 1 hour. After cooling, water was added and the mixture separated. The organic phase was washed with 10% sodium hydroxide solution, brine, dried over anhydrous magnesium sulphate and evaporated. Chromatography on silica, eluting with hexane yielded the product which crystallised from hexane (yield: 400 mg.). Further compounds were prepared using analogous methods commencing from appropriate starting materials; these compounds and their physical and chemical characteristics are listed in Tables 1A, 2 and 3.

Method IV

E-5(e)-t-Butyl-2(e)-(3,3-dimethylbut-1-enyl)-1,3-dithiane

A solution of stannous chloride (0.74 g.) and E-4,4-dimethylpent-2-enoic acid (0.5 g) in dry tetrahydrofuran (10 ml.) was stirred under nitrogen while a 0.2M solution of 5-1-butyl-1,3,2-dithiaborinanedimethylsulphide complex in tetrahydrofuran (33.2 ml.) [*J. Org. Chem.*, 1987, 52(10), 2114] was added. The solution was stirred at room temperature for 20 hours when 10% potassium hydroxide (10 ml.) solution and diethyl ether were added. The ethereal solution was separated, dried (anhydrous magnesium sulphate), and evaporated under reduced pressure to give an oil. Chromatography on silica eluting with hexane yielded E-5(e)-t-butyl-2(e)-(3,3-dimethylbut-1-enyl)-1,3-dithiane (30 mg.).

Method V

To the dithiol (about 1.0 ml.) weighed accurately into a 10 ml. stoppered flask, was added an equivalent proportion plus ca 10% of aldehyde (usually measured by volume), followed by formic acid (5 ml., 95–97%). The reaction mixture was then stoppered firmly and stirred from 2–18 hours. If solid separated, water was added and the product was collected by filtration, dried and recrystallised from hexane. For non-solid products, the formic acid layer was separated from the oil, diluted with 10 ml. ice/water, and extracted twice with dichloromethane. The organic layers were combined, washed with saturated sodium hydrogen carbonate solution until no more carbon dioxide was evolved, and with saturated sodium chloride, and dried over anhydrous magnesium sulphate. After evaporating the solvent, the residue was distilled at 0.2–0.5 m.m. Hg to give 1.0–1.3 g. of product. Further compounds were prepared using analogous methods commencing from appropriate starting materials; these compounds and their physical and chemical characteristics are listed in Tables 1A, 2 and 3.

Method VI

Reaction between 4-acetylbenzonitrile and 2-t-butylpropane-1,3-dithiol (as described in Method I) was incomplete after 10.5 hours with toluene-4-sulphonic acid, but nearly all the ketone had been consumed after a further 6 hour reaction following addition of Nafion-H, a solid perfluorinated resin sulphonic acid catalyst (see G. A. Salem, *Synthesis* 1981, 282) which then was removed for re-use by filtration.

TABLE 1A

Structures and Synthetic Methods for Dithianes

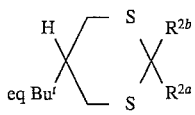

Prepared from 2-t-Butylpropane-1,3-dithiol

| Compound No. | $R^{2a,b}$ | Isomer Ratio (i):(ii) | Starting Material | Method of Dithiane Synthesis |
|---|---|---|---|---|
| 1 | eq. 4-Bromophenyl; ax. H | | 4-Bromobenzaldehyde[1] | I |
| 2 | eq. 4-Chlorophenyl; ax. H | | 4-Chlorobenzaldehyde[1] | I |
| 3 | eq. 4-Iodophenyl; ax. H | | 4-Iodobenzaldehyde[3] | I |
| 4 | eq. 4-Ethynylphenyl; ax. H | | 4-Ethynylbenzaldehyde[4] | II |
| 5 | i) eq. 4-Bromophenyl; ax. Me<br>ii) ax. 4-Bromophenyl; eq. Me | 2:1 | 4-Bromoacetophenone[1] | I |

TABLE 1A-continued

Structures and Synthetic Methods for Dithianes

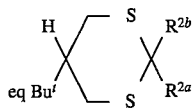

Prepared from 2-t-Butylpropane-1,3-dithiol

| Compound No. | $R^{2a,b}$ | Isomer Ratio (i):(ii) | Starting Material | Method of Dithiane Synthesis |
|---|---|---|---|---|
| 6 | eq. 4-(2-Trimethylsilylethynyl)phenyl; ax. H | | 4-(2-Trimethylsilylethynyl)-benzaldehyde[4] | II |
| 7 | eq. 4-Bromophenyl; ax. Et | | 4-Bromopropiophenone[1] | II |
| 8 | eq. 4-Ethynylphenyl; ax. Me | | 4-Ethynylacetophenone[5] | II |
| 9 | i) eq. 3,4-Dichlorophenyl; ax. H<br>ii) ax. 3,4-Dichlorophenyl; eq. H | 5:3 | 3,4-Dichlorobenzaldehyde[1] | II |
| 10 | eq. 4-Cyanophenyl; ax. H | | 4-Cyanobenzaldehyde[1] | II |
| 11 | i) eq. 4-Cyanophenyl; ax. Me<br>ii) ax. 4-Cyanophenyl; eq. Me | 2:5 | 4-Cyanoacetophenone[1] | VI |
| 12 | eq. 3,4-Dichlorophenyl; ax. Me | | 3,4-Dichloroacetophenone[1] | II |
| 13 | ax. 3,4-Dichlorophenyl; eq. Me | | | |
| 14 | eq. 4-Bromophenyl; ax. Me | | 4-Bromoacetophenone[1] | I |
| 15 | eq. 3-Trifluoromethylphenyl; ax. H | | 3-Trifluoromethylbenzaldehyde[1] | I |
| 17 | eq. 3,3-Dimethylbut-1-ynyl; ax. H | | 4,4-Dimethylpent-2-nyal[6] | I |
| 18 | eq. Trimethylsilylethynyl; ax. H | | 3-Trimethylsilylpropynal[7] | I |
| 19 | eq. 3,3-Dimethylbut-1-ynyl, ax. Me | | 5,5-Dimethylhex-3-yn-2-one[8] | I |
| 20 | i) eq. 3,4-Dichlorophenyl; ax. Me<br>ii) ax. 3,4-Dichlorophenyl; eq. Me | 2:3 | 3,4-Dichloroacetophenone[1] | I |
| 21 | eq. 3-Trifluoromethylphenyl; ax. Me | | 3-Trifluoromethylacetophenone[2] | I |
| 22 | ax. 3-Trifluoromethylphenyl; eq. Me | | | |
| 23 | ax. 4-Bromophenyl; eq. Me | | 4-Bromoacetophenone[1] | I |
| 25 | ax. 3,5-Dichlorophenyl; eq. Me | | 3,5-Dichloroacetophenone[2] | I |
| 26 | eq. 3,5-Dichlorophenyl; ax. Me | | | |
| 27 | i) eq. 2,4-Dichlorophenyl; ax. Me<br>ii) ax. 2,4-Dichlorophenyl; eq. Me | 1:6 | 2,4-Dichloroacetophenone[2] | I |
| 28 | ax. 4-Trifluoromethylphenyl; eq. Me | | 4-Trifluoromethylacetophenone[2] | I |
| 29 | eq. 4-Trifluoromethylphenyl; ax. Me | | | |
| 30 | eq. 4-Bromo-2-fluorophenyl; ax. H | | 4-Bromo-2-fluorobenzaldehyde (prepared by Process D) | I |
| 31 | eq. 4-Trifluoromethylphenyl; ax. H | | 4-Trifluoromethylbenzaldehyde[2] | I |
| 32 | ax. 3,5-Bistrifluoromethylphenyl; eq. Me | | 3,5-Bistrifluoromethylacetophenone[1] | I |
| 33 | eq. 3,5-Bistrifluoromethylphenyl; ax. Me | | | |
| 34 | eq. 3,5-Bistrifluoromethylphenyl; ax. H | | 3,5-Bistrifluoromethyl-benzaldehyde[1] | I |
| 35 | eq. 3,4,5-Trichlorophenyl; ax. H | | 3,4,5-Trichlorobenzaldehyde (Prepared by Process B) | I |
| 36 | ax. 4-Bromo-3-trifluoromethylphenyl; eq. Me | | 4-Bromo-3-trifluoromethylacetophenone (Prepared by Process E) | I |
| 37 | eq. 4-Bromo-3-trifluoromethylphenyl; ax. Me | | | |
| 38 | i) eq. 4-(3-Hydroxyprop-1-ynyl)phenyl; ax. Me<br>ii) ax. 4-(3-Hydroxyprop-1-ynyl)phenyl; eq. Me | 1:4 | 4-(3-Hydroxyprop-1-ynyl)-acetophenone (Prepared by Process F) | I |
| 39 | eq. 4-(3-Hydroxyprop-1-ynyl)phenyl; ax. Me | | 4-(3-Hydroxyprop-1-ynyl)-acetophenone (Prepared by Process F) | I |
| 40 | eq.4-Bromo-3-chlorophenyl; ax. H | | 4-Bromo-3-chlorobenzaldehyde (Prepared by Process B) | I |
| 41 | eq. 2,4-Dichlorophenyl; ax. H | | 2,4-Dichlorobenzaldehyde[1] | I |
| 42 | eq, 3,5-Dichlorophenyl; ax. H | | 3,5-Dichlorobenzaldehyde[1] | I |
| 43 | eq. 4-Methoxyphenyl; ax. H | | 4-Methoxybenzaldehyde[1] | I |
| 44 | eq. 2,3,4,5,6-Pentafluorophenyl; ax. H | | 2,3,4,5,6-Pentafluorobenz-aldehyde[1] | I |
| 47 | i) eq. 4-Bromo-3,5-dichlorophenyl; ax. H<br>ii) ax. 4-Bromo-3,5-dichlorophenyl; eq. H | 2:1 | 4-Bromo-3,5-dichlorobenz-aldehyde (Prepared by Process O) | I |
| 49 | eq. 2,3,4,5,6-Pentafluorophenyl; ax. Me | | | |

TABLE 1A-continued

Structures and Synthetic Methods for Dithianes

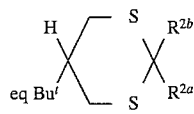

Prepared from 2-t-Butylpropane-1,3-dithiol

| Compound No. | $R^{2a,b}$ | Isomer Ratio (i):(ii) | Starting Material | Method of Dithiane Synthesis |
|---|---|---|---|---|
| 50 | ax. 2,3,4,5,6-Pentafluorophenyl; eq. Me | | 2,3,4,5,6-Pentafluoroacetophenone[1] | I |
| 51 | eq. 2-Fluoro-4-trifluoromethylphenyl; ax. H | | 2-Fluoro-4-trifluoromethyl-benzaldehyde[9] | I |
| 52 | eq. 4-(3-Hydroxyprop-1-ynyl)phenyl; ax. H | | 4-(3-Hydroxyprop-1-ynyl)-benzaldehyde (Prepared by Process F) | I |
| 53 | eq. 4-(3-Acetoxyprop-1-ynyl); ax. H | | 4-(3-Acetoxyprop-1-ynyl)-benzaldehyde (Prepared by Process G) | I |
| 55 | eq. 5-Chloro-2-fluorophenyl; ax. H | | 5-Chloro-2-fluorobenzaldehyde (Prepared by Process D) | I |
| 56 | eq. 3,4,5-Trichlorophenyl; ax. Me | | 3,4,5-Trichloroacetophenone (Prepared by Process H) | I |
| 57 | ax. 3,4,5-Trichlorophenyl; eq. Me | | | I |
| 58 | ax. 2,4-Bistrifluoromethylphenyl; eq. H | | 2,4-Bistrifluoromethyl-benzaldehyde (Prepared by Process B) | I |
| 59 | eq. 4-[3-(2-Methoxyethoxy)prop-1-ynyl]phenyl; ax. H | | 4-[3-(2-Methoxyethoxy)prop-1-ynyl]benzaldehyde | I |
| 60 | eq. 4-(3-Methoxyprop-1-ynyl)phenyl; ax. H | | 4-(3-Methoxyprop-1-ynyl)-benzaldehyde (Prepared by Process F) | I |
| 61 | i) eq. 4-(Trimethylsilylethynyl)phenyl; ax. Me ii) ax. 4-(Trimethylsilylethynyl)phenyl; eq. Me | 9:1 | 4-(Trimethylsilylethynyl)-acetophenone[5] | I |
| 62 | ax. 4-Ethynylphenyl; eq. Me | | 4-Ethynylacetophenone[5] | II |
| 63 | ax. 4-(Trimethylsilylethynyl)phenyl; eq. Me | | 4-(Trimethylsilylethynyl)-acetophenone[5] | I |
| 69 | i) eq. Pent-1-ynyl; ax. H ii) ax. Pent-1-ynyl; eq. H | 2:1 | Hex-2-ynal (Prepared by Process L) | I |
| 70 | ax. Prop-1-ynyl; eq. H | | 2-Butyn-1-al diethyl acetal[1] | III |
| 71 | eq. Prop-1-ynyl; ax. H | | | III |
| 72 | ax. Pent-1-ynyl; eq. H | | Hex-2-ynal (Prepared by Process L) | III |
| 73 | ax. E-Hex-1-en-5-ynyl; eq. H | | Hept-2-en-6-ynal (Prepared by Process I) | I |
| 74 | eq. E-Hex-1-en-5-ynyl; ax. H | | | I |
| 75 | i) eq. Pent-4-ynyl; ax. H ii) ax. Pent-4-ynyl; eq. H | 1:1 | Hex-5-ynal (Prepared by by Process C) | I |
| 76 | eq. Hex-5-ynyl; ax. H | | Hept-6-ynal (Prepared by Process C) | I |
| 79 | i) eq. But-1-ynyl; ax. H ii) ax. But-1-ynyl; eq. H | 2:3 | Pent-2-ynal (Prepared by Process L) | I |
| 82 | eq. 3,3,3-Trichloroprop-1-enyl; ax. H | | 4,4,4-Trichlorobut-2-en-1-al diethyl acetal[10] | III |
| 83 | eq. 3,3,-Trichloropropyl; ax. H | | 2-Bromo-4,4-dimethylpentanal diethyl acetal[11] | III |
| 84 | eq. 1-Bromo-3,3,3-trichloroprop-1-enyl; ax. H | | 2-Bromo-4,4,4-trichloro-butenal diethyl acetal[10] | III |
| 85 | eq. 3,3,3-Trichloroprop-1-ynyl; ax. H | | 4,4,4-Trichlorobutynal diethyl acetal[10] | III |
| 86 | eq. 3,3,3-Trichloropropyl; ax. Me | | 5,5,5-Trichloropentan-2-one[12] | I |
| 87 | eq. 2-Hydroxy-3,3,3-Trichloropropyl; ax. Me | | 5,5,5-Trichloro-3,4-epoxy-pentan-2-one[13] | III |
| 88 | eq. 3-Methoxy-3-methylbut-1-ynyl; ax. H | | 1,1-Diethoxy-4-methoxy-4-methylpent-2-yne (Prepared by Process M) | III |
| 89 | i) eq. Cyclohexylethynyl; ax. H | | 1-Cyclohexyl-3,3-diethoxy- | III |

TABLE 1A-continued

Structures and Synthetic Methods for Dithianes

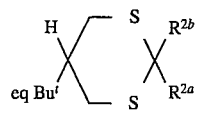

Prepared from 2-t-Butylpropane-1,3-dithiol

| Compound No. | $R^{2a,b}$ | Isomer Ratio (i):(ii) | Starting Material | Method of Dithiane Synthesis |
|---|---|---|---|---|
| | ii) ax. cyclohexylethynyl; eq. H | | prop-1-yne (See Process S) | |
| 90 | ax. 4-Bromophenyl; eq. Et | | 4-Bromopropiophenone[1] | I |
| 91 | i) eq. 3-Methylbutyl; ax. H | 5:4 | 4-Methylpentanal (Prepared by Process C) | V |
| | ii) ax. 3-Methylbutyl; eq. H | | | |
| 92 | i) eq. n-Pentyl; ax. Me | 10:7 | Heptan-2-one[1] | V |
| | ii) ax. n-Pentyl; eq. Me | | | |
| 93 | i) eq. 2-Methylpropyl; ax. H | 10:7 | 3-Methylbutanal[1] | V |
| | ii) ax. 2-Methylpropyl; eq. H | | | |
| 94 | i) eq. 3-Methylbutyl; ax. Me | 2:1 | 5-Methylhexan-2-one[1] | V |
| | ii) ax. 3-Methylbutyl; eq. Me | | | |
| 95 | i) eq. 1-Butylethenyl; ax. Me | 1:1 | 2-n-Butylacrolein[2] | V |
| | ii) ax. 1-Butylethenyl; eq. Me | | | |
| 96 | i) eq. heptyl; ax. | 1:1 | n-Octanal[1] | V |
| | ii) ax. heptyl; eq. H | | | |
| 97 | i) eq. Pentyl; ax. H | 1:1 | n-Hexanal[1] | V |
| | ii) ax. Pentyl; eq. H | | | |
| 98 | i) eq. 4-Methylpent-3-en-1-yl; ax. Me | 1:1 | 6-Methylhept-5-en-2-one[1] | V |
| | ii) ax. 4-Methylpent-3-en-1-yl; eq. Me | | | |
| 99 | i) eq. 2,6-Dimethylhepta-1,5-dienyl; ax. H | 1:1 | E-3,7-Dimethylocta-2,6-dienal[1] | V |
| | ii) ax. 2,6-Dimethylhepta-1,5-dienyl; eq. H | | | |
| 100 | i) eq. Pent-1-enyl; x. H | 1:1 | Hex-2-enal[1] | V |
| | ii) ax. Pent-1-enyl; eq. H | | | |
| 101 | i) eq. Penta-1,3-dienyl; ax. H | 1:1 | Hexa-2,4-dienal[1] | V |
| | ii) ax. Penta-1,3-dienyl; eq. H | | | |
| 102 | eq. Trans-4(e)-Ethynylcyclohexyl; ax. H | | trans-4-Ethynylcyclohexanecarboxaldehyde | I |
| 103 | ax. Trans-4(e)-Ethynylcyclohexyl; eq. H | | (Prepared by Process K) | |
| 104 | eq. Cyclohexyl; ax. H | | Cyclohexanecarboxaldehyde[1] | I |
| 105 | eq. 3-(6-Chloropyridyl); ax. H | | 6-Chloropyridyl-3-carboxaldehyde[14] | I |
| 106 | ax. 3-(6-Chloropyridyl); eq. H | | | I |
| 107 | i) eq. 2,2-Dichloro-3,3-dimethylcyclopropyl; ax. H | 1:2 | 2,2-Dichloro-3,3-dimethyl-cyclopropanecarboxaldehyde[15] | I |
| | ii) ax. 2,2-Dichloro-3,3-dimethylcyclopropyl; eq. H | | | |
| 108 | eq. 3,3-Dimethylbutyl; ax. H | | 4,4-Dimethylpentanal[16] | I |
| 109 | i) eq. 3,3-Dimethylbutyl; ax. H | 1:1 | 4,4-Dimethylpentanal[16] | I |
| | ii) ax. 3,3-Dimethylbutyl; eq. H | | | |
| 110 | eq. 3,3-Dimethylbut-1-enyl; ax. H | | E-4,4-Dimethylpent-2-enoic acid[17] | IV |
| 111 | i) eq. 2,2-Dimethylpropyl; ax. H | 7:3 | 3,3-Dimethylbutanoic acid[1] | IV |
| | ii) ax. 2,2-Dimethylpropyl; eq. H | | | |
| 112 | i) eq. 2,2-Dimethylpropyl; ax. Me | 3:2 | 4,4-Dimethylpentan-2-one[1] | I |
| | ii) ax. 2,2-Dimethylpropyl; eq. Me | | | |
| 113 | i) eq. But-3-ynylthiomethyl; ax. H | 3:2 | 2-(But-3-yn-1-ylthio)acetaldehyde (Prepared by Process J) | |
| | ii) ax. But-3-ynylthiomethyl; eq. H | | | |
| 114 | eq. E-1-Methylhex-1-en-5-ynyl; ax. H | | E-2-Methylhept-2-en-6-ynal (Prepared by Process I) | I |
| 116 | i) eq. 3,3-Dimethyl-4-methoxybutyl; ax. H | | 4,4-Dimethyl-5-methoxy- | I |

TABLE 1A-continued

Structures and Synthetic Methods for Dithianes

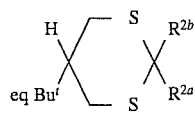

Prepared from 2-t-Butylpropane-1,3-dithiol

| Compound No. | $R^{2a,b}$ | Isomer Ratio (i):(ii) | Starting Material | Method of Dithiane Synthesis |
|---|---|---|---|---|
| | ii) ax. 3,3-Dimethyl-4-methoxybutyl; eq. H | 3:5 | pentanal (Prepared by Process Q) | |
| 117 | i) eq. 2-(1-Methylcyclopropyl)ethyl; ax. H | 1:1 | 3-(1-methylcyclopropyl)- | I |
| | ii) ax. 2-(1-Methylcyclopropyl)ethyl; eq. H | | propanal (Prepared by Process P) | |
| 118 | i) eq. 3,3-Dimethylpentyl; ax. H | 4:3 | 4,4-Dimethylhexanal | I |
| | ii) ax. 3,3-Dimethylpentyl; eq. H | | (Prepared by Process N) | |
| 119 | eq. 3,3-Dimethylpentyl; ax. H | | 4.4-Dimethylhexanal (Prepared by Process N) | I |
| 128 | 4-Ethoxycarbonylcyclohexyl; Me | | Ethyl 4-acetylcyclohexane- carboxylate Prepared by Process R) | I |
| 129 | eq. 2-Chloro-4-fluorophenyl; ax. H | | 2-chloro-4-fluorobenzaldehyde (Prepared by Process D) | I |
| 130 | i) eq. 4,4-Dimethylpent-2-yl; ax. H | 20:1 | 2,4,4-Trimethylpentanal | I |
| | ii) ax. 4,4-Dimethylpent-2-yl; eq. H | | (Prepared by Process C) | |
| 131 | i) E-eq. 3,3-DImethylbut-1-enyl; ax. H | 2:1 | E-4,4-Dimethylpent-2-enoic | IV |
| | ii) E-ax. 3,3-Dimethylbut-1-enyl; eq. H | | acid[17] | |
| 132 | i) eq. 2,3,3-Trimethylbutyl; ax. H | 3:2 | 3,4,4-Trimethylpentanoic | IV |
| | ii) ax. 2,3,3-Trimethylbutyl; eq. H | | acid[1] | |
| 133 | eq. 4-Methoxycarbonylphenyl; ax. H | | Methyl 4-formylbenzoate[1] | V |
| 134 | i) eq. 3-Methylbut-1-enyl; ax. Me | 1:2 | 5-Methylhex-3-en-2-one[1] | |
| | ii) ax. 3-Methylbuty-1-enyl; eq. Me | | | |
| 141 | i) eq. trans-4(e)-Ethynylcyclohexyl; ax. H | 1:1 | trans-4-Ethynylcyclohexanecarboxaldehyde | I |
| | ii) ax. trans-4(e)-Ethynylcyclohexyl; eq. H | | (Prepared by Process K) | |
| 143 | eq. 4-Trifluoromethoxyphenyl; ax. H | | 4-Trifluoromethoxybenzalde- hyde (Prepared by Process T) | I |
| 144 | eq. 4-Trifluoromethylthiophenyl; ax. H | | 4-Trifluoromethylthiobenzalde- hyde (Prepared by Process U) | I |

TABLE 1B 4 and 5-Methylated Dithianes

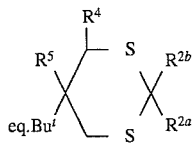

| Compound No. | $R^{2a,b}$ | $R^4$ | $R^5$ | Starting Material | Method of Dithiane Synthesis |
|---|---|---|---|---|---|
| 16 | eq. 4-Bromophenyl; ax. H. | ax. Me | ax. H | 4-Bromobenzaldehyde[1] | I |
| 65 | eq. 4-Bromophenyl; ax. H | H | ax. Me | 4-Bromobenzaldehyde[1] | I |
| 66 | ax. 4-Bromphenyl; eq. H | H | ax. Me | 4-Bromobenzaldehyde[1] | I |
| 67 | ax. 4-Bromophenyl; eq. Me | H | ax. Me | 4-Bromoacetophenone[1] | I |
| 68 | eq. 4-Bromophenyl; ax. Me | H | ax. Me | 4-Bromoacetophenone[1] | I |
| 115 | eq. 3,3-Dimethylbutyl; ax. H | H | ax. Me | 4,4-Dimethylpentanal[16] | I |
| 135 | 4-Bromophenyl; H | Me | H Mixture of isomers | 4-Bromobenzaldehyde[1] | I |
| 136 | 4-Bromophenyl; Me | Me | H Mixture of isomers | 4-Bromoacetophenone[1] | I |
| 137 | 3,4-Dichlorophenyl; Me | Me | H Mixture of isomers | 3,4-Dichloroacetophenone[1] | I |
| 138 | 4-Bromophenyl; Me | H | ax. Me | 4-Bromoacetophenone[1] | I |

TABLE 1B-continued

4 and 5-Methylated Dithianes

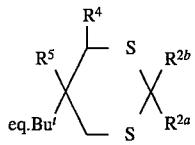

| Compound No. | $R^{2a,b}$ | $R^4$ | $R^5$ | Starting Material | Method of Dithiane Synthesis |
|---|---|---|---|---|---|
| | | | | Mixture of isomers | |

[1] Aldrich
[2] Lancaster Synthesis
[3] Beilstein 7 241
[4] W. B. Austin, N. Bilow, W. J. Kelleghan and K. S. Y. Lau J. Org. Chem 1981, 46, 2280.
[5] S. Takahashi, Y. Kuroyama, K. Sonogashira and N. Hagihara Synthesis 1980, 627.
[6] F. Bohlmann Chem. Ber 1953, 86, 63.
[7] N. V. Komarov, O. G. Yarosh and L. N. Astaf'eva (C.A. 65:10607d), Zh. Obshch. Khim 1966, 36, 407.
[8] J. W. Wilson and V. S. Stubblefield J. Amer. Chem. Soc. 1968, 40, 3423.
[9] Yarsley
[10] A. Le Coq and E. Levas C. R. Acad. Sc. Paris C 1968, 266, 723.
[11] A. Le Coq and E. Levas C. R. Acad. Sc. Paris C 258 (16), 4085.
[12] U. K. Patent, 1,503,049.
[13] R. E. Bowman et al J. Chem. Soc. (C), 1970, 94.
[14] U. K. Patent, GB 2,002, 368.
[15] German Patent, DOS 3,309,654.
[16] R. Quelet, P. Bercot and J. d'Angelo Comp. Rend. 1965, 260(4) 1191.
[17] E. L. Foreman and S. M. McElvain J. Amer. Chem. Soc. 1940, 62, 1435.

SECTION II

Dithianes Prepared from Dithiane Precursors

Example 1

Methyl 3 -[4-(5(e)-t-butyl-1,3-dithian-2(e)-yl)phenyl]prop-2-ynoate

To N-isopropylcyclohexylamine (113 μl.) in dry tetrahydrofuran (8 ml.) under nitrogen at 0° was added n-butyl lithium (1.6M) (431 μl) over 5 minutes. The mixture was stirred at 0° for 20 minutes and then cooled to −70°. A solution of 5(e)-t-butyl-2(e)-(4-ethynyl)phenyl-1,3-dithiane (200 mg.) in tetrahydrofuran (6 ml.) was added over 5 minutes. The mixture was stirred for a further 10 minutes at −70°. Methyl chloroformate (70 μl.) was added neat to the reaction mixture and the reaction stirred at 20° overnight. The reaction mixture was poured into water and the aqueous mixture extracted with ether (2×25 ml.). The ethereal extracts were dried over anhydrous magnesium sulphate. Evaporation of the ethereal extracts yielded a solid which was purified by chromatography on silica eluting with ether:hexane; 1:4.

Example 2

5-t-Butyl-2(e)-(4-prop-1-ynylphenyl)-1,3-dithiane 5-t-Butyl-2(e)-(4-iodophenyl)-1,3-dithiane (0.19 g) was stirred in dry diethylamine (20 ml) with bis-triphenylphosphinepalladium dichloride (~20 mg) and cuprous iodide (~8 mg) until solution was complete, then propyne was passed into the mixture for 1 hour. The flask was then stoppered and stirring continued for 3 hours. After concentration the residue was dissolved in dichloromethane and washed with water (2×10 ml). The washings were extracted with dichloromethane and the combined organic layers were dried over anhydrous magnesium sulphate and concentrated. The product was purified by chromatography on silica eluting with hexane: dichloromethane; 1:1 and recrystallised from hexane-benzene (0.117 g).

In an analogous manner 5(e)-t-butyl-2(e)-(2-fluoro-4-trimethylsilylethynylphenyl)-1,3-dithiane and 5(e)-t-butyl-2(e)-(3-fluoro-4-trimethylsilylethynylphenyl)-1,3-dithiane were prepared from trimethylsilylacetylene and 5(e)-t-butyl-2(e)-(2-fluoro-4-iodophenyl)-1,3-dithiane and 5(e)-t-butyl-2(e)-(3-fluoro-4-iodophenyl)-1,3-dithiane respectively.

Example 3

5(e)-t-Butyl-2(e)-(2-fluoro-4-ethylphenyl)-1,3-dithiane

5(e)-t-Butyl-2(e)-(2-fluoro-4-trimethylsilylethynylphenyl)-1,3-dithiane (0.146 g) was dissolved in dry tetrahydrofuran (20 ml) under nitrogen. A solution of 1M n-tetrabutylammonium fluoride in tetrahydrofuran (0.7 ml) was added and the mixture stirred for 1.5 hours. The solvent was removed in vacuo. Crystallisation from hexane gave the above compound as a white solid (0.12 g).

By the above methodology the following compounds were prepared:
5(e)-t-Butyl-2(e)-(3-fluoro-4-ethynylphenyl)-1,3-dithiane.
5(e)-t-Butyl-2(a)-ethynynyl-2(e)-methyl-1,3-dithiane.
5(e)-t-Butyl-2(e)-(4-ethynylphenyl)-2(a)-methyl-1,3-dithiane.
5(e)-t-Butyl-2(a)-(4-ethynylphenyl)-2(e)-methyl-1,3-dithiane.

Example 4

5(e)-t-Butyl-2(e)-(4-ethynylphenyl)-1,3-dithiane 1-oxide

A solution of 5(e)-1-butyl-2(e)-(4-ethynylphenyl)-1,3-dithiane (280 mg.) and n-tetrabutylammonium periodate (440 mg.) in dry chloroform (10 ml.) was heated at reflux, under nitrogen, for 12 hours. Water was added and the solutions separated. The organic solution was washed with brine, dried (anhydrous magnesium sulphate) and evaporated in vacuo to give a white solid. Crystallisation from ethanol gave 5(e)-t-butyl-2(e)-(4-ethynylphenyl)-1,3-dithiane 1-oxide (190 mg.).

The following were prepared in an analogous manner. 5(e)-t-butyl-2(e)-(4-bromophenyl)-1,3-dithiane 1-oxide and 5(e)-t-butyl-2(e)-(4-bromophenyl)-2(a)-methyl-1,3-dithiane-1-oxide.

Example 5

5(e)-t-Butyl-2(a)-(prod-1-ynyl)-2(e)-methyl-1,3-dithiane

A solution of diisopropylamine (209 µl.) in dry tetrahydrofuran (10 ml.) was cooled to 0° and stirred under nitrogen while n-butyllithium (1 ml, 1.6M in hexane) was added. After cooling to −70° a solution of 5(e)-t-butyl-2(e)-(prop-1-ynyl)-1,3-dithiane (320 mg.) in dry tetrahydrofuran (10 ml.) was added over 30 minutes. Methyl iodide (300 µl.) was added and the solution allowed to warm to room temperature. Water and ether were added and the solutions separated. The organic solution was washed with dilute hydrochloric acid and brine, dried over anhydrous magnesium sulphate and evaporated. The residue was chromatographed on silica eluting with hexane: ether; 9:1. Crystallisation from hexane yielded a yellow solid (50 mg.).

The following were prepared in an analogous manner:
5-(e)-t-butyl-2(e)-methyl-2(a)-(trimethylsilylethynyl)-1,3-dithiane
5-(e)-t-butyl-2(e)-methyl-2(a)-(3,3-dimethylbut-1-ynyl)-1,3-dithiane.
from 5-(e)-t-butyl-2(e)-trimethylsilylethynyl)-1,3-dithiane and 5(e)-t-butyl-2-(e)-(3,3-dimethylbut-1-ynyl)-1,3-dithiane respectively.

Example 6

5(e)-t-Butyl-2(a)-(3,3-dimethylbut-1ynyl)-1,3-dithiane

A solution of diisopropylamine (200 µl.) in dry tetrahydrofuran (10 ml.) was cooled to 0° and stirred under nitrogen while n-butyllithium (1 ml., 1.6M in hexane) was added. After 10 minutes a solution of 5(e)-1-butyl-2(e)-(3,3-dimethylbut-1-ynyl)-1,3-dithiane (300 mg.) in dry tetrahydrofuran (10 ml.) was added. After 30 minutes water, dilute hydrochloric acid and ether were added, the solutions separated and the organic phase washed with brine, dried over anhydrous magnesium sulphate and evaporated. Flash chromatography on silica eluting with hexane:ether; 19:1 yielded the title compound (162 mg.).

By analogous methodology the following compound was prepared:
5(e)-t-Butyl-2(a)-(4-bromophenyl)-1,3-dithiane.

Example 7

5-t-Butyl-(3,3-dimethylbut-1-ynyl)-1,3-dithiane-1-oxide

5-[-Butyl-2-(3,3-dimethylbut-1-ynyl)-1,3-dithiane (0.46 g.), acetic acid (10 ml.) and hydrogen peroxide (200 µl. 30% solution) were stirred at room temperature overnight. The solution was evaporated to dryness and the product crystallised from hexane to give the title compound (70 mg.).

5-t-Butyl-2-(3,3-dimethylbut-1-ynyl)-1,3-dithiane-trioxide and tetraoxide were prepared in a similar manner.

Example 8

5(e)-t-Butyl-2(e)-(4-methylthiophenyl)-1,3-dithiane n-Butyllithium (1.6M solution in hexane, 2.26 ml.) was added to a solution of 5(e)-t-butyl-2(e)-(4-bromophenyl)-1,3-dithiane (1.0 g.) in dry tetrahydrofuran (50 ml.) stirred under nitrogen at −20°. After 1 hour methyldisulphide (0.51 g.) in dry tetrahydrofuran (5 ml.) was added and the mixture allowed to warm to 20°. Saturated sodium chloride solution and chloroform were added and the solutions separated. The aqueous phase was extracted with chloroform and the combined organic extracts dried (anhydrous magnesium sulphate) and evaporated in vacuo to give an oil. Chromatography on silica eluting with ether:hexane; 1:10 yielded 5(e)-t-butyl-2(e)-(4-methylthiophenyl)-1,3-dithiane (38 mg.).

Example 9

5-t-Butyl-2-(4-hydoxymethylcyclohexyl)-2-methyl-1,3-dithiane

A solution of 5-t-butyl-2-(4-ethoxycarbonylcyclohexyl)-2-methyl-1,3-dithiane (0.76 g.) in dry ether (10 ml.) was added, with stirring, to a suspension of lithium aluminium hydride (142 mg.) in dry ether (15 ml.) under nitrogen at 0° C. After allowing to warm to 25° C. the reaction mixture was stirred for 2 hours. Aqueous sodium hydroxide solution was then added (1.25 ml. of a 10% solution). The ether solution was decanted and the residue washed with 2×25 ml. portions of ether. After drying over anhydrous magnesium sulphate the solvent was removed under reduced pressure to give 5-t-butyl-2-(4-hydroxymethylcyclohexyl)-2-methyl-1,3-dithiane.

Example 10

5-t-Butyl-2-(4-ethynylcyclohexyl)-2-methyl-1,3-dithiane i) Dimethyl sulphoxide (376 µl.) in dichloromethane (2 ml.) was added over 5 minutes to a solution of oxalyl chloride (210 µl.) in dichloromethane (3 ml.) at −70° C. After stirring for a further 5 minutes a solution of 5-t-butyl-2-(4-hydroxymethylcyclohexyl)-2-methyl-1,3-dithiane (650 mg.) in dichloromethane (2 ml.) was added. The reaction mixture was stirred for 30 minutes. Triethylamine (1.5 ml.) was added and the mixture allowed to warm to 25° C. over 3 hours. Water (25 ml.) was added and the crude product obtained by dichloromethane extraction. After washing with dilute hydrochloric acid, saturated sodium bicarbonate solution and brine and then drying over anhydrous magnesium sulphate the solution was evaporated to give 5-t-butyl-2-(4-formylcyclohexyl)-2- methyl-1,3-dithiane as a gum.

Nuclear Magnetic Resonance Spectrum (NMR) was as follows: 0.9–3.0,27H,m; 9.5,1H,m.

Mass spectrum (M+1) 301.

ii) A solution of dry carbon tetrabromide (653 mg.) in dry dichloromethane (20 ml.) was added dropwise to a stirred solution of triphenyl phosphine (1.03 g.) in dichloromethane (10 ml.). After 10 minutes at 25° C. a solution of 5-t-butyl-2-(4-formylcyclohexyl)-2-methyl-1,3-dithiane (590 mg.) in dichloromethane (5 ml.) was added. After stirring overnight, the yellow solution was washed successively with dilute hydrochloric acid, saturated sodium bicarbonate solution and brine. After drying over anhydrous magnesium sulphate, solvent was removed to yield a yellow residue which was mechanically stirred with hexane (200 ml.). After 1 hour the mixture was filtered and the hexane filtrate evaporated to give crude product. Pure 5-t-butyl-2-[4-(2,2-dibromoethenyl)cyclohexyl] -2-methyl-1,3-dithiane was obtained by column chromatography on silica gel and elution with 5% ether in hexane.

Nuclear Magnetic Resonance spectrum (NMR) was as follows: 0.9–2.8,27H,m; 6.05,1H,d,J=9Hz.

Mass Spectrum (M+1) 457.

iii) n-Butyllithium (0.96 ml. of a 1.6M solution in hexane) was added to a solution of 5-t-butyl-2-[4-(2,2-dibromoethenyl)cyclohexyl]-2-methyl-1,3-dithiane (250 mg.) in dry tetrahydrofuran (5 ml.) at −70° C. under nitrogen. The reaction mixture was stirred and allowed to warm to 25° C. over a period of 2 hours. Ether was added. After washing with brine the organic layer was dried and the solvent evaporated to yield crude product. 5-t-Butyl-2-(4-ethynylcyclohexyl)-2-methyl-1,3-dithiane was purified by column chromatography on silica gel and elution with 5% ether in hexane.

Example 11

Mixture of 5-t-butyl-2-[(4-prop-1-ynyl)cyclohexyl]-1,3-dithiane and 5-t-butyl-2-methyl-2-[(4-prop-1-ynyl)cyclohexyl]-1,3-dithiane n-Butyl lithium (0.94 ml. of a 1.6M solution in hexane) was added at 0° C. under nitrogen to a solution of 5-t-butyl-2-(4-ethynylcyclohexyl)-1,3-dithiane (105 mg.) in dry tetrahydrofuran (10 ml.). After stirring for 10 minutes methyl iodide (117 μl.) was added. The reaction mixture was stirred for 3 hours. Water was added and the organic layer was washed with brine. After drying over anhydrous magnesium sulphate, the solvent was removed to yield crude product. Chromatography on silica and elution with 10% ether hexane gave a mixture of 5-t-butyl-2-[4-(prop-1-ynyl)cyclohexyl] -1,3-dithiane and 5-t-butyl-2-methyl-2-(4-prop-1-ynyl)cyclohexyl)-1,3-dithiane.

TABLE 1C

Structures and Methods for Compounds Prepared from Dithiane Precursors

| Compound Number | $R^{2a,b}$ | m | n | isomer ratio (i):(ii) | Synthetic Method Example |
|---|---|---|---|---|---|
| 8 | eq. 4-Ethynylphenyl; ax. Me | 0 | 0 | | Example 3 |
| 24 | ax. 4-Bromophenyl; eq. H | 0 | 0 | | Example 6 |
| 45 | eq. 2-Fluoro-4-(trimethylsilylethynyl)phenyl; ax. H | 0 | 0 | | Example 2 |
| 46 | eq. 2-Fluoro-4-ethynyl-phenyl; ax. H | 0 | 0 | | Example 3 |
| 48 | eq. 3-Fluoro-4-ethynyl-phenyl; ax. H | 0 | 0 | | Example 3 |
| 54 | eq. 4-(2-Methoxycarbonylethynyl)phenyl; ax. H | 0 | 0 | | Example 1 |
| 62 | ax. 4-Ethynylphenyl; eq. Me | 0 | 0 | | Example 3 |
| 64 | eq. 4-Methylthiophenyl; ax. H | 0 | 0 | | Example 8 |
| 77 | ax. Prop-1-ynyl; eq. Me | 0 | 0 | | Example 5 |
| 78 | ax. Trimethylsilyl-ethynyl; eq. Me | 0 | 0 | | Example 5 |
| 80 | ax. 3,3-Dimethylbut-1-ynyl; eq. H | 0 | 0 | | Example 6 |
| 81 | ax. 3,3-Dimethylbut-1-ynyl; eq. Me | 0 | 0 | | Example 5 |
| 120 | eq. 4-Ethynylphenyl; ax. H | 1 | 0 | | Example 4 |
| 121 | i) eq. 3,3-Dimethylbut-1-ynyl; ax. H | 1 | 0 | 1:9 | Example 7 |
| | ii) ax. 3,3-Dimethylbut-1-ynyl; eq. H | 1 | 0 | | |
| 122 | eq. 4-Bromophenyl; ax. H | 1 | 0 | | Example 4 |
| 123 | eq. 4-Bromophenyl; ax. Me | 1 | 0 | | Example 4 |
| 124 | eq. 3,3-Dimethylbut-1-ynyl; ax. H | 2 | 1 | | Example 7 |
| 125 | i) eq. 3,3-Dimethylbut-1-ynyl; ax. H | 2 | 2 | 1:1 | Example 7 |
| | ii) ax. 3,3-Dimethylbut-1-ynyl; eq. H | 2 | 2 | | |

TABLE 1C-continued

Structures and Methods for Compounds Prepared from Dithiane Precursors

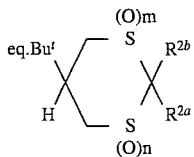

| Compound Number | $R^{2a,b}$ | m | n | isomer ratio (i):(ii) | Synthetic Method Example |
|---|---|---|---|---|---|
| 126 | ax. Ethynyl; eq. Me | 0 | 0 | | Example 3 |
| 127 | 4-Hydroxymethylcyclo-hexyl; Me | 0 | 0 | 4 isomers | Example 9 |
| 139 | 4-Ethynylcyclohexyl; Me | 0 | 0 | 2 isomers | Example 10 |
| 140 | i) ax. 4-(Prop-1-ynyl)-cyclohexyl; eq. Me | 0 | 0 | | Example 11 |
| | ii) x. 4-(Prop-1-ynyl)-cyclohexyl; eq. H | 0 | 0 | | |
| 142 | eq. 4-(Prop-1-ynyl)-phenyl; ax. H | 0 | 0 | | Example 2 |

BIOLOGICAL ACTIVITIES

The following examples illustrate, in a non-limiting manner, the pesticidal activity of compounds of formula (I).

Spray Tests

The activity of the compounds of the invention were tested by dissolving the compounds in acetone (5%) and then diluting in water: 'Symperonic' (94.5%: 0.5%) to five a water emulsion. The solution was then used to treat the following insects.

Musca domestica 20 female Musca were contained in a cardboard cylinder with gauze over both ends. Solution containing the compound was sprayed onto the insects so enclosed and mortality assessed after 48 hours at 25°.

The following compounds were active at <1000 p.p.m.:
6,10,27,31,33,34,35,42,47,53,62,68,69,73,74,76,86,89, 108,109,110,114,115, 117,118,119,121.

The following compounds were active at <200 p.p.m.:
1,3,4,8,9,12,13,14,15,16,17,18,19,20,21,22,23,24,26,28, 29,30,35,36,37,40, 41,46,48,51,56,57,65,66, 83,88,102,103, 120,122.

Sitophilus granarius and Triboltum castaneum 20 adult Sitophilus and Tribolium were added to 10 g. wheat which had been previously treated with 2 ml. of the solution containing the compound. Mortality was assessed after 6 days at 25° C.

The following compounds were active against Sitophilus granarius at <1000 p.p.m.:
1,9,10,13,14,15,20,23,28,30,41,47,52,53,57,62,67,75,76, 86,89,106,109,110, 117,118,119,121,122.

The following compounds were active against Sitophilus granarius at <200 p.p.m.:
4,8,17,18,19,24,46,48,54,60,73,74,78,82,83,88,108, 120,126.

The following compounds were active against Tribolium castaneum at <1000 p.p.m.:
4,8,18,47,48,49,62,69,76,84,114,115,117,118,119.

The following compounds were active against Tribolium castaneum at <200 p.p.m.:
17,46,73,74,75,78,82,83,88,102,103,108,109,110,126.

Myzus persicae 10 adult Myzus were placed on a leaf disc of chinese cabbage. 24 hours later the disc was sprayed with the solution containing the compound. Mortality was assessed after 2 days at 25°.

The following compounds were active at <1000 p.p.m.:
20,26,44,53,59,60,62,63,65,66,114.

The following compounds were active at <200 p.p.m.:
4,8,17,23,24,52,106

Plutella xylostella

7 Plutella larvae were sprayed with the solution containing the compound and added to a Chinese cabbage leaf which had been similarly sprayed and left to dry. Alternatively 8–10 Plutella larvae were put onto leaf discs and sprayed with the solution containing the compound. Mortality was assessed after 2 days at 25°.

The following compounds were active at <1000 p.p.m.:
4,18,35,37,39,41,47,53,54,57,70,71,76,78,86,88,107,109, 110,118,120.

The following compounds were active at <200 p.p.m.:
17,19,46,48,52,69,73,74,77,83,102,103,108,126.

Tetranychus Urticae

Leaf discs containing mixed population of Tetranychus urticae were sprayed with the solution of the compound. Mortality was assessed after 2 days at 25° C.

The following compounds were active at <1000 p.p.m.:
3,4,10,17,29,35,41,59,70,73,74,77,82,102,103,107, 112,126.

Additional Spray Tests

The activities of the compounds were investigated further. The compounds were dissolved in acetone (75%) and water (25%) was added. The solution was then used to spray the following insects:

Aphis fabae

A mixed population of Aphis fabae was tested on Nasturtium leaf.

The following compounds were active at <1000 p.p.m.:
17,19,21,22,26,30,35,36,40,41,44,47,54,62,65,66,67, 76,122

Macrosteles fascifrons

Adult Macrosteles fascifrons were tested on wheat seedlings. The following compounds were active at <1000 p.p.m.:
17,19,21,22,44,47,62,66,76

Diabrotica undecimpunctata

3rd Instar Diabrotica undecimpunctata were tested on filter paper

The following compounds were active at <1000 p.p.m.:
17,19,22,30,47,54,60,122.

The activity of compounds of the invention against unanaesthetised female *Musca domestica* (WRL strain), was demonstrated by the topical application to the test insect of a solution of the compound under test in butanone. Mortality was assessed at 48 hours.

The following compounds were active at <1 µg.:
1,3,4,6,8,9,13,14,15,17,26,28,29,36.

The activity of compounds of the invention against unanaesthatised female *Musca domestica* (WILL strain) was demonstrated by the topical application to the test insect of a solution of the compound under test with piperonyl butoxide in butanone. Mortality was assessed at 48 hours.

The following compounds were active at 1 µg.:
17,19,20,23,24,28,29,30,36,37,46,48,56,65,66,83.

Topical Application

The activity of compounds of the invention against anaesthetised male *Periplaneta americana* was demonstrated by the topical application to the test insect of a solution of the compound under test in butanone.

Mortality was assessed after 6 days.

The following compounds were active at <50 µg.
1,4,8,10,15,17,19,44,45,53,60.

The activity of compounds of the invention against anaesthetised male *Blattella germanica* was demonstrated by topical application to the test insect of a solution of the compound under test in butanone. Mortality was assessed after 6 days.

The following compounds were active at <5 µg.:
4,6,8,17,46,48,59,60,74,82,83,88,102,103,108,109,110, 115,120,121.

The activity of compounds of the inventions against second stage juvenile Meloidogyne was demonstrated by placing a batch of 20 nematodes in a test solution of the compound in acetone with 100 ppm. Triton X100 wetter. (Supplier: BDH). Reduction in undulations per minute were assessed after 1 day.

The following compounds were active in the range 41–61% at 100, 10 and 1 ppm.:
17,141.

| Formulations | |
|---|---|
| 1. Emulsifiable Concentrate | |
| Compound of formula (I) | 10.00 |
| Ethylan KEO | 20.00 |
| Xylene | 67.50 |
| Butylated Hydroxyanisole | 2.50 |
| | 100.00 |
| 2. Wettable Powder | |
| Compound of formula (I) | 25.00 |
| Attapulgite | 69.50 |
| Sodium isopropylbenzene sulphonate | 0.50 |
| Sodium salt of condensed naphthalene sulphonic acid | 2.50 |
| Butylated hydroxytoluene | 2.50 |
| | 100.00 |
| 3. Dust | |
| Compound of formula (I) | 0.50 |
| Butylated Hydroxyanisole | 0.10 |
| Talc | 99.40 |
| | 100.00 |
| 4. Bait | |
| Compound of formula (I) | 40.25 |
| Icing Sugar | 59.65 |
| Butylated hydroxy toluene | 0.10 |
| | 100.00 |
| 5. Lacquer | |
| Compound of formula (I) | 2.50 |
| Resin | 5.00 |
| Butylated Hydroxy anisole | 0.50 |
| High aromatic white spirit | 92.00 |
| | 100.00 |
| 6. Aerosol | |
| Compound of formula (I) | 0.30 |
| Butylated Hydroxy anisole | 0.10 |
| 1,1,1-Trichloroethane | 4.00 |
| Odourless Kerosene | 15.60 |
| Arcton 11/12. 50:50 mix | 80.00 |
| | 100.00 |
| 7. Spray | |
| Compound of formula (I) | 0.10 |
| Butylated Hydroxy anisole | 0.10 |
| Xylene | 10.00 |
| Odourless Kerosene | 89.80 |
| | 100.00 |
| 8. Potentiated Spray | |
| Compound of formula (I) | 0.10 |
| Piperonyl Butoxide | 0.50 |
| Butylated Hydroxyanisole | 0.10 |
| Xylene | 10.10 |
| Odourless Kerosene | 89.20 |
| | 100.00 |

Appendix 1
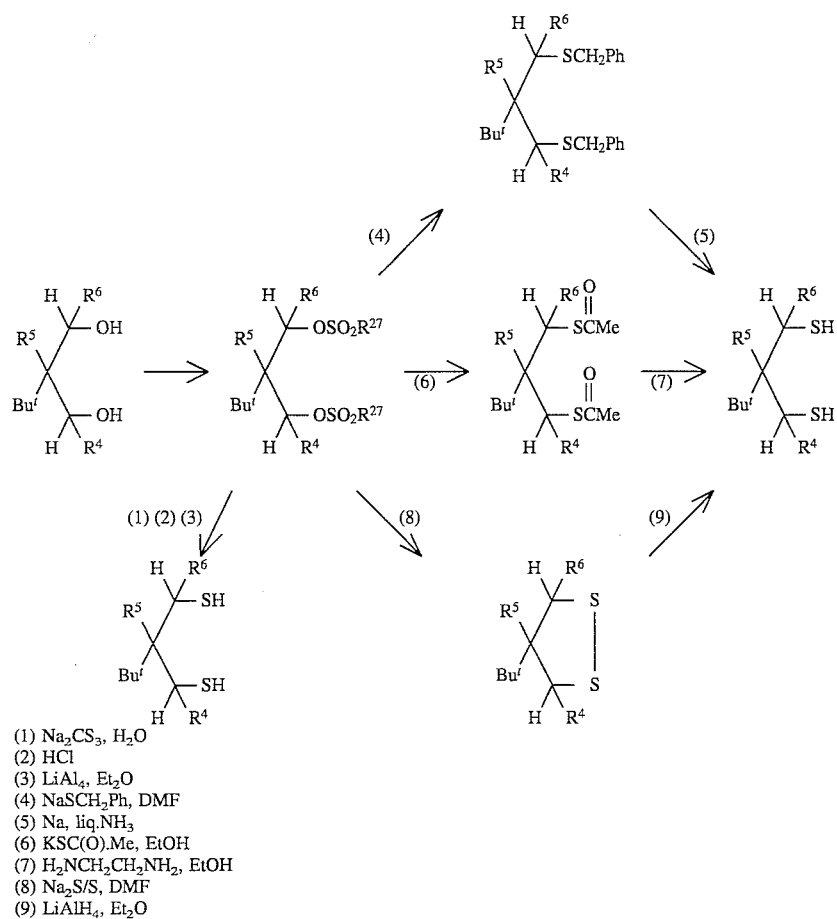
(1) $Na_2CS_3$, $H_2O$
(2) HCl
(3) $LiAl_4$, $Et_2O$
(4) $NaSCH_2Ph$, DMF
(5) Na, liq.$NH_3$
(6) KSC(O).Me, EtOH
(7) $H_2NCH_2CH_2NH_2$, EtOH
(8) $Na_2S/S$, DMF
(9) $LiAlH_4$, $Et_2O$
Appendix 2
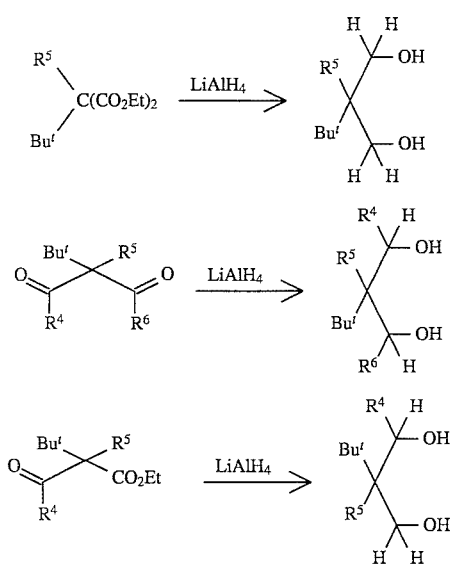
Appendix 3
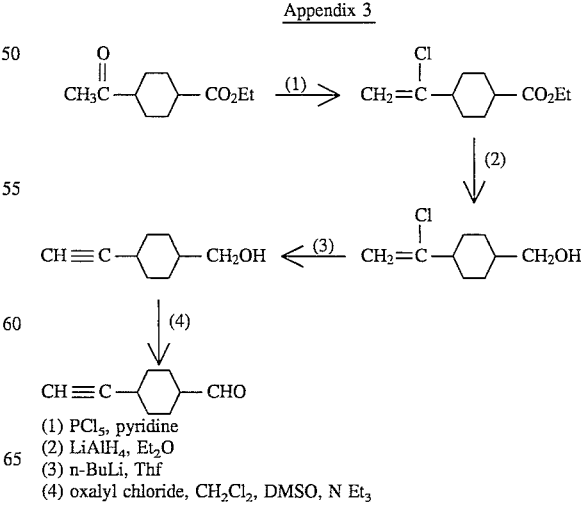
(1) $PCl_5$, pyridine
(2) $LiAlH_4$, $Et_2O$
(3) n-BuLi, Thf
(4) oxalyl chloride, $CH_2Cl_2$, DMSO, $NEt_3$

TABLE 2

Nuclear Magnetic Resonance Spectra:- $^1$H carried out in CDCl$_3$ and expressed as p.p.m. downfield from TMS, (number of protons, multiplicity, JHz, assignment).

1. 0.99(9H, s, —CMe$_3$), 1.73(1H, tt, J 11.5 and 2.5 Hz, 5-H$_{ax}$), 2.86(2H, dd, J 14 and 11.5 Hz, 4 and 6-H$_{ax}$), 2.99(2H, dd, J 14 and 2.5 Hz, 4 and 6-H$_{eq}$), 5.08(1H, s, 2-H$_{ax}$), 7.38(2H, d, J 7 Hz, ArH), 7.49(2H, d, J7Hz, ArH)
2. 0.97(9H, s, —CMe$_3$), 1.74(1H, tt, J 11.5 and 2.5Hz, 5-H$_{ax}$), 2.83(2H, dd, J 14 and 11.5 Hz, 4 and 6-H$_{ax}$), 2.98(2H, dd, J 14 and 2.5 Hz, 4 and 6-H$_{eq}$), 5.1(1H, s, 2-H$_{ax}$), 7.30(2H, d, J 7Hz, ArH), 7.41(2H, d, J 7Hz)
3. 0.93(9H, s, —CMe$_3$), 1.76(1H, tt, J 11.5 and 2.5 Hz, 5-H$_{ax}$), 2.84(2H, dd, J 14 and 11.5 Hz, 4 and 6-H$_{ax}$), 2.95(2H, dd, J 14 and 2.5 Hz, 4 and 6 - H$_{eq}$), 5.08(1H, s, 2-H$_{ax}$), 7.14(2H, d, J 7 Hz, ArH), 7.68(2H, d, J 7Hz, ArH)
4. 0.98(9H, s, —CMe$_3$), 1.78(1H, tt, J 11.5 and 2.5 Hz, 5-H$_{ax}$), 2.84(2H, dd, J 14 and 11.5 Hz, 4 and 6-H$_{ax}$), 2.98(2H, dd, J14 and 2.5 Hz, 4 and 6 - H$_{eq}$), 3.07(1H, s, —C≡CH), 5.10(1H, s, 2-H$_{ax}$), 7.45(4H, m, ArH).
5. 1) 1.00(9H, s, —CMe$_3$), 1.78(1H, tt, J11.5 and 2.5Hz, 5-H$_{ax}$), 2.22(3H, s, 2-Me$_{ax}$), 2.82(2H, dd, J 14 and 2.5 Hz, 4 and 6-H$_{eq}$), 3.04(2H, dd, J 14 and 11.5 Hz, 4 and 6-H$_{ax}$), 7.48(2H, d, J 7Hz, ArH), 7.68(2H, d, J 7Hz, ArH)
    ii) 0.82(9H, s, —CMe$_3$), 1.67(3H, s, 2-Me$_{eq}$), 1.74(1H, tt, J 11.5 and 2.5 Hz, 5-H$_{ax}$), 2.39(2H, dd, J 14 and 11.5 Hz, 4 and 6-H$_{ax}$), 2.69(2H, dd, J 14 and 2.5 Hz, 4 and 6-H$_{eq}$), 7.50(2H, d, J 7Hz, ArH), 7.84(2H, d, J 7Hz, ArH).
6. 0.23(9H, s, —SiMe$_3$), 0.96(9H, s, —CMe$_3$), 1.77(1H, tt, J 11.5 and 2.5Hz, 5-H$_{ax}$), 2.83(2H, dd, J 14 and 11.5 Hz, 4 and 6-H$_{ax}$), 2.98(2H, dd, J 14 and 2.5 Hz, 4 and 6-H$_{eq}$), 5.10(1H, s, 2-H$_{ax}$), 7.40(4H, m, ArH)
7. 0.84(3H, t, J 7Hz, CH$_2$Me), 0.97(9H, s, —CMe$_3$), 1.70(1H, tt, J 11.5 and 2.5 Hz, 5-H$_{ax}$), 2.41(2H, q, J 7Hz, —CH$_2$Me), 2.78(2H, dd, J 14 and 2.5 Hz, 4 and 6-H$_{eq}$), 2.90(2H, dd, J 14 and 11.5 Hz, 4 and 6-H$_{ax}$), 7.45(2H, d, J 7Hz, ArH), 7.55(2H, d, J 7Hz, ArH)
8. 0.99(9H, s, —CMe$_3$), 1.78(1H, tt, J 11.5 and 2.5 Hz, 5-H$_{ax}$), 2.22(3H, s, 2-Me$_{ax}$), 2.81(2H, dd, J 14 and 2.5 Hz, 4 and 6-H$_{eq}$), 3.01(2H, dd, J 14 and 11.5 Hz, 4 and 6-H$_{ax}$), 3.09(1H, s, C≡CH), 7.50(2H, d, J 7Hz, ArH), 7.79(2H, d, J 7Hz, ArH)
9. i) 0.94(9H, s, —CMe$_3$), 1.79(1H, tt, J 11.5 and 2.5 Hz, 5-H$_{ax}$), 2.82(2H, dd, J 14 and 11.5 Hz, 4 and 6-H$_{ax}$), 2.94(2H, dd, J 14 and 2.5 Hz, 4 and 6-H$_{eq}$), 5.04(1H, s, 2-H$_{ax}$), 7.27(1H, dd, J 7 and 1.5 Hz, ArH), 7.40(1H, d, J 7Hz, ArH), 7.58(1H, d, J 1.5 Hz, ArH)
    ii) 0.86(9H, s, —CMe$_3$), 1.79(1H, tt, J 11.5 and 2.5 Hz, 5-H$_{ax}$), 2.55(2H, dd, J 14 and 11.5 Hz, 4 and 6-H$_{ax}$), 2.70(2H, dd, J 14 and 2.5 Hz, 4 and 6-H$_{eq}$), 4.77(1H, s, 2-H$_{eq}$), 7.34(1H, d, J 7Hz, ArH), 7.61(1H, dd, J 7 and 1.5 Hz, ArH), 7.89(1H, d, J 1.5 Hz, ArH).
10. 0.98(9H, s, —CMe$_3$), 1.76(1H, tt, J 11.5 and 2.5 Hz, 5-H$_{ax}$), 2.83(2H, dd, J 14 and 11.5 Hz, 4 and 6-H$_{ax}$), 3.00(2H, dd, J 14 and 2.5 Hz, 4 and 6-H$_{eq}$), 5.15(1H, s, 2-H$_{ax}$), 7.55(2H, d, J 7Hz, ArH), 7.65(2H, d, J 7Hz, ArH)
11. i) 1.00(9H, s, —CM$_3$), 1.74(1H, tt, J 11.5 and 2.5 Hz, 5-H$_{ax}$), 2.22(3H, s, 2-Me$_{ax}$), 2.87(2H, dd, J 14 and 2.5 Hz, 4 and 6-H$_{eq}$), 3.04(2H, dd, J 14 and 11.5 Hz, 4 and 6-H$_{ax}$), 7.69(2H, d, J 7Hz, ArH), 7.92(2H, d, J 7Hz, ArH)
    ii) 0.83(9H, s, —CMe$_3$), 1.69(3H, s, 2-Me$_{eq}$), 1.74(1H, tt, J 11.5 and 2.5 Hz, 5-H$_{ax}$), 2.34(2H, dd, J 14 and 11.5 Hz, 4 and 6-H$_{ax}$), 2.70(2H, dd, J 14 and 2.5 Hz, 4 and 6-H$_{eq}$), 7.69(2H, d, J 7Hz, ArH), 8.04(2H, d, J 7Hz, ArH)
12. 0.98(9H, s, —CMe$_3$), 1.7(1H, tt, J 11.5 and 2.5 Hz, 5-H$_{ax}$), 2.2(3H, s, 2-Me$_{ax}$), 2.8(2H, dd, J 14 and 2.5 Hz 4 and 6-H$_{eq}$), 3.05(2H, dd, J 14 and 11.5 Hz, 4 and 6-H$_{ax}$), 7.43(1H, d, J 7Hz, ArH), 7.65(1H, dd, J 7 and 1.5 Hz, ArH), 7.90(1H, d, J 1.5 Hz, ArH)
13. 0.82(9H, s, —CMe$_3$), 1.66(3H, s, 2-Me$_{eq}$), 1.7(1H, tt, J 11.5 and 2.5 Hz, 5-H$_{ax}$), 2.4(2H, dd, J 14 and 11.5 Hz, 4 and 6-H$_{ax}$), 2.7(2H, dd, J 14 and 2.5 Hz, 4 and 6-H$_{eq}$), 7.42(1H, d, J 7Hz, ArH), 7.83(1H, dd, J 7 and 1.5 Hz, ArH), 8.1(1H, d, J 1.5 Hz, ArH)
14. 0.95(9H, s, —CMe$_3$), 1.78(1H, tt, J 11.5 and 2.5 Hz, 5-H$_{ax}$), 2.20(3H, s, 2-Me$_{ax}$), 2.83(2H, dd, J 14 and 2.5 Hz, 4 and 6-H$_{eq}$), 3.02(2H, dd, J 14 and 11.5 Hz, 4 and 6-H$_{ax}$), 7.45(2H, d, J 7Hz, ArH), 7.65(2H, d, J 7Hz, ArH)
15. 0.95(9H, s, —CMe$_3$), 1.80(1H, tt, J, 11.5 and 2.5 Hz, 5-H$_{ax}$), 2.85(2H, dd, J 14 and 11.5, 4 and 6-H$_{ax}$), 3.00(2H, dd, J 14 and 2.5, 4 and 6-H$_{eq}$), 5.20(1H, s, 2-H$_{ax}$), 7.45(1H, t, J 7Hz, ArH), 7.56(1H, d, J 7Hz, ArH), 7.65(1H, d, J 7Hz, ArH), 7.72(1H, s, ArH)
16. 0.97(9H, s, —CMe$_3$), 1.40(1H, m, 5-H$_{ax}$), 1.70(3H, d, J, 7Hz, 4-Me$_{ax}$), 2.67(1H, dd, J, 10.5 and 4.5 Hz, 6-H$_{eq}$), 2.95(1H, dq, J, 7 and 2.7 Hz, 4-H$_{eq}$), 3.25(1H, dd, J, 14 and 10.5 Hz, 6-H$_{ax}$), 5.70(1H, s, 2-H$_{ax}$), 7.45(2H, d, J 7Hz, ArH), 7.48(2H, d, J 7Hz, ArH).
17. 0.99(9H, s, —CHCMe$_3$), 1.2(9H, s, CCMe$_3$), 1.70(1H, tt, J 11.5 and 2.5Hz, 5-Hax), 2.7(2H, dd, J 14 and 11.5Hz, 4 and 6-H$_{ax}$), 4 and 6-H$_{ax}$), 2.85(2H, dd, J 14 and 11.5 Hz, 4 and 6-H$_{eq}$), 4.80(1H, s, 2-H$_{ax}$).
18. 0.20(9H, s, SiMe$_3$), 0.95(9H, s, —CMe$_3$), 1.70(1H, tt, J 10 and 3.5Hz, 5-H$_{ax}$), 2.70(2H, dd, J 10 and 14Hz, 4 and 6-H$_{ax}$), 2.90(2H, dd, J 3.5 and 14Hz, 4 and 6-H$_{eq}$), 4.85(1H, s, 2-H$_{ax}$).
19. 0.95(9H, s, CHMe$_3$), 1.25(9H, s, CCMe$_3$), 1.80(1H, tt, J 11.5 and 2.5Hz, 5-H$_{ax}$), 2.05(3H, s, 2-Me$_{ax}$), 2.80(2H, dd, J 14 and 2.5Hz, 4 and 6-H$_{eq}$), 2.90(2H, dd, J 11.5 and 2.5Hz, 4 and 6-H$_{ax}$).
20. i) 0.9(9H, s, —CMe$_3$), 1.7(1H, m, 5-H$_{ax}$), 2.2(3H, s, 2-Me$_{ax}$), 2.8(2H, dd, 4/6-H$_{eq}$), 3.0(2H, dd, 4/6-H$_{ax}$), 7.4(1H, d, Ar—H), 7.6(1H, d, Ar—H), 7.4(1H, s, Ar—H).
    ii) 0.9(9H, s, —CMe$_3$), 1.6(3H, s, 2-Me$_{eq}$), 1.7(1H, m, 5-H$_{ax}$), 2.4(2H, dd, 4/6-H$_{ax}$), 2.6(2H, dd, 4/6-H$_{eq}$), 7.4(1H, d, Ar—H), 7.6(1H, d, Ar—H), 8.1(1H, d, Ar—H).
21. 0.9(9H, s, —CMe$_3$), 1.8(1H, tt, 5-H$_{ax}$), 2.3(3H, s, 2-Me$_{ax}$), 2.9(2H, dd, 4/6-H$_{eq}$), 3.1(2H, dd, 4/6-H$_{ax}$), 7.5(2H, m, Ar—H), 8.1(2H, m, Ar—H).
22. 0.9(9H, s, —CMe$_3$), 1.7(3H, s, 2-Me$_{eq}$), 1.7(1H, tt, 5-H$_{ax}$), 2.3(2H, dd, 4/6-H$_{ax}$), 2.7(2H, dd, 4/6-H$_{eq}$), 7.5(2H, m, Ar—H), 8.3(2H, m, Ar—H).

TABLE 2-continued

Nuclear Magnetic Resonance Spectra:- $^1$H carried out in CDCl$_3$ and expressed as p.p.m. downfield from TMS, (number of protons, multiplicity, JHz, assignment).

23  0.8(9H, s, —CMe$_3$), 1.6(3H, s, 2-Me$_{eq}$), 1.7(1H, tt, 5-H$_{ax}$), 2.4(2H, dd, 4/6-H$_{ax}$), 2.6(2H, dd, 4/6-H$_{eq}$), 7.4(2H, d, Ar—H), 7.9(2H, d, Ar—H).

24  0.9(9H, s, —CMe$_3$), 1.8(1H, tt, 5-H$_{ax}$), 2.5–9(4H, m, 4/6-H$_{ax+eq}$), 4.8(1H, s, 2-H$_{eq}$), 7.4(2H, d, Ar—H), 7.7(2H, d, Ar—H).

25  0.9(9H, s, —CMe$_3$), 1.6(3H, s, 2-Me$_{eq}$), 1.7(1H, tt, 5-H$_{ax}$), 2.4(2H, dd, 4/6-H$_{ax}$), 2.7(2H, dd, 4/6-H$_{eq}$), 7.3(1H, s, Ar—H), 7.9(2H, s, Ar—H).

26  0.9(9H, s, —CMe$_3$), 1.7(1H, tt, 5-H$_{ax}$), 2.3(3H, s, 2-Me$_{ax}$), 2.8(2H, dd, 4/6-H$_{eq}$), 3.0(2H, dd, 4/6-H$_{ax}$), 7.3(2H, m, Ar—H), 7.7(1H, d, Ar—H).

27  i) 0.9(9H, s, —CMe$_3$), 1.7(1H, tt, 5-H$_{ax}$), 1.9(3H, s, 2-Me$_{ax}$), 2.5(2H, dd, 4/6-H$_{eq}$), 2.7(2H, dd, 4/6-H$_{ax}$), 7.2(2H, m, Ar—H), 7.5(1H, d, Ar—H).
   ii) 0.9(9H, s, —CMe$_3$), 1.7(1H, tt, 5-H$_{ax}$), 1.9(3H, s, 2-Me$_{ax}$), 2.5(2H, dd, 4/6-H$_{eq}$), 2.7(2H, dd, 4/6-H$_{ax}$), 2.7(2H, dd, 4/6-H$_{ax}$), 7.2(2H, m, Ar—H), 7.5(1H, d, Ar—H).

28  0.9(9H, s, —CMe$_3$), 1.6(3H, s, 2-Me$_{eq}$), 1.7(1H, tt, 5-H$_{ax}$), 2.4(2H, dd, 4/6-H$_{ax}$), 2.6(2H, dd, 4/6-H$_{eq}$), 7.7(2H, d, Ar—H), 8.2(2H, d, Ar—H).

29  0.9(9H, s, —CMe$_3$), 1.8(1H, tt, 5-H$_{ax}$), 2.3(3H, s, 2-Me$_{ax}$), 2.8(2H, dd, 4/6-H$_{eq}$), 3.0(2H, dd, 4/6-H$_{ax}$), 7.5(2H, d, Ar—H), 7.9(2H, d, Ar—H).

30  0.9(9H, s, —CMe$_3$), 1.8(1H, tt, 5-H$_{ax}$), 2.8(4H, m, 4/6-H$_{ax+eq}$), 5.4(1H, s, 2-H$_{ax}$), 7.2(2H, m, Ar—H), 7.5(1H, t, Ar—H).

31  0.9(9H, s, —CMe$_3$), 1.8(1H, tt, 5-H$_{ax}$), 2.8(4H, m, 4/6-H$_{ax+eq}$), 5.2(1H, s, 2-H$_{ax}$), 7.6(4H, s, Ar—H).

32  0.9(9H, s, —CMe$_3$), 1.6(3H, s, 2-Me$_{eq}$), 1.6(1H, tt, 5-H$_{ax}$), 2.2(2H, dd, 4/6-H$_{ax}$), 2.7(2H, dd, 4/6-H$_{eq}$), 7.8(1H, s, Ar—H), 8.5(2H, s, Ar—H).

33  0.9(9H, s, —CMe$_3$), 1.7(1H, tt, 5-H$_{ax}$), 2.4(3H, s, 2-Me$_{ax}$), 2.8(2H, dd, 4/6-H$_{eq}$), 3.0(2H, dd, 4/6-H$_{ax}$), 7.8(1H, s, Ar—H), 8.3(2H, s, Ar—H).

34  0.9(9H, s, —CMe$_3$), 1.8(1H, tt, 5-H$_{ax}$), 2.8–3.1(4H, m, 4/6-H$_{ax+eq}$), 5.2(1H, s, 2-H$_{ax}$), 7.8(1H, s, Ar—H), 8.0(2H, s, Ar—H).

35  0.9(9H, s, —CMe$_3$), 1.6(3H, s, 2-Me$_{eq}$), 1.7(1H, tt, 5-H$_{ax}$), 2.3(2H, dd, 4/6-H$_{ax}$), 2.7(2H, dd, 4/6-H$_{eq}$), 7.6(1H, d, Ar—H), 8.0(1H, d, Ar—H), 8.3(1H, d, Ar—H).

36  0.9(9H, s, —CMe$_3$), 1.6(3H, s, 2-Me$_{eq}$), 1.7(1H, tt, 5-H$_{ax}$), 2.3(2H, dd, 4/6-H$_{ax}$), 2.7(2H, dd, 4/6-H$_{eq}$), 7.6(1H, d, Ar—H), 8.0(1H, d, Ar—H), 8.3(1H, d, Ar—H).

37  0.9(9H, s, —CMe$_3$), 1.7(1H, tt, 5-H$_{ax}$), 2.2(3H, s, 2-Me$_{ax}$), 2.8(2H, dd, 4/6-H$_{eq}$), 3.0(2H, dd, 4/6-H$_{ax}$), 7.6(1H, d, Ar—H), 7.8(1H, d, Ar—H), 8.1(1H, s, Ar—H).

38  i) 1.0(9H, s, —CMe$_3$), 1.6(1H, tt, 5-H$_{ax}$), 2.2(3H, s, 2-Me$_{ax}$), 2.8(2H, dd, 4/6-H$_{eq}$), 3.0(2H, dd, 4/6-H$_{ax}$), 4.5(2H, s, CH$_2$O), 7.5(2H, d, Ar—H), 7.7(2H, d, Ar—H).
   ii) 0.8(9H, s, —CMe$_3$), 1.6(1H, tt, 5-H$_{ax}$), 1.6(3H, s, 2-Me$_{eq}$), 2.4(2H, dd, 4/6-H$_{ax}$), 2.6(2H, dd, 4/6-H$_{eq}$), 4.5(2H, s, CH$_2$O), 7.5(2H, d, Ar—H), 8.0(2H, d, Ar—H).

39  1.0(9H, s, —CMe$_3$), 1.6(1H, tt, 5-H$_{ax}$), 2.2(3H, s, 2-Me$_{ax}$), 2.8(2H, dd, 4/6-H$_{eq}$), 3.0(2H, dd, 4/6-H$_{ax}$), 4.5(2H, s, CH$_2$O), 7.5(2H, d, Ar—H), 7.7(2H, d, Ar—H).

40  0.9(9H, s, —CMe$_3$), 1.7(1H, tt, 5-H$_{ax}$), 2.7–3.1(4H, m, 4/6-H$_{ax+eq}$), 5.5(1H, s, 2-H$_{ax}$), 7.2(1H, m, Ar—H), 7.4(1H, s, Ar—H), 7.6(1H, d, Ar—H). .

41  0.9(9H, s, —CMe$_3$), 1.8(1H, tt, 5-H$_{ax}$), 2.7–3.1(4H, m, 4/6-H$_{ax+eq}$), 5.1(1H, s, 2-H$_{ax}$), 7.2(1H, dd, Ar—H), 7.6(2H, dd, Ar—H).

42  1.0(9H, s, —CMe$_3$), 1.75(1H, tt, 5-H$_{ax}$), 2.82(2H, dd, 4/6-H$_{ax}$), 2.98(2H, dd, 4/6-H$_{eq}$), 5.04(1H, s, 2-H$_{ax}$), 7.3(3H, m, Ar—H).

43  0.98(9H, s, —CMe$_3$), 1.75(1H, tt, 5-H$_{ax}$), 2.84(2H, dd, 4/6-H$_{ax}$), 2.97(2H, dd, 4/6-H$_{eq}$), 3.8(3H, s, OMe), 5.11(1H, s, 2-H$_{ax}$), 6.87(2H, m, Ar—H), 7.41(2H, m, Ar—H).

44  1.0(9H, s, —CMe$_3$), 1.85(1H, tt, 5-H$_{ax}$), 2.89(2H, dd, 4/6-H$_{ax}$), 3.02(2H, dd, 4/6-H$_{eq}$), 5.5(1H, m, 2-H$_{ax}$).

45  0.27(9H, s, —SiMe$_3$), 0.98(9H, s, —CMe$_3$), 1.76(1H, tt, 5-H$_{ax}$), 2.88(2H, dd, 4/6-H$_{ax}$), 2.99(2H, dd, 4/6-H$_{eq}$), 5.48(1H, s, 2-H$_{ax}$), 7.2(2H, m, Ar—H), 7.56(1H, m, Ar—H).

46  0.98(9H, s, —CMe$_3$), 1.45(1H, s, ≡C—H), 1.78(1H, tt, 5-H$_{ax}$), 2.89(2H, dd, 4/6-H$_{ax}$), 2.99(2H, dd, 4/6-H$_{eq}$), 5.48(1H, s, 2-H$_{ax}$), 7.23(2H, m, Ar—H), 7.59(1H, m, Ar—H).

47  0.9 and 0.99(9H, s, —CMe$_3$), 1.74 and 1.86(1H, tt, 5-H), 2.5–3.1(4H, m, 4/6-H$_{ax+eq}$), 7.89(2H, s, Ar—H).

48  1.0(9H, s, —CMe$_3$), 1.45(1H, m, ≡C—H), 1.79(1H, tt, 5-H$_{ax}$), 2.88(2H, dd, 4/6-H$_{ax}$), 2.99(2H, dd, 4/6-H$_{eq}$), 5.04(1H, s, 2-H$_{ax}$), 7.16(3H, m, Ar—H).

49  1.0(9H, s, —CMe$_3$), 1.6(1H, m, 5-H$_{ax}$), 2.4(3H, m, 2-Me), 2.9(4H, m, 4/6-CH$_2$).

50  0.95(9H, s, —CMe$_3$), 1.7(1H, m, 5-H$_{ax}$), 2.0(3H, s, 2-Me), 2.8(4H, m, 4/6-CH$_2$).

51  0.9(9H, s, —CMe$_3$), 1.7(1H, tt, 5-H$_{ax}$), 2.8–3.0(4H, m, 4/6-H$_{ax+eq}$), 5.5(1H, s, 2-H$_{ax}$), 7.3(1H, d, Ar—H), 7.4(1H, d, Ar—H), 7.7(1H, t, Ar—H).

52  0.9(9H, s, —CMe$_3$), 1.8(1H, tt, 5-H$_{ax}$), 2.8–3.0(4H, m 4/6-H$_{ax+eq}$), 4.5(2H, d, CH$_2$O), 5.2(1H, s, —OH), 7.4(4H, s, Ar—H).

53  0.9(9H, s, —CMe$_3$), 1.8(1H, tt, 5-H$_{ax}$), 2.2(3H, s, COMe), 2.8–3.0(4H, m, 4/6-H$_{ax+eq}$), 4.8(2H, s, CH$_2$O), 5.2(1H, s, 2-H$_{ax}$), 7.5(4H, s, Ar—H).

54  0.9(9H, s, —CMe$_3$), 1.8(1H, tt, 5-H$_{ax}$), 2.8–3.0(4H, m, 4/6-H$_{ax+eq}$), 3.8(3H, s, OMe), 5.2(1H, s, 2-H$_{ax}$), 7.4–7.6(4H, dd, Ar—H).

55  0.9(9H, s, —CMe$_3$), 1.7(1H, tt, 4-H$_{ax}$), 2.8–3.0(4H, m, 4/6-H$_{ax+eq}$), 5.5(1H, s, 2-H$_{ax}$), 7.0(1H, ddd, Ar—H), 7.1(1H, dd, Ar—H), 7.7(1H, dd, Ar—H).

56  1.0(9H, s, —CMe$_3$), 1.8(1H, tt, 5-H$_{ax}$), 2.4(3H, s, 2-Me$_{ax}$), 2.8–3.0(4H, m, 4/6-H$_{ax+eq}$), 7.8(2H, s, Ar—H).

57  0.9(9H, s, —CMe$_3$), 1.6(3H, s, 2-Me$_{eq}$), 1.7(1H, tt, 5-H$_{ax}$), 2.3(2H, dd, 4/6-H$_{ax}$), 2.6(2H, dd, 4/6-H$_{eq}$), 8.0(2H, s, Ar—H).

58  0.9(9H, s, —CMe$_3$), 1.8(1H, tt, 5-H$_{ax}$), 2.8–3.1(4H, m, 4/6-H$_{ax+eq}$), 5.4(1H, s, 2-H$_{ax}$), 7.8–8.2(3H, m, Ar—H).

59  0.9(9H, s, —CMe$_3$), 1.7(1H, tt, 5-H$_{ax}$(, 2.8–3.0(4H, m, 4/6-H$_{ax+eq}$), 3.4(3H, s, OMe), 3.6(2H, m, CH$_2$O), 3.7(2H, m, OCH$_2$), 4.4(2H, s, ≡C—CH$_2$O), 5.1(1H, s, 2-H$_{ax}$), 7.4(4H, s, Ar—H).

60  0.98(9H, s, —CMe$_3$), 1.80(1H, tt, 5-H$_{ax}$), 2.8–3.0(4H, m, 4/6-H), 3.45(3H, s, OMe), 4.30(2H, s, CH$_2$O),

TABLE 2-continued

Nuclear Magnetic Resonance Spectra:- $^1$H carried out in $CDCl_3$ and expressed as p.p.m. downfield from TMS, (number of protons, multiplicity, JHz, assignment).

5.12(1H, s, 2-H$_{ax}$), 7.40(4H, s, Ar—H).

61 i) 0.25(9H, s, SiMe$_3$), 0.95(9H, s, —CMe$_3$), 1.8(1H, m, 5-H$_{ax}$), 2.20(3H, s, 2-Me$_{ax}$), 2.75–3.10(4H, m, 4/6-H, 7.45(2H, d, Ar—H), 7.75(2H, d, Ar—H).
ii) 0.26(9H, s, SiMe$_3$), 0.80(9H, s, —CMe$_3$), 1.67(3H, s, 2-Me$_{eq}$), 1.70(1H, tt, 5-H$_{ax}$), 2.35(2H, dd, 4/6-H), 2.67(2H, dd, 4/6-H), 7.50(2H, dd, Ar—H), 7.95(2H, dd, Ar—H).

62 0.80(9H, s, —CMe$_3$), 1.68(3H, s, 2-Me$_{eq}$), 1.70(1H, tt, 5-H$_{ax}$), 2.40(2H, dd, 4/6-H), 2.65(2H, dd, 4/6-H), 3.10(1H, s, ≡C—H), 7.50(2H, d, Ar—H), 7.92(2H, d, Ar—H).

63 0.26(9H, s, SiMe$_3$), 0.80(9H, s, —CMe$_3$), 1.67(3H, s, 2-Me$_{eq}$), 1.70(1H, tt, 5-H$_{ax}$), 2.35(2H, dd, 4/6-H), 2.67(2H, dd, 4/6-H), 7.50(2H, dd, Ar—H), 7.95(2H, dd, Ar—H).

64 0.95(9H, s, —CMe$_3$), 1.75(1H, tt, 5-H$_{ax}$), 2.50(H, s, —SMe), 2.75–3.0, (4H, m, 4/6-H), 5.08(1H, s, 2-H$_{ax}$), 7.20(2H, d, Ar—H), 7.50(2H, dd, Ar—H).

65 0.9(9H, s, —CMe$_3$), 1.3(3H, s, 5-Me$_{ax}$), 2.6(2H, d, 4/6-H$_{ax}$), 3.2(2H, d, 4/6-H$_{eq}$), 5.0(1H, s, 2-H$_{ax}$), 7.4–7.6(4H, m, Ar—H).

66 0.8(9H, s, —CMe$_3$), 1.3(3H, s, 5-Me$_{ax}$), 2.3(2H, d, 4/6-H$_{eq}$), 3.1(2H, d, 4/6-H$_{ax}$), 5.0(1H, s, 2-H$_{eq}$), 7.4–7.6(4H, q, Ar—H).

67 0.8(9H, s, —CMe$_3$), 1.3(3H, s, 5-Me$_{ax}$), 1.7(3H, s, 2-Me$_{eq}$), 2.3(2H, d, 4/6-H$_{eq}$), 2.8(2H, d, 4/6-H$_{ax}$), 7.5–8.0(4H, dd, Ar—H).

68 1.0(9H, s, —CMe$_3$), 1.3(3H, s, 5-Me$_{ax}$), 2.15(3H, s, 2-Me$_{ax}$), 2.4(2H, d, 4/6-H$_{eq}$), 3.35(2H, 3, 4/6-H$_{ax}$), 7.5–7.7(4H, dd, Ar—H).

69 0.9(12H, m, —CMe$_3$), 1.4–1.6(2H, m, —CH$_2$), 1.7(1H, m, 5-H$_{ax}$), 2.2–3(2H, m), 2.7–9(4H, m, 4/6-H$_{eq+ax}$), 4.3 and 4.8(1H, s, 2-H).

70 0.9(9H, s, —CMe$_3$), 1.75(1H, tt, 5-H$_{ax}$), 1.95(3H, d, 2-≡—Me$_{ax}$), 2.7(2H, dd, 4/6-H$_{eq}$), 3.15(2H, dd, 4/6-H$_{ax}$), 4.3(1H, d, 2-H$_{eq}$).

71 0.9(9H, s, —CMe$_3$), 1.7(1H, tt, 5-H$_{ax}$), 1.85(3H, d, 2-≡—Me$_{eq}$), 2.75(4H, m, 4/6-H$_{ax+eq}$), 4.8(1H, d, 2-H$_{ax}$).

72 0.9(9H, s, —CMe$_3$), 1.0(3H, t, Me), 1.5(2H, m, —CH$_2$), 1.6(1H, tt, 5-H$_{ax}$), 2.3(2H, dt, 2-≡—CH$_{2ax}$), 2.7(2H, dd, 4/6-H$_{eq}$), 3.2(2H, dd, 4/6-H$_{ax}$), 4.4(1H, s, 2-H$_{eq}$).

73 0.9(9H, s, —CMe$_3$), 1.7(1H, tt, 5-H$_{ax}$), 2.0(1H, t, ≡C—H), 2.3(4H, m, CH$_2$x2), 2.6(2H, dd, 4/6-H$_{eq}$), 2.8(2H, dd, 4/6-H$_{ax}$), 4.1(1H, d, 2-H$_{eq}$), 5.9(2H, m, —CH=CH—).

74 0.9(9H, s, —CMe$_3$), 1.6(1H, tt, 5-H$_{ax}$), 2.0(1H, t, ≡C—H), 2.3(4H, m, CH$_2$x2), 2.75(4H, m, 4/6-H$_{ax+eq}$), 4.6(1H, d, 2-H$_{ax}$), 5.7(1H, dd, ≡C—H), 5.95(1H, dt, ≡C—H).

75 0.95(9H, s, —CMe$_3$), a.7(5H, m, 5-H$_{ax}$ and 2xCH$_2$), 1.9(1H, s, ≡CH), 2.3(2H, m, CH$_2$), 2.7(4H, m, 4/6-H$_{ax+eq}$).

3.5 and 4.1(1H, m, 2-H).

76 0.9(9H, s, —CMe$_3$), 1.7(7H, m, 5-H$_{ax}$ and 3xCH$_2$), 1.9(1H, m, ≡CH), 2.2(2H, m, CH$_2$), 2.7(4H, m, 4/6-CH$_2$), 4.0(1H, m, 2-H$_{ax}$).

77 1.0(9H, s, —CMe$_3$), 1.6(1Htt, J11.5 and 2.5Hz, 5-H$_{ax}$), 1.75(3H, s, 2-Me), 1.95(3H, s, ≡C—Me), 2.8(2H, dd, J, 14.5 and 2.5Hz, 4/6-H$_{eq}$), 3.1(2H, dd, J14.5 and 11.5Hz, 4/6-H$_{ax}$).

78 0.2(9H, s, SiMe$_3$), 1.0(9H, s, —CMe$_3$), 1.75(3H, s, 2-Me), 2.85(2H, dd, J14.5 and 2.5Hz, 4/6-H$_{eq}$), 3.1(2H, dd, J14.5 and 11.5Hz, 4/6-H$_{ax}$).

79 0.9 and 1.0(9H, s, —CMe$_3$), 1.1 and 1.25(3H, t, —Me), 1.7(1H, tt, 5-H$_{ax}$), 2.3(2H, m, ≡C.CH$_2$), 2.6–3.4(4H, m, 4/6-H$_{ax+eq}$), 4.4 and 4.8(1H, t, 2-H).

80 0.95(9H, s, —CMe$_3$), 1.3(9H, s, ≡C.CMe$_3$), 1.7(1H, m, 5-H$_{ax}$), 2.8(2H, m, 4/6-H$_{eq}$), 3.2(2H, m, 4/6-H$_{ax}$), 4.3(1H, s, 2-H$_{eq}$).

81 0.95(9H, s, —CMe$_3$), 1.25(9H, s, C≡C.CMe$_3$), 1.6(1H, m, 5-H$_{ax}$), 1.7(3H, s, 2-Me), 2.8(2H, dd, J14.5 and 2.5Hz, 4/6$_{eq}$), 3.1(2H, dd, J, 14.5 and 11.5Hz, 4/6-H$_{ax}$).

82 0.95(9H, s, —CMe$_3$), 1.6(1H, m, 5-H$_{ax}$), 2.8(2H, m, 4/6-H$_{ax}$), 2.95(2H, m, 4/6-H$_{eq}$), 4.75(1H, m, 2-H$_{ax}$), 6.4(2H, m, —CH=CH—).

83 0.95(9H, s, —CMe$_3$), 1.65(1H, tt, J11.5 and 2.5Hz, 5-H$_{ax}$), 2.2(2H, m, 2-CH$_2$), 2.7(2H, dd, J14.5 and 11Hz, 4/6-H$_{ax}$), 2.9(4H, m, 4/6H$_{eq}$ and CH$_2$CCl$_3$), 4.1(1H, t, J6.5Hz, 2-H$_{ax}$).

84 0.95(9H, s, —CM$_3$), 1.7(1H, tt, J, 11.0 and 2.5Hz, 5-H$_{ax}$), 2.8(2H, dd, J14.5 and 11 Hz, 4/6-H$_{ax}$), 3.05(2H, dd, J14.5 and 2.5Hz, 4/6-H$_{eq}$), 4.9(1H, s, 2-H$_{ax}$), 7.2(1H, s, =CH—).

85 0.95(9H, s, —CMe$_3$), 1.75(1H, tt, J11 and 2.5Hz, 5-H$_{ax}$), 2.75(2H, dd, J14 and 11 Hz, 4/6-H$_{ax}$), 2.95(2H, dd, J14 and 2.5Hz, 4/6-H$_{eq}$), 4.9(1H, s, 2-H$_{ax}$).

86 1.0(9H, s, —CMe$_3$), 1.65(1H, tt, J11 and 3Hz, 5-H$_{ax}$), 1.85(3H, s, 2-Me), 2.3(2H, m, —CH$_2$), 2.8(2H, dd, J14 and 3Hz, 4/6-H$_{eq}$), 2.9(2H, dd, J14 and 11Hz, 4/6-H$_{ax}$), 3.1(2H, m, CH$_2$CCl$_3$).

87 0.95(9H, s, —CMe$_3$), 1.55(3H, s, 2-Me), 2.8(6H, m, 4/6-H$_{ax+eq}$), and CH$_2$COH—), 4.4(1H, d, J8Hz, CH.OH).

88 0.92(9H, s, —CMe$_3$), 1.45(6H, s, —CMe$_2$), 1.70(1H, tt, 5-H$_{ax}$), 2.65–2.90(4H, m, 4/6-H), 3.35(3H, s, OMe), 4.80(1H, s, 2-H$_{ax}$).

89 (i) 0.9(9H, s, —CMe$_3$), 1.2–1.8(11H, m, 4-H$_{ax}$ + Cyclohexyl), 2.5–2.9(4H, m, 4/6-H), 2.5–2.9 and 3.2(1H, dt, cyclohexyl-1H), 4.80(1H, d, 2-H$_{ax}$).
(ii) 0.95(9H, s, —CMe$_3$), 1.2–1.8(11H, m, 5-H$_{ax}$ + Cyclohexyl), 2.4–2.9(4H, m, 4/6-H), 2.5–2.9 and 3.2(1H, m, Cyclohexyl-1H), 4.37(1H, d, 2-H$_{eq}$).

90 0.8(9H, s -ab,4 CMe$_3$), 0.8(3H, t, Me), 1.7(1H, tt, 5-H$_{ax}$), 2.0(2H, q, 2-H$_{eq}$), 2.4(2H, dd, 4/6-H$_{eq}$), 2.7(2H, dd, 4/6-H$_{ax}$), 7.5–7.9(4H, dd, Ar—H).

91 0.9(15H, m), 1.4(2H, m), 1.7(4H, m), 2.0–2.9(4H, m), 3.4 and 4.0(1H, m).

TABLE 2-continued

Nuclear Magnetic Resonance Spectra:- $^1$H carried out in CDCl$_3$ and expressed as p.p.m. downfield from TMS, (number of protons, multiplicity, JHz, assignment).

92  0.9(12H, m), 1.3–1.7(9H, m), 1.5 and 1.8(3H, s),2.0–3.0(4H, m).
93  0.9(15H, m), 1.6(4H, m), 2.0–3.0(4H, m), 3.5 and 4.1(1H, m).
94  0.9(15H, m), 1.3(1H, m), 1.4 and 1.7(3H, s), 1.6(5H, m), 2.0–2.9(4H, m).
95  0.9(12H, m), 1.3–1.7(5H, m), 2.2(2H, m), 1.8(4H, m), 4.5(1H, s), 5.2(2H, m).
96  0.9(12H, m), 1.2–1.8(13H, m), 2.0–2.9(4H, m), 3.4 and 4.0(1H, m).
97  0.9(12H, m), 1.4(5H, m), 1.7(2H, m), 2.0–2.9(4H, m), 3.4 and 4.0(1H, m).
98  0.9(9H, s), 1.4(1H, m), 1.4 and 1.8(3H, s), 1.6(6H, m), 1.9(2H, m), 2.0–2.9(4H, m), 2.2(2H, m), 5.1(1H, m).
99  0.9(9H, s), 1.6(1H, m), 1.6, 1.65 and 1.7(9H, s), 2.1(4H, m), 2.8(4H, m), 4.8(1H, d), 5.1(2H, m).
100 0.9(12H, m), 1.4(2H, m), 1.6(1H, m), 2.0(2H, m), 2.8(4H, m), 4.6(1H, d), 5.5 and 5.9(2H, m).
101 0.9 and 1.0(9H, s), 1.6(1H, m), 1.8(3H, m), 2.9(4H, m), 4.7(1H, d), 5.5–6.2(4H, m).
102 0.9(9H, s, —CMe$_3$), 1.3–2.2(10H, m), 1.65(1H, tt, $J$11 and 2.5Hz, 5-H$_{ax}$), 2.04(1H, d, $J$2Hz,≡CH),
    2.65(2H, dd, $J$13.8 and 11Hz, 4/6-H$_{ax}$), 2.91(2H, dd, $J$13.8 and 7.5Hz, 4/6-H$_{eq}$), 3.98(1H, dd, $J$6Hz, 2-H$_{ax}$).
103 0.9(9H, s, —CMe$_3$), 1.0–2.28(10H, m),1.8(1H, tt, $J$10 and 4Hz, 5-H$_{ax}$), 2.05(1H, d, $J$2Hz, ≡C—H),
    2.6(2H, dd, J 14 and 4Hz, 4/6-H$_{eq}$), 2.8(2H, dd, J14 and 10Hz, 4/6-H$_{ax}$), 3.25(1H, d, J9.1Hz, 2-H$_{eq}$).
104 0.92(9H, s, —CMe$_3$), 1.23(6H, m, cyclohexyl), 1.68(2H, m, 5-H$_{ax}$ + cyclohexyl-1-H), 1.8(4H,m, cyclohexyl-2-CH$_2$x2), 2.69(2H, dd, 4/6 H$_{ax}$), 2.93(2H, dd, 4/6-H$_{eq}$), 4.0(1H, d, 2-H$_{ax}$).
105 0.99(9H, s, —CMe$_3$), 1.75(1H, tt, 5-H$_{ax}$), 2.81(2H, dd, 4/6-H$_{ax}$), 2.99(2H, dd, 4/6-H$_{eq}$), 5.16(1H, s, 2-H$_{ax}$), 7.35(1H, d, Ar—H), 8.1(1H, dd, 4/6-H$_{ax}$), 8.81(1H, d, Ar—H).
106 0.99(9H, s, —CMe$_3$), 1.87(1H, d, 5-H$_{ax}$), 2.57(2H, dd, 4/6-H$_{ax}$), 2.72(2H, dd, 4/6-H$_{eq}$), 4.84(1H, s, 2-H$_{eq}$), 7.36(1H, d, Ar—H), 8.1(1H, dd, Ar—H), 8.82(1H, d, Ar—H).
107 0.95(9H, s, —CMe$_3$), 1.25, 1.3, 1.35, 1.4(6H, s, 2xMe), 1.7(2H, m, 5-H$_{ax}$ and cyclopropyl H), 2.8(4H, m, 4/6-H$_{ax+eq}$), 3.4 and 3.8(1H, m, 2-H).
108 0.9(9H, s, —CMe$_3$), 0.95(9H, s, —CMe$_3$), 1.45–1.8(4H, m, 2xCH$_2$), 2.57–2.95(4H, m, 4/6-H$_{ax+eq}$), 3.95(1H, t, 2-H$_{ax}$).
109 0.9(9H, s, —CMe$_3$), 0.95(9H, s, —CMe$_3$), 1.3–1.8(4H, m, 2xCH$_2$), 1.95–2.05(1H, m, 5-H$_{ax}$), 2.7–3.0(4H, m, 4/6-H$_{ax+eq}$), 3.3 and 4.0(1H, t, 2-H).
110 0.9(9H, s, —CMe$_3$), 1.0(9H, s, —CMe$_3$),1.6–1.7(1H, m, 5-H$_{ax}$), 2.6–2.9(4H, m, 4/6-H$_{ax+eq}$), 4.6–6.0(2H, m, 2x =CH).
111 0.8 and 1.0(18H, s, —CMe$_3$x2), 1.6(3H, m, 5-H$_{ax}$ + CH$_{2eq}$), 2.1(2H, d, CH$_{2ax}$), 2.6–9(4H, m, 4/6-H$_{ax+eq}$), 3.65(1H, t, 2-H$_{eq}$), 4.0(1H, t, H-2$_{ax}$).
112 0.9(9H, s, —CMe$_3$), 1.1(9H, s, —CMe$_3$), 1.7(1H, m, 5-H$_{ax}$), 1.85(2H, s, CH$_{2eq}$), 1.95(2H, s, CH$_{2ax}$), 2.3–3.0(4H, m, 4/6-H$_{ax+eq}$).
113 0.9(9H, s, —CMe$_3$), 1.7(1H, tt, 5-H$_{ax}$), 2.1(1H, t, ≡C—H), 2.5–3.0(10H, m, SCH$_2$—CH$_2$ + 4/6-H$_{ax+eq}$), 3.7(1H, t, 2-H$_{eq}$), 4.2(1H, t, 2-H$_{ax}$).
114 0.9(9H, s, —CMe$_3$), 1.6(1H, tt, 5-H$_{ax}$), 1.8(3H,d, =C—Me), 2.0(1H, t, ≡C—H), 2.4(4H, m, CH$_2$x2),
    2.6–9(4H, m, 4/6-H$_{ax+eq}$), 4.6(1H, s, 2-H$_{ax}$), 5.8(1H, t, =C—H).
115 0.9 and 0.95(18H, s, —CMe$_3$ × 2), 1.25(3H, s, Me), 1.4(2H, m, CH$_2$), 1.7(2H, m, CH$_2$), 2.45(2H, d, 4/6-H$_{ax}$), 3.1(2H, d, 4/6-H$_{eq}$), 3.7(1H, t, 2-H$_{ax}$).
116 0.88 and 0.95(15H, s, —CMe$_3$ + —CMe$_2$), 1.45–75(5H, m, 5-H$_{ax}$ + CH$_2$x2), 2.75(4H, m, 4/6-H), 3.02 and 3.12(2H, s, CH$_2$O), 3.32 and 3.35(3H, s, OMe), 3.38 and 3.95(1H, t, 2-H).
117 0.25(4H, m, cyclopropyl), 0.92 and 1.04(3H, s, C—Me), 1.0(9H, s, —CMe$_3$), 1.35–2.2(5H, m, 5-H$_{ax}$, CH$_2$x2, 2.58–9(4H, m, 4/6-H), 3.45 and 4.01(1H, t, 2-H).
118 0.8(3H, t, Me), 0.80, 0.82 and 0.9(15H, —CMe$_3$ + CMe$_2$), 1.2(2H, q, CH$_2$), 1.35(2H, m, CH$_2$), 1.58–2.0(3H, m, 5-H$_{ax}$ + CH$_2$), 2.75(4H, m, 4/6-H$_{ax+eq}$), 3.35 and 3.97(1H, t, 2-H).
119 0.78(3H, t, Me), 0.81(6H, s, —CMe$_2$), 0.9(9H, s, —CMe$_3$), 1.35(2H, m, CH$_2$), 1.65(3H, m, 5-H$_{ax}$ + CH$_2$), 2.64(2H, dd, 4/6-H$_{ax}$), 2.85(2H, dd, 4/6-H$_{eq}$), 3.95(1H, t, 2-H).
120 1.0(9H, s, —CMe$_3$), 2.2(1H, tt, 5-H$_{ax}$), 2.75(4H, m, 4/6-H$_{ax+eq}$), 3.1(1H, s, ≡C—H), 4.5(1H, s, 2-H$_{ax}$),
    7.45(4H, m, Ar—H).
121 0.9(9H, s, —CMe$_3$), 1.1(9H, s, —CMe$_3$), 2.1(1H, m, 5-H$_{ax}$), 2.5(4H, m, 4/6-H), 4.2 and 4.6(1H, s, 2-H).
122 1.0(9H, s, —CMe$_3$), 2.1(1H, tt, 5-H$_{ax}$), 2.7(4H, m, 4/6-H$_{ax+eq}$), 4.4(1H, s, 2-H$_{ax}$), 7.3(4H, m, Ar—H).
123 1.0(9H, s, —CMe$_3$), 1.6(1H, m, 5-H$_{ax}$), 2.0(3H, s, 2-Me), 2.6(4H, m, 4/6-H$_{ax+eq}$), 7.5(4H, s, Ar—H).
124 1.0(9H, s, —CMe$_3$), 1.3(9H, s, —CMe$_3$), 2.1(1H, m, 5-H$_{ax}$), 3.2(4H, m, 4/6-H$_{ax+eq}$), 4.6(1H, s, 2-H$_{ax}$).
125 0.9(9H, s, —CMe$_3$), 1.2(9H, s, —CMe$_3$), 1.5(1H,m, 5-H$_{ax}$), 2.2–3.6(4H, m, 4/6-H$_{ax+eq}$), 3.6 and 5.1(1H, s, 2-H).
126 0.95(9H, s, —CMe$_3$), 1.6(1H, tt, $J$, 11.5 and 2.5Hz, 5-H$_{ax}$), 1.8(3H, s, 2-Me), 2.8(1H, s, ≡C—H),
    2.85(2H, dd, $J$, 14.5 and 2.5Hz, 4/6-H$_{eq}$), 3.1(2H, dd, $J$, 14.5 and 11.5Hz, 4/6-H$_{ax}$).
127 0.95(9H, s), 1.0–2.4(15H, m), 2.6–9(4H, m), 3.4–7(2H, m).
128 0.95(9H, s), 1.2–1.8(13H, m), 2.0–4(4H, m), 2.6–2.9(4H,m), 4.1–2(2H, m).
129 1.0(9H, s, —CMe$_3$), 1.8(1H, t, 5-H$_{ax}$), 2.9(4H, m, 4/6-H$_{ax+eq}$), 5.55(1H, s, 2-H$_{ax}$), 7.1(2H, m, Ar—H), 7.6(1H, m, Ar—H).
130 1.0(21H, m), 1.1(3H, m), 1.6(1H, m), 2.8(4H, m), 4.0(1H, m).
131 1.0(18H, m, —CMe$_3$x2), 1.5(1H, m, 5-H$_{ax}$), 2.8(4H, m, 4/6-H$_{ax+eq}$), 4.1 and 4.6(1H, d, 2-H), 5.5(2H, m, —CH=CH—).
132 0.9(21H, m), 1.5(5H, m), 2.7(4H, m), 3.5 and 4.0(1H, m).
133 1.0(9H, s, —Cme$_3$), 1.8(1H, t, 5-H$_{ax}$), 2.9(4H, m, 4/6-H$_{ax+eq}$), 4.0(3H, s, OMe), 5.2(1H, s, 2-H$_{ax}$), 7.8(4H, m, Ar—H).
134 1.0(15H, m), 1.4–2.0(5H, m), 2.1–3.0(4H, m), 5.2–6.0(2H, m)
135 1.0 and 1.1(9H, s, —CMe$_3$), 1.4(1H, m, 5-H$_{ax}$), 1.5 and 1.7(3H, d, 4-Me), 2.4–3.5(3H, m, 4/6-H), 5.2 and 5.3(1H, s, 2-H), 7.4(4H, m, Ar—H).

TABLE 2-continued

Nuclear Magnetic Resonance Spectra:- $^1H$ carried out in $CDCl_3$ and expressed as p.p.m. downfield from TMS, (number of protons, multiplicity, JHz, assignment).

136  0.9 and 1.0(9H, s, —CMe$_3$), 1.3 and 1.6(3H, d, 4-Me), 1.4(1H,m, 5-H$_{ax}$), 1.9(3H, s, 2-Me), 2.4–2.9(3H, m, 4/6-H), 7.6(3H, m, Ar—H).

137  0.9 and 1.0(9H, s, —CMe$_3$), 1.3 and 1.6(3H, d, 4-Me),1.4(1H, m, 5-H$_{ax}$), 1.9(3H, s, 2-Me), 2.9(3H, m, 4/6-H), 7.6(3H, m, Ar—H).

138  0.8 and 1.0(9H, s, —CMe$_3$), 1.3(3H, s, 5-Me$_{ax}$), 1.4 and 2.1(3H, s, 2-Me), 2.3–3.4(4H, m, 4/6-H$_{ax+eq}$), 7.6(4H, m, Ar—H).

139  0.95 and 0.97(9H, s), 1.0–2.4(15H, m), 2.5–2.9(4H, m).

140  i) 0.95(9H, s), 1.0–2.4(17H, m), 2.6–3.0(4H, m).
     ii) 0.95(9H, s), 1.0–2.4(14H, m), 2.6–3.0(4H, m), 4.01(1H, d).

141  0.9(9H, s, —CMe$_3$), 1.0–2.3(12H, m), 2.6–2.7(2H, m, 4/6-H$_{ax}$), 2.8–2.9(2H, m, 4/6-H$_{eq}$), 3.25 and 3.98(1H, d, 2-H$_{ax}$).

142  1.0(9H, s, —CMe$_3$), 1.7(1H, m, 5-H$_{ax}$), 2.0(3H, s, ≡CMe), 2.9(4H, m, 4/6-H$_{ax+eq}$), 5.1(1H, s, 2-H$_{ax}$), 7.4(4H, m, Ar—H).

143  1.0(9H, s, —CMe$_3$), 1.8(1H, t, 5-H$_{ax}$), 2.9(4H, m, 4/6-H$_{ax+eq}$), 5.1(1H, s, 2-H$_{ax}$), 7.4(4H, m, Ar—H).

144  0.9(9H, s, —CMe$_3$), 1.8(1H, t, 5-H$_{ax}$), 2.9(4H, m, 4/6-H$_{ax+eq}$), 5.1(1H, s, 2-H$_{ax}$), 7.6(4H, m, Ar—H)

TABLE 3

Dithianes:-Further Characterising Data

| Compound Number | Mass Spectrum:- Chemical Ionisation M + 1 *Electron impact M | m.p. °C. b.p. °C. or n$_D$ | Description |
|---|---|---|---|
| 1 | 331 | 150–5 | Crystalline solid |
| 2 | 287 | 162 | Crystalline solid |
| 3 |  | 180 | Crystalline solid |
| 4 | 277 | 149 | Crystalline solid |
| 5 | 345 | 106 | Crystalline solid |
| 6 | 349 | 189 | Crystalline solid |
| 7 | 359 | 135–6 | Crystalline solid |
| 8 | 291 | 96 | Crystalline solid |
| 9 | 321 | 100–123 | Crystalline solid |
| 10 |  | 146 | Crystalline solid |
| 11 | *291 | 103–112 | Crystalline solid |
| 12 | 335 | 153 | Colourless crystals |
| 13 | 335 | 130 | Colourless powder |
| 14 | 345 | 117 | White crystalline solid |
| 15 | 321 | 121–123 | White crystalline solid |
| 16 | 345 | 95 | Pale yellow crystalline solid |
| 17 | 257 | 143° | Pale yellow crystalline solid |
| 18 | 273 | 112° | Pale yellow crystalline solid |
| 19 | 271 | 136° | Pale yellow crystalline solid |
| 20 | 336 | 113 | white solid |
| 21 | 335 |  | white semi-solid |
| 22 | 335 |  | white solid |
| 23 | 345 | 141 | white solid |
| 24 | 331 | 92 | yellow solid |
| 25 | 336 |  | yellow oil |
| 26 | 336 |  | white semi-solid |
| 27 | 336 |  | yellow semi-solid |
| 28 | 335 | 61 | white solid |
| 29 | 335 | 106 | white solid |
| 30 | 349 | 163 | white solid |
| 31 | 321 | 152 | white solid |
| 32 | 421 |  | yellow oil |
| 33 | 421 |  | semi-solid |
| 34 | 389 | 68 | white solid |
| 35 |  | 111 | white solid |
| 36 | 413 | 125 | white solid |
| 37 |  | 119 | white solid |
| 38 | 289 |  | yellow semi-solid |
| 39 | 289 |  | yellow semi-solid |
| 40 |  | 144 | white solid |
| 41 | 322 | 138 | white solid |
| 42 |  |  | light brown solid |
| 43 |  | 135–6 | light brown solid |
| 44 |  | 140 | white crystals |
| 45 |  | 174 | white crystals |
| 46 |  | 116–8 | beige solid |
| 47 |  | 107–118 | light brown solid |
| 48 |  | 133–5 | white crystals |
| 49 | 357 | 1.5180 | brown oil |
| 50 | 357 | 1.4770 | brown oil |
| 51 | 339 | 155 | white solid |
| 52 | 307 | 149 | white solid |
| 53 | 349 | 117 | buff solid |
| 54 | 335 | 169 | yellow solid |

TABLE 3-continued

Dithianes:-Further Characterising Data

| Compound Number | Mass Spectrum:- Chemical Ionisation M + 1 *Electron impact M | m.p. °C. b.p. °C. or $n_D$ | Description |
|---|---|---|---|
| 55 | | 150 | buff solid |
| 56 | | 145 | white solid |
| 57 | | 122 | white solid |
| 58 | 389 | 138 | white solid |
| 59 | 365 | 66 | white solid |
| 60 | 321 | | yellow solid |
| 61 | | | yellow solid |
| 62 | | 105 | yellow solid |
| 63 | | 150 | white solid |
| 64 | 299 | 167 | white solid |
| 65 | 345 | 155 | white solid |
| 66 | 345 | | orange oil |
| 67 | 359 | 105 | white solid |
| 68 | 359 | 130 | white solid |
| 69 | 243 | — | yellow oil |
| 70 | 215 | 84 | white crystals |
| 71 | 215 | 70 | yellow crystals |
| 72 | 203 | — | yellow oil |
| 73 | | | yellow oil |
| 74 | | | yellow oil |
| 75 | 243 | 1.5430 | yellow oil |
| 76 | | 1.5424 | yellow oil |
| 77 | 229 | 82 | yellow solid |
| 78 | 287 | 60–2 | buff solid |
| 79 | 225 | | colourless oil |
| 80 | 257 | 87 | buff solid |
| 81 | 271 | 71–4 | buff solid |
| 82 | 283 | 143.5 | white solid |
| 83 | 321 | 128–30 | white solid |
| 84 | 397 | 108–12 | brown solid |
| 85 | 317 | 145–50 | white solid |
| 86 | 335 | 138–9 | white solid |
| 87 | 351 | 134–5 | brown solid |
| 88 | 273 | 94 | yellow solid |
| 89 | 283 | | yellow oil |
| 90 | 359 | 70 | white solid |
| 91 | 247 | 115°/0.2 mm | |
| 92 | 261 | 140°/0.2 mm | |
| 93 | 233 | 130°/0.8 mm | |
| 94 | 261 | 117°/0.3 mm | |
| 95 | 259 | 130°/0.2 mm | |
| 96 | 275 | 144°/0.2 mm | |
| 97 | 247 | 122°/0.3 mm | |
| 98 | 273 | | |
| 99 | 299 | | |
| 100 | 245 | | |
| 101 | 243 | 42–6° C. | colourless solid |
| 102 | 283 | 134 | white solid |
| 103 | 283 | 100–2 | white solid |
| 104 | | 95–6 | white solid |
| 105 | | 165–6 | white solid |
| 106 | | 106–7 | white solid |
| 107 | 313 | 111–23 | yellow solid |
| 108 | 261 | 115 | white solid |
| 109 | 261 | 101–3 | white solid |
| 110 | 259 | | |
| 111 | 247 | 63 | white solid |
| 112 | 261 | 51 | white solid |
| 113 | 275 | | yellow oil |
| 114 | 269 | | yellow oil |
| 115 | 275 | 96 | white solid |
| 116 | 291 | 1.5160 | colourless oil |
| 117 | 259 | | semi-solid |
| 118 | 275 | | semi solid |
| 119 | 275 | 73 | white solid |
| 120 | 293 | 221 | white solid |
| 121 | 273 | 184–8 | white solid |
| 122 | 347 | 176 | white solid |
| 123 | | 152–3 | white solid |
| 124 | 305 | 225–30 | white solid |
| 125 | 321 | 190–3 | white solid |
| 126 | 215 | 133 | buff solid |
| 127 | 303 | 119.5 | white solid |
| 128 | 345 | 73.2 | white solid |
| 129 | — | 151 | white solid |
| 130 | 275 | 42–5 | white solid |
| 131 | — | 100–3 | white solid |
| 132 | 275 | 71–3 | white solid |
| 133 | 311 | 166 | white solid |
| 134 | 259 | b.p.116/0.2 mm. | — |
| 135 | 345 | — | orange semi-solid |
| 136 | — | — | yellow-green oil |
| 137 | — | — | yellow oil |
| 138 | — | 70 | white solid |
| 139 | 297 | | white solid |
| 140 | 297 311 | | white solid |
| 141 | 283 | 98.7 | white solid |
| 142 | 291 | 160–1 | white solid |
| 143 | 337 | 114.2 | white solid |
| 144 | 353 | 133.7 | white solid |

We claim:
1. A compound of the formula (I)

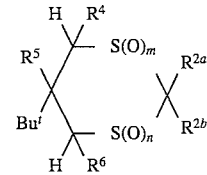

which contains between 10 and 27 carbon atoms, and wherein m and n are independently selected from 0, 1 and 2;

$R^{2a}$ is hydrogen, methyl, or ethyl;

$R^{2b}$ is acetylene or is a group $R^7$, wherein $R^7$ is a $C_{1-13}$ non-aromatic hydrocarbyl group, or a $C_{1-13}$ non-aromatic hydrocarbyl group substituted by a cyano, a $C_{1-4}$ alkoxycarbonyl group, one or two hydroxy groups, one to five halo atoms which are the same or different, or by one to three groups $R^8$ which are the same or different, and each contains one to four heteroatoms, which are the same or different, and are chosen from oxygen, sulfur, nitrogen and silicon, wherein $R^8$ is chosen from alkoxy, alkenyloxy, alkynyloxy, alkoxyalkoxy, acyloxy, alkylthio, alkenylthio, alkynylthio, alkynylsulphonyl, alkynylsulphinyl, alkynyloximino, trialkylsilyl, haloalkylthio, haloalkoxy, haloalkenyloxy, haloalkynyloxy, sulphonyl, sulphinyl, alkyloximino, carbalkoxy and mono or di-substituted alkylamino groups and wherein $R^8$ is linked via an oxygen, sulfur, nitrogen or silicon atom to $R^7$;

$R^4$ and $R^6$ are the same or different and are chosen from hydrogen, methyl, trifluoromethyl or cyano;

$R^5$ is hydrogen or methyl and $Bu^t$ is tertiary butyl, provided that $R^{2b}$ is not propyl or butyl.

2. A compound according to claim 1 wherein $R^{2b}$ is a group $-A(C\equiv C)Z$, wherein A is a $C_{3-5}$ aliphatic chain optionally containing a double bond, A being optionally substituted by halo, $C_{1-4}$ alkyl, $C_{1-4}$ haloaklyl, $C_{1-4}$ alkoxycarbonyl or cyano and Z is hydrogen, $C_{1-3}$ alkoxymethyl or a group $SiR^{14}R^{15}R^{16}$ wherein $R^{14}$ and $R^{15}$ are the same or different and are each $C_{1-4}$ aliphatic groups and $R^{16}$ is a $C_{1-4}$ aliphatic group or a phenyl provided that $R^{14}$, $R^{15}$ and $R^{16}$ do not contain more than 10 carbon atoms in total, and the phenyl group is additionally optionally substituted at the 2- or 6- or both 2- and 6- positions by fluoro or chloro.

3. A compound according to claim 1 wherein $R^{2b}$ is optionally substituted $C_{4-8}$ alkyl, the substituents being selected from halo, $C_{1-4}$ haloalkyl, cyano or a group $(C\equiv C)_p R^{9a}$ wherein p is 1 or 2 and $R^{9a}$ is hydrogen, bromo, chloro, iodo or a group $S(O)_q R^8$, $R^{9a}$ is an aliphatic group containing up to five carbon atoms optionally substituted by $C_{1-4}$ alkoxy, halo or hydroxy or $R^{9a}$ is a group $COR^{11}$ or $SiR^{14}$, $R^{15}$, $R^{16}$ wherein $R^{11}$ is hydrogen $C_{1-4}$ alkoxy, $C_{1-4}$ alkyl or a group $NR^{12}R^{13}$ where $R^{12}$ and $R^{13}$ are independently selected from hydrogen, methyl or ethyl and $R^{14}$ and $R^{15}$ are the same or different and are each $C_{1-4}$ aliphatic groups and $R^{16}$ is a $C_{1-4}$ aliphatic group and $R^{16}$ is a $C_{1-4}$ aliphatic group or a phenyl provided that $R^{14}$, $R^{15}$ and $R^{16}$ do not contain more than 10 carbon atoms in total, and the phenyl group is additionally optionally substituted at the 2- or 6- or both 2- and 6-positions by fluoro or chloro.

4. A compound of the formula (I) according to claim 1 wherein $R^4$ and $R^6$ are both hydrogen.

5. A compound of formula (Ia):

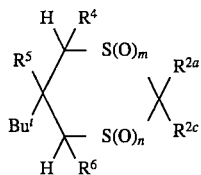

wherein m, n $R^{2a}$, $R^4$, $R^5$ and $R^6$ are as defined in claim 1 and $R^{2c}$ is a group $(C\equiv C)_r Y(C\equiv C)_t Z^2$ wherein r is 0 or 1 and t is 1 or 2 and the sum of r and t is not greater than 2, Y is a single bond, a group

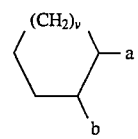

wherein v is 1, 2 or 3 and the $(C\equiv C)_t Z^2$ fragment is attached to the a or b position of the ring, or Y is a methylene or polymethylone chain containing between 2 and 8 carbon atoms in which one or two heteroatoms or double or triple bonds or both double and triple bonds may be interspersed, the chain being unsubstituted or substituted by one to four substituents which may be the same or different and are each independently selected from hydroxy, oxo, halo, $C_{1-4}$ alkyl, $C_{1-4}$ alkoxy, $C_{1-4}$ acyloxy, epoxy, a $C_{1-4}$ alkylidene group, a $C_{1-6}$ carbalkoxy group, $C_{1-4}$ haloalkyl or cyano, $Z^2$ is selected from hydrogen, $C_{1-10}$ hydrocarbyl optionally substituted by halo, $C_{1-4}$ alkoxy, hydroxy, oxo, a group $S(O)_q R^{10}$ where q is 0, 1 or 2 and $R^m$ is trifluoromethyl, methyl or ethyl, cyano, $C_{1-4}$ acyloxy or carbalkoxy, or $Z^2$ is halo or a group $SiR^{14}$, $R^{15}$, $R^{16}$ wherein $R^{14}$, $R^{15}$ and $R^{16}$ are the same or different and are each $C_{1-4}$ aliphatic groups and $R^{16}$ is a $C_{1-4}$ aliphatic group or a phenyl provided that $R^{14}$, $R^{15}$, and $R^{16}$ do not contain more than 10 carbon atoms in total, and the phenyl group is additionally optionally substituted at the 2- or 6- or both 2- and 6positions by fluoro or chloro or $Z^2$ is a group $R^{23}OCO$ wherein $R^{23}$ is $C_{1-4}$ alkyl; provided that $(C\equiv C)_r Y(C\equiv C)_t Z^2$ contains up to a maximum of 18 carbon atoms.

6. A compound selected from the group consisting of:

5(e)-tert-Butyl-2(e)-(3,3-dimethylbut-1-ynyl)-1,3-dithiane;
5(e)-tert-Butyl-2(e)-(trimethylsilylethynyl)-1,3-dithiane;
5(e)-tert-Butyl-2(e)-(3.3-dimethylbut-1-ynyl)-2(a)-methyl-1,3-dithiane;
trans-5(e)-tert-Butyl-2(e)-(pent-1-ynyl)-1,3-dithiane;
cis-5(e)-tert-Butyl-2(a)-(prop-1-ynyl)-1,3-dithiane;
trans-5(e)-tert-Butyl-2(e)-(prop-1-ynyl)-1,3-dithiane;
cis-5(e)-tert-Butyl-2(a)-(hex-1-en-5-ynyl)-1,3-dithiane;
trans-5(e)-tert-Butyl-2(e)-(hex-1-en-5-ynyl)-1,3-dithiane;
cis-5(e)-tert-Butyl-2(e)-(pent-4-ynyl)-1,3-dithiane;
trans-5(e)-tert-Butyl-2(e)-(hex-5-ynyl)-1,3-dithiane;
5(e)-tert-Butyl-2(e)-methyl-2(a)-(prop-1-ynyl)-1,3-dithiane;
5(e)-tert-Butyl-2(e)-methyl-2(a)-(trimethylsilylethynyl)-1,3-dithiane;
trans-5(e)-tert-Butyl-2(e)-[(E)-3,3,3-trichloroprop-1-enyl]-1,3-dithiane;
trans-5(e)-tert-Butyl-2(e)-(3,3,3- trichloropropyl)-1,3-dithiane;
trans-2(e)-(1-Bromo-3,3,3-trichloroprop-1-enyl)-5(e)-tert-Butyl-1,3-dithiane;
5-(e)-tert-Butyl-2(a)-methyl-2(e)-(3,3,3-trichloropropyl)-1,3-dithiane;
trans-5(e)-tert-Butyl-2(e)-(3-methoxy-3-methylbut-1-ynyl)-1,3-dithiane;
5(e)-tert-Butyl-2(e)-(3,3-dimethylbutyl)-1,3-dithiane;
trans-5(e)-tert-Butyl-2(e)-(3,3-dimethylbutyl)-1,3-dithiane;
cis-5(e)-tert-Butyl-2(a)-(3,3-dimethylbutyl)-1,3-dithiane;
5(e)-tert-Butyl-2(e)-(3,3-dimethylbut-1-enyl)-1,3-dithiane;
5(e)-tert-Butyl-2(e)-(2,2-dimethylpropyl)-2(a)-methyl-1,3-dithiane;
trans-5(e)-tert-Butyl-2(e)-((E)-1-methylhex-1-en-5-ynyl)-1,3-dithiane;
5(e)-tert-Butyl-2(e)-(3,3-dimethylbutyl)-5(a)-methyl-1,3-dithiane;
cis-5(e)-tert-Butyl-2(a)-(3,3-dimethylpentyl)-1,3-dithiane;
trans-5(e)-tert-Butyl-2(e)-(3,3-dimethylpentyl)-1,3-dithiane;
cis-5(e)-tert-Butyl-2(a)-(2,2-dimethylpropyl)-1,3-dithiane-1-oxide;
5(e)-tert-Butyl-2(a)-ethynyl-2(e)-methyl-1,3-dithiane.

7. A method for the control of arthropods which comprises administering to the arthropod or its environment an effective amount of a compound according to claim 1.

8. A method for the control of helminths which comprises administering to the helminth or its environment an effective amount of a compound according to claim 1.

9. A method for the control of arthropod or helminth infestations of animals, plants, stored products or an environment which method comprises administering an effective amount of a compound of claim 1.

10. A pesticidal composition comprising an effective amount of a compound according to claim 1 in admixture with a carrier.

* * * * *